US012672762B2

(12) United States Patent
Podpolucha et al.

(10) Patent No.: US 12,672,762 B2
(45) Date of Patent: Jul. 7, 2026

(54) ENDOSCOPIC DEVICES AND RELATED METHODS

(71) Applicant: CooperSurgical, Inc., Trumbull, CT (US)

(72) Inventors: James F. Podpolucha, Milford, CT (US); Richard I. Farrington, Waterbury, CT (US)

(73) Assignee: CooperSurgical, Inc., Trumbull, CT (US)

( * ) Notice: Subject to any disclaimer, the term of this patent is extended or adjusted under 35 U.S.C. 154(b) by 0 days.

(21) Appl. No.: 17/964,979

(22) Filed: Oct. 13, 2022

(65) Prior Publication Data

US 2023/0032730 A1 Feb. 2, 2023

Related U.S. Application Data

(63) Continuation of application No. 16/351,610, filed on Mar. 13, 2019, now Pat. No. 11,517,181.

(Continued)

(51) Int. Cl.
*A61B 1/00* (2006.01)
*A61B 1/005* (2006.01)
(Continued)

(52) U.S. Cl.
CPC ...... *A61B 1/00128* (2013.01); *A61B 1/00052* (2013.01); *A61B 1/00066* (2013.01);
(Continued)

(58) Field of Classification Search
CPC ............ A61B 1/00128; A61B 1/00052; A61B 1/00066; A61B 1/00096; A61B 1/00147;
(Continued)

(56) References Cited

U.S. PATENT DOCUMENTS 5,630,782 A 5/1997 Adair
5,928,137 A * 7/1999 Green .................... A61B 90/36
600/106

(Continued)

FOREIGN PATENT DOCUMENTS

CN 203829018 9/2014
DK 199900414 3/2001

(Continued)

OTHER PUBLICATIONS

International Preliminary Report on Patentability for International Application No. PCT/US2019/022117 dated Oct. 15, 2020.

(Continued)

*Primary Examiner* — Ryan N Henderson
*Assistant Examiner* — Pamela F Wu
(74) *Attorney, Agent, or Firm* — Fish & Richardson P.C.

(57) ABSTRACT

An endoscopic device includes a single-use cannula configured for insertion through a cervix into a uterus, a camera secured to a distal end region of the single-use cannula for acquiring images of the uterus, a connection hub secured to a proximal end region of the cannula, a reusable display configured to present the images acquired by the camera and that is securable to the connection hub, and a handle secured to the connection hub. The handle is pivotable between a first position in which the handle is stowed along the connection hub and arranged to prevent attachment of the reusable display to the connection hub and a second position in which the handle is deployed to an orientation that is antiparallel to the connection hub and arranged to permit attachment of the reusable display to the connection hub.

25 Claims, 42 Drawing Sheets

Related U.S. Application Data

(60) Provisional application No. 62/727,017, filed on Sep. 5, 2018, provisional application No. 62/652,485, filed on Apr. 4, 2018.

(51) Int. Cl.
A61B 1/04 (2006.01)
A61M 25/01 (2006.01)

(52) U.S. Cl.
CPC ...... A61B 1/00096 (2013.01); A61B 1/00147 (2013.01); A61B 1/0052 (2013.01); A61B 1/042 (2013.01); A61M 25/0105 (2013.01); A61B 1/00112 (2013.01)

(58) Field of Classification Search
CPC ... A61B 1/0052; A61B 1/042; A61B 1/00112; A61B 1/00045; A61B 1/005; A61B 17/320016; A61B 1/0011; A61M 25/0105
See application file for complete search history.

(56) References Cited

U.S. PATENT DOCUMENTS

| | | | |
|---|---|---|---|
| 5,957,937 A * | 9/1999 | Yoon | A61B 18/1445 606/147 |
| 6,679,882 B1 | 1/2004 | Kornerup | |
| 6,830,545 B2 | 12/2004 | Bendall | |
| 9,168,057 B2 | 10/2015 | Poulsen | |
| 9,504,512 B2 | 11/2016 | Poulsen | |
| 10,426,449 B2 * | 10/2019 | Fortson | A61B 17/0057 |
| 10,441,134 B2 | 10/2019 | Ouyang et al. | |
| 10,610,290 B2 | 4/2020 | Bjorn-Rasmussen et al. | |
| 10,722,283 B2 | 7/2020 | Larsen | |
| 10,835,303 B2 | 11/2020 | Poulsen | |
| 11,213,195 B2 | 1/2022 | Jensen | |
| 12,082,783 B2 | 9/2024 | Herriges et al. | |
| 2007/0249907 A1 | 10/2007 | Boulais et al. | |
| 2008/0108869 A1 | 5/2008 | Sanders et al. | |
| 2009/0254082 A1 | 10/2009 | Kornerup et al. | |
| 2010/0191053 A1 * | 7/2010 | Garcia | A61B 1/0057 600/109 |
| 2010/0191238 A1 | 7/2010 | Kornerup | |
| 2011/0130627 A1 | 6/2011 | McGrail et al. | |
| 2011/0184233 A1 | 7/2011 | Fructus et al. | |
| 2012/0289858 A1 * | 11/2012 | Ouyang | A61B 1/00101 600/562 |
| 2014/0111634 A1 * | 4/2014 | Mueckl | H04N 5/2252 348/82 |
| 2014/0235943 A1 | 8/2014 | Paris et al. | |
| 2014/0275763 A1 * | 9/2014 | King | A61B 1/00105 600/110 |
| 2015/0005760 A1 | 1/2015 | Poulsen | |
| 2015/0150441 A1 * | 6/2015 | Ouyang | A61B 1/015 600/109 |
| 2016/0270636 A1 | 9/2016 | Iwasaka et al. | |
| 2016/0367119 A1 * | 12/2016 | Ouyang | A61B 1/0676 |
| 2017/0078583 A1 | 3/2017 | Haggerty et al. | |
| 2017/0156575 A1 | 6/2017 | Aizenfeld et al. | |
| 2017/0188795 A1 | 7/2017 | Ouyang et al. | |
| 2017/0307872 A1 | 10/2017 | Hatase et al. | |
| 2017/0319047 A1 | 11/2017 | Poulsen et al. | |
| 2018/0132700 A1 | 5/2018 | Ouyang et al. | |
| 2018/0160893 A1 | 6/2018 | Truckai et al. | |
| 2018/0184892 A1 | 7/2018 | Truckai et al. | |
| 2018/0256009 A1 * | 9/2018 | Ouyang | A61B 1/00048 |
| 2019/0090847 A1 | 3/2019 | Yamamoto et al. | |
| 2019/0246873 A1 * | 8/2019 | Lu | A61B 1/0623 |
| 2019/0282070 A1 | 9/2019 | Vilhelmsen et al. | |
| 2019/0298161 A1 | 10/2019 | Jensen | |
| 2020/0214741 A1 * | 7/2020 | Coppedge | A61B 17/3421 |
| 2020/0221931 A1 | 7/2020 | Wilder et al. | |
| 2020/0275827 A1 * | 9/2020 | Weise | A61B 1/00114 |
| 2020/0305699 A1 | 10/2020 | Herriges et al. | |
| 2020/0359877 A1 | 11/2020 | Seow et al. | |
| 2020/0390316 A1 | 12/2020 | Hosogoe | |
| 2022/0160218 A1 | 5/2022 | Herriges et al. | |
| 2022/0249194 A1 | 8/2022 | Harrekilde-Petersen | |
| 2022/0330807 A1 | 10/2022 | Madsen et al. | |
| 2023/0141540 A1 | 5/2023 | Worsoe et al. | |
| 2024/0382080 A1 | 11/2024 | Herriges et al. | |

FOREIGN PATENT DOCUMENTS

| | | |
|---|---|---|
| EP | 1150616 | 9/2005 |
| EP | 0930047 | 1/2008 |
| EP | 3860485 | 8/2021 |
| JP | 1985-171405 | 9/1985 |
| JP | 2000-510362 | 8/2000 |
| JP | 2009-268523 | 11/2009 |
| JP | 2010-506669 | 3/2010 |
| JP | 2010-264063 | 11/2010 |
| JP | 2014-521373 | 8/2014 |
| JP | 2018-531058 | 10/2019 |
| WO | WO 2016/079141 | 5/2016 |
| WO | WO 2021/048367 | 3/2021 |

OTHER PUBLICATIONS

International Search Report and Written Opinion of the International Searching Authority for International Application No. PCT /US2019/022117 Jul. 15, 2019.

Letter from the U.S. Food and Drug Administration to LiNA Medical ApS, Re: K1 71113 LiNA OperaScope, dated Jan. 4, 2018.

LiNA OperaScope, Single-use Operative Hysteroscopy System, submitted to the U.S. Food & Drug Administration on Nov. 30, 2017.

* cited by examiner

To Proximal End

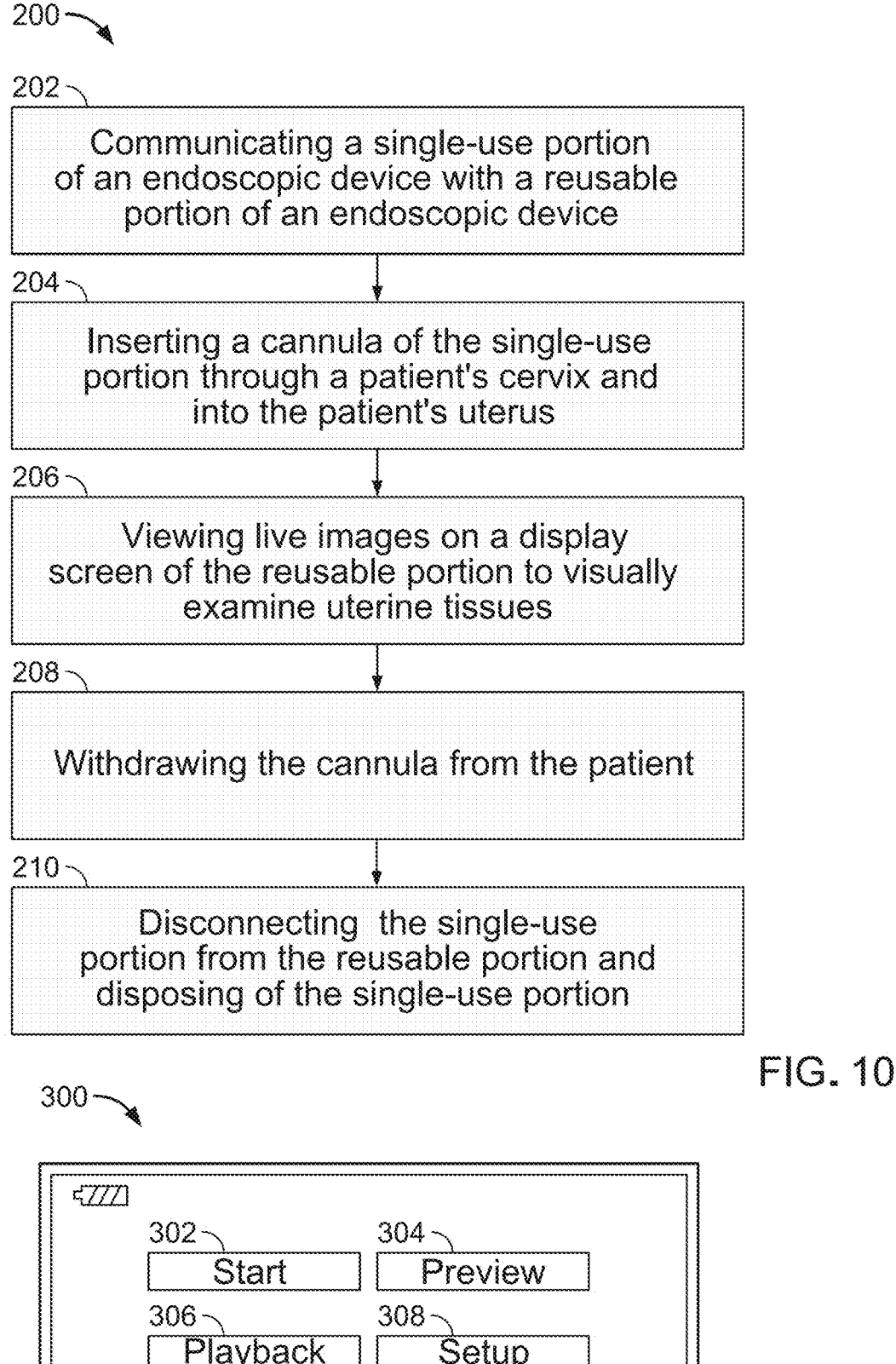

200

202

Communicating a single-use portion
of an endoscopic device with a reusable
portion of an endoscopic device

204

Inserting a cannula of the single-use
portion through a patient's cervix and
into the patient's uterus

206

Viewing live images on a display
screen of the reusable portion to visually
examine uterine tissues

208

Withdrawing the cannula from the patient

210

Disconnecting the single-use
portion from the reusable portion and
disposing of the single-use portion

302   Start     304   Preview

306   Playback     308   Setup

FIG. 11

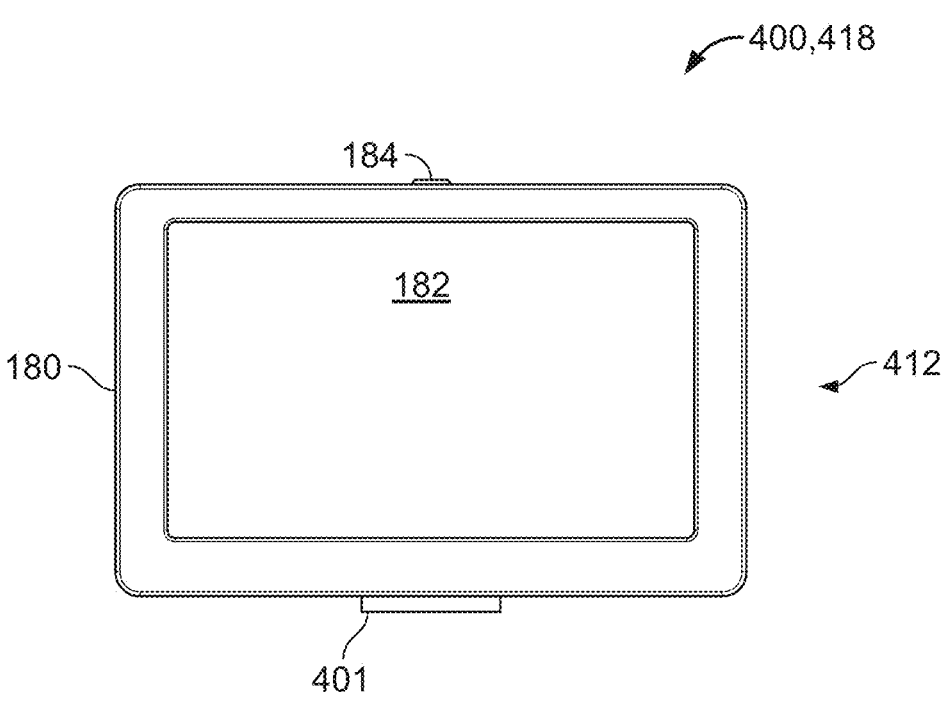
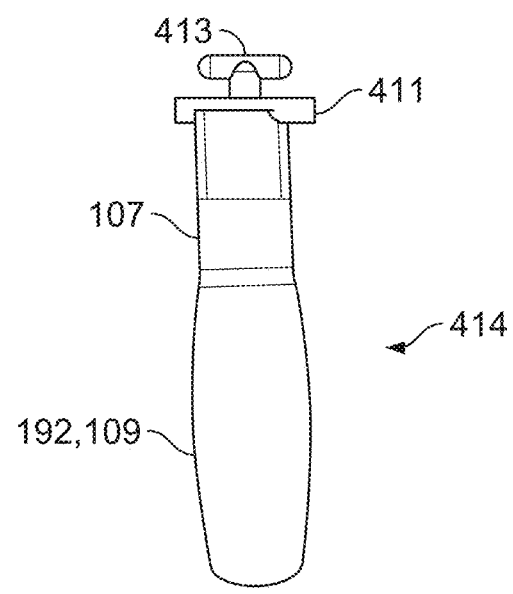
FIG. 13

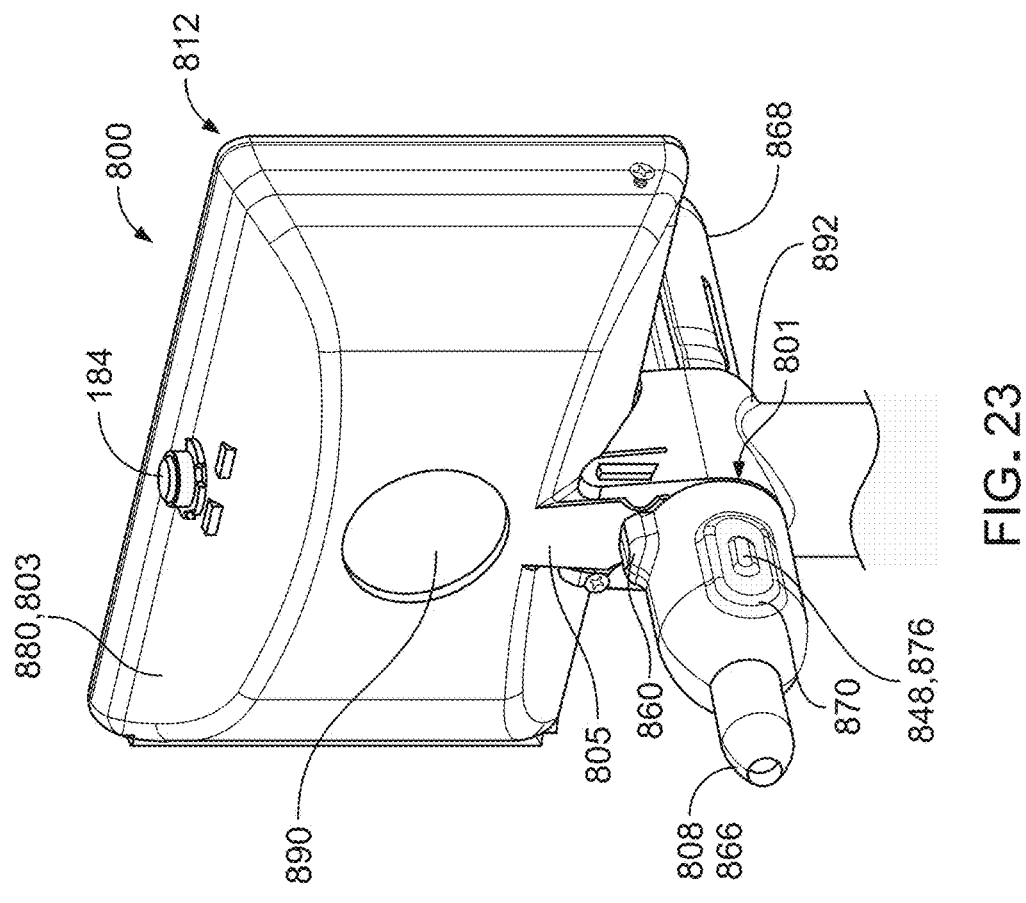
FIG. 23
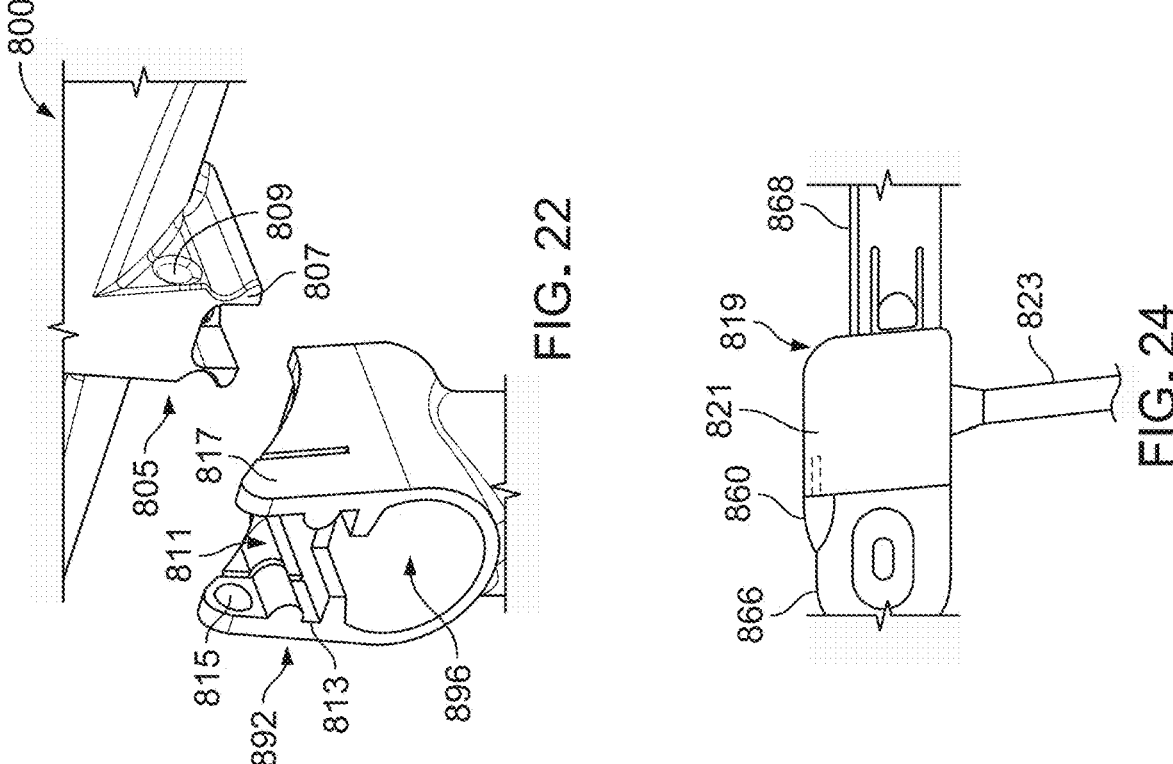
FIG. 22
FIG. 24

1500

1546,1568

1508

1512,1518

1566

1516

1502

1541

1543

1504

1610

1600

1606

1604

1600

1604

1602

1610

1608

ENDOSCOPIC DEVICES AND RELATED METHODS

CROSS-REFERENCE TO RELATED APPLICATIONS

This application is a continuation of and claims priority under 35 U.S.C. § 120 from U.S. patent application Ser. No. 16/351,610, filed on Mar. 13, 2019, which claims priority to U.S. Provisional Patent Application No. 62/652,485, filed on Apr. 4, 2018, and U.S. Provisional Patent Application No. 62/727,017, filed on Sep. 5, 2018. The entire contents of each of these priority applications are incorporated herein by reference.

TECHNICAL FIELD

This disclosure relates to endoscopic devices and related methods of examining a patient's uterus.

BACKGROUND

A hysteroscope is an endoscope that is designed for examining a patient's uterus (e.g., a uterine cavity). A hysteroscope typically includes a proximal portion that remains external to the patient's body during use and a distal portion that is inserted into the patient's uterus. The distal portion may include a tip that is sized to be inserted through the cervix and into the uterus to view and/or perform a surgery on the uterus, while the proximal portion provides features for manipulating the distal portion. Images captured at the tip of the distal portion can be viewed by a physician to examine the uterine cavity.

Once examination has concluded, the distal portion of the hysteroscope is withdrawn from the uterus through the patient's cervix.

SUMMARY

In general, this disclosure relates to endoscopic devices and related methods. Such endoscopic devices can be used for viewing and/or performing a surgery on a patient's uterus.

In one aspect, an endoscopic device includes a single-use cannula configured for insertion through a cervix into a uterus, a camera secured to a distal end region of the single-use cannula for acquiring images of the uterus, and a connection hub secured to a proximal end region of the cannula. The endoscopic device further includes a handle that is configured to be located at a fixed position along an axis of the single-use cannula, in which the handle can extend from the connection hub in a first direction with respect to the single-use cannula, and a reusable display configured to present the images acquired by the camera and to extend in a second direction with respect to the single-use cannula, wherein the second direction is opposite to the first direction.

Embodiments may include one or more of the following features.

In some embodiments, the single-use cannula defines a fluid port at the distal end region.

In certain embodiments, the connection hub is in fluid communication with a lumen of the single-use cannula.

In some embodiments, the connection hub includes a fluid port at which a fluidic device can supply fluid to or withdraw fluid from the lumen of the single-use cannula.

In certain embodiments, the connection hub includes an operative conduit that is sized to allow passage of a working tool and that is in fluid communication with the lumen of the single-use cannula.

In some embodiments, the connection hub provides electrical communication between the reusable display and the camera.

In certain embodiments, the connection hub includes an electrical port that is configured to mate with the reusable display.

In some embodiments, the connection hub includes a camera actuator that is operable to cause the camera to capture one or more of the images that are acquired.

In certain embodiments, the connection hub includes a housing by which the endoscopic device can be grasped to manipulate the single-use cannula.

In some embodiments, the handle is configured to provide a pistol-type grip with respect to the connection hub.

In certain embodiments, the handle includes elongate gripping members that are spaced apart from each other at nominal positions.

In some embodiments, the gripping members are flexible to be urged further apart from the nominal positions to allow passage of the connection hub therebetween.

In certain embodiments, the gripping members define a profile that is formed to engage the connection hub to secure the handle to the connection hub.

In some embodiments, the first direction is a downward direction and the second direction is an upward direction.

In certain embodiments, the handle and the reusable display are configured to be oriented substantially parallel to each other.

In some embodiments, one or both of the handle and the reusable display are attachable to the connection hub at a location along the axis of the single-use cannula that is distal to a proximal end of the connection hub.

In certain embodiments, the handle and the reusable display together provide an attachment mechanism that permits the handle and the reusable display to be attached to and detached from each other.

In some embodiments, the attachment mechanism includes one or more of a slot, a channel, an opening, a magnet, a plate, a detent, and a shoulder.

In certain embodiments, the endoscopic device further includes an electrical cable configured to electrically communicate the camera with the reusable display.

In some embodiments, the reusable display includes internal electronics configured to implement wireless communication between the reusable display and the camera.

In certain embodiments, the internal electronics are programmed to initiate presentation of one or more graphical user interfaces (GUIs) on the reusable display.

In some embodiments, the handle and the display are configured to be oriented at an angle of about 80° to about 115° with respect to the axis of the single-use cannula.

In certain embodiments, the handle is pivotable with respect to the connection hub.

In some embodiments, the display includes a magnet that is configured to interface with a metal plate that is separate from the endoscopic device.

In certain embodiments, the method further includes a component that is configured to support the display in an upright orientation.

In some embodiments, the handle is a multiple-use handle.

In certain embodiments, the handle is a single-use handle.

In some embodiments, the display includes a metal plate that is configured to interface with a magnet that is separate from the endoscopic device.

In certain embodiments, the handle is attachable to and detachable from the connection hub.

In another aspect, an endoscopic device includes a single-use cannula configured for insertion through a cervix into a uterus, a camera secured to a distal end region of the single-use cannula for acquiring images of the uterus, a connection hub secured to a proximal end region of the cannula, a reusable display configured to present the images acquired by the camera and that is securable to the connection hub, and a handle secured to the connection hub. The handle is pivotable between a first position in which the handle is stowed along the connection hub and arranged to prevent attachment of the reusable display to the connection hub and a second position in which the handle is deployed to an orientation that is antiparallel to the connection hub and arranged to permit attachment of the reusable display to the connection hub.

Embodiments may include one or more of the following features.

In some embodiments, the connection hub includes a housing by which the endoscopic device can be grasped when the handle is in the second position to manipulate the single-use cannula.

In certain embodiments, the handle is oriented parallel to the connection hub when the handle is in the first position.

In some embodiments, the handle provides a pencil-type grip when the handle is in the first position.

In certain embodiments, the handle provides a pistol-type grip when the handle is in the second position.

In some embodiments, the handle defines an interior profile that is formed to surround an exterior profile of the connection hub for stowing of the handle along the connection hub.

In certain embodiments, the handle includes two protrusions, and the connection hub includes a recess that is configured to mate with one of the two protrusions at a time to lock the handle in the first position or the second position with respect to the connection hub.

In some embodiments, the handle includes a peripheral edge that is arranged to obstruct attachment of the reusable display to the connection hub when the handle is in the first position and that is arranged to permit attachment of the reusable display to the connection hub when the handle is in the second position.

In certain embodiments, the endoscopic device further includes an electrical cable configured to electrically communicate the camera with the reusable display.

In some embodiments, the reusable display includes internal electronics configured to implement wireless communication between the reusable display and the camera.

In certain embodiments, the internal electronics are programmed to initiate presentation of one or more graphical user interfaces (GUIs) on the reusable display.

In some embodiments, the display includes a metal plate that is configured to interface with a magnet that is separate from the endoscopic device.

In certain embodiments, the handle is a single-use handle.

In some embodiments, the connection hub includes an operative conduit that is sized to allow passage of a working tool and that is in fluid communication with a lumen of the single-use cannula.

In certain embodiments, the connection hub provides electrical communication between the reusable display and the camera.

In some embodiments, the connection hub includes an electrical port that is configured to mate with the reusable display when the reusable display is attached to the connection hub.

In certain embodiments, the connection hub includes a camera actuator that is operable to cause the camera to capture one or more of the images.

In another aspect, an endoscopic system includes an endoscopic device and a docking station configured to mate with a reusable display of the endoscopic device. The endoscopic device includes a single-use cannula configured for insertion through a cervix into a uterus, a camera secured to a distal end region of the single-use cannula for acquiring images of the uterus, a connection hub secured to a proximal end region of the cannula, a reusable display configured to present the images acquired by the camera and that is securable to the connection hub, and a handle secured to the connection hub. The handle is pivotable between a first position in which the handle is stowed along the connection hub and arranged to prevent attachment of the reusable display to the connection hub and a second position in which the handle is deployed to an orientation that is antiparallel to the connection hub and arranged to permit attachment of the reusable display to the connection hub.

In some embodiments, the display is configured to slide onto the docking station.

In certain embodiments, the docking station includes a connection port by which data can be transferred from the display to a separate device.

Embodiments may provide one or more of the following advantages.

In some embodiments, the handle and the housing of the display are formed as a unitary, integrated component that facilitates installation of the handle and the display to the single-use portion of the endoscopic device.

In some implementations, a reusable portion of the endoscopic device (e.g., including both the handle and the display) is attached to a single-use portion of the endoscopic device (e.g., including the cannula, the connection hub, and an imaging system) at the connection hub prior to inserting the cannula into the patient. In such cases, a user can look in a direction of the patient to view images acquired by the imaging system on a screen of the display as the cannula is advanced into the patient. In some embodiments, the handle provides a pistol-type grip by which the user can easily grasp and manipulate the endoscopic device.

In some implementations, the reusable portion of the endoscopic device is not connected to the single-use portion while the cannula is inserted into the patient. In such cases, the reusable portion can be located (e.g., mounted to a holding structure) within a viewing region of a user and can be in wireless communication with the camera, such that the user can view images acquired by the imaging system on the screen of the display as the cannula is advanced into the patient. The housing of the connection hub can provide a handle surface by which the user can easily grasp and manipulate the single-use portion of the endoscopic device. With a weight, a bulk, and a moment arm of the reusable portion removed from the single-use portion, a user may be able to more easily and freely insert the cannula into the patient (e.g., as compared to insertion of the cannula with the reusable portion attached to the single-use portion) while advantageously maintaining an ability to visualize the cervix and the uterus on the screen as the cannula is inserted into the patient.

In some implementations, the reusable portion of the endoscopic device is connected to the single-use portion at a connection port by an extension cable (e.g., a display cable) prior to inserting the cannula into the patient, and the display can be attached to a proximal end of the extension cable within a viewing region of the user. Accordingly, a user can advantageously view images acquired by the imaging system on the screen of the display as the cannula is advanced into the patient, while the handle still provides a pistol-type grip by which the user can easily grasp and manipulate the single-use portion of the endoscopic device. Similar to a wireless configuration of the display, with a weight, a bulk, and a moment arm of the reusable portion removed from the single-use portion, a user may be able to more easily and freely insert the cannula into the patient, while advantageously maintaining an ability to visualize the cervix and the uterus on the screen as the cannula is inserted into the patient.

In certain embodiments, the handle and the display (e.g., a reusable display) are separable components, and such separation of the display from the handle can facilitate procedures for cleaning and disinfecting the display and the handle. In some examples, the handle is reusable. In some examples, the handle is disposable (e.g., a single-use component).

In some implementations, both the display and the handle of the endoscopic device can be attached to the connection hub prior to inserting the cannula into the patient. In some implementations, the display can be indirectly coupled to the connection hub prior to inserting the cannula into the patient. For example, the display can be unattached to (e.g., and in wireless communication with) the connection hub (e.g., with the handle attached to or unattached to the connection hub) while the cannula is inserted into the patient. In some implementations, the display can be connected to the connection hub at the connection port by a display cable prior to inserting the cannula into the patient (e.g., with the handle attached to or unattached to the connection hub). In cases where the display is indirectly coupled to the connection hub during insertion of the cannula into the patient, a user may be able to more easily and freely insert the cannula into the patient (e.g., due to a weight, a bulk, and a moment arm of the display removed from connection hub), while still advantageously maintaining an ability to visualize the cervix and the uterus on the screen as the cannula is inserted into the patient. In cases where the handle is attached to the connection hub, the handle can provide a pistol-type grip by which the user can easily grasp and manipulate the cannula (e.g., with or without the display attached to the connection hub).

In some embodiments, the connection hub includes an entry port that is configured to receive a working tool and to receive a fluidic device that can withdraw (e.g., suction) fluid and tissues that may be present within the operative conduit without leakage of fluids or tissues from the entry port. A rear location of the entry port (e.g., at a proximal opening of the connection hub and aligned with the axis of the cannula) can facilitate insertion of a working tool into the endoscopic device, as compared to placement of an entry port along a top or side surface.

In some embodiments, the display includes a power control element that is positioned along a rear surface of the display housing in order to reduce the risk of accidental actuation during use of the endoscopic device.

Other aspects, features, and advantages will be apparent from the description, the drawings, and the claims.

DESCRIPTION OF DRAWINGS

FIG. 10 is a flowchart showing a method of using the endoscopic device of FIG. 1 to perform a hysteroscopic procedure on a patient.

FIG. 11 illustrates a graphical user interface providing a home screen of a display of the endoscopic device of FIG. 1.

FIG. 13 is a front view of the reusable portion FIG. 12.

FIG. 22 is an enlarged exploded view of an attachment mechanism of the endoscopic device of FIG. 19.

FIG. 23 is a rear perspective view of the endoscopic device of FIG. 19.

FIG. 24 is a side view of an extension cable of the endoscopic device of FIG. 19.

DETAILED DESCRIPTION

Figure 1:
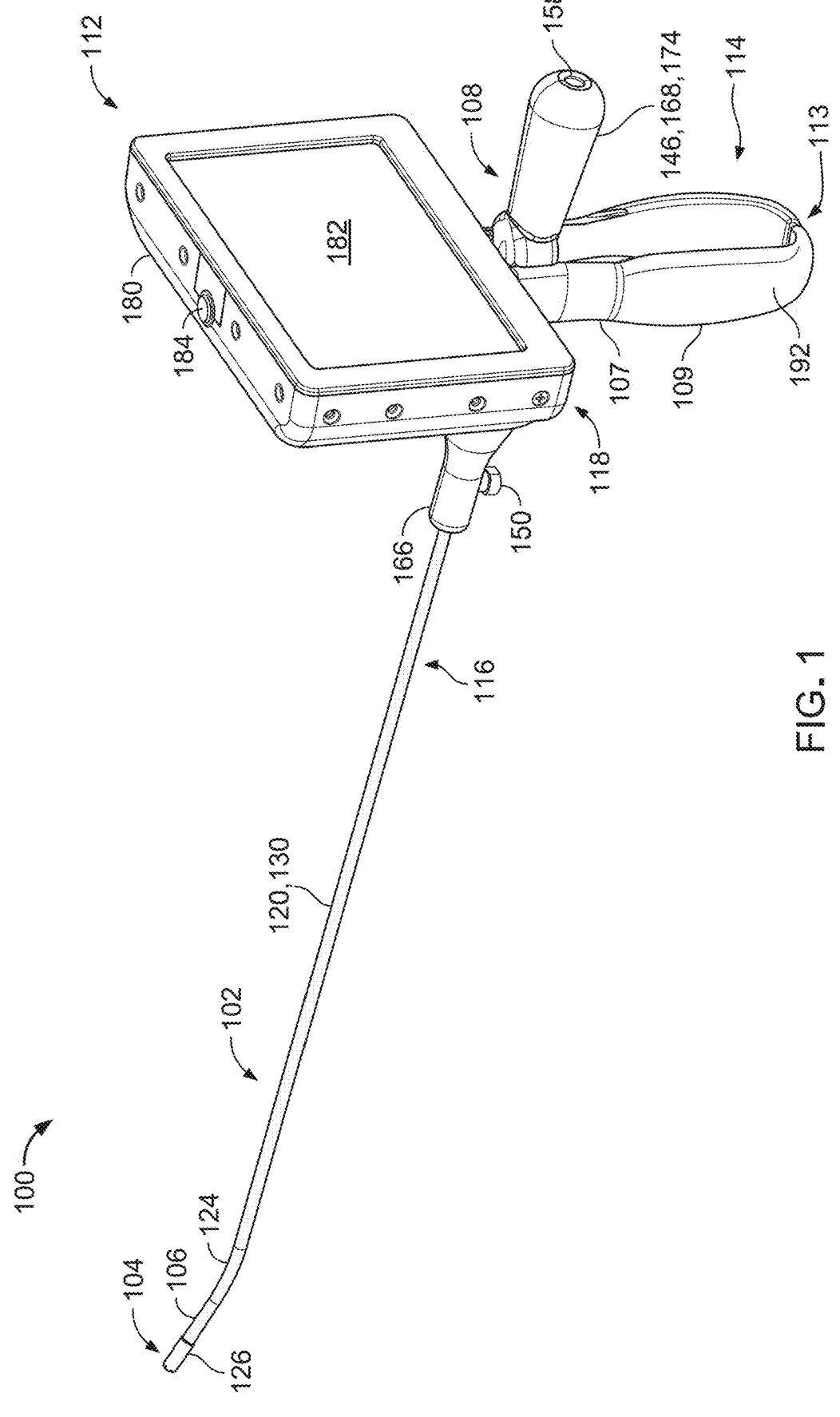
FIG. 1 is a perspective view of an endoscopic device.
Figure 2:
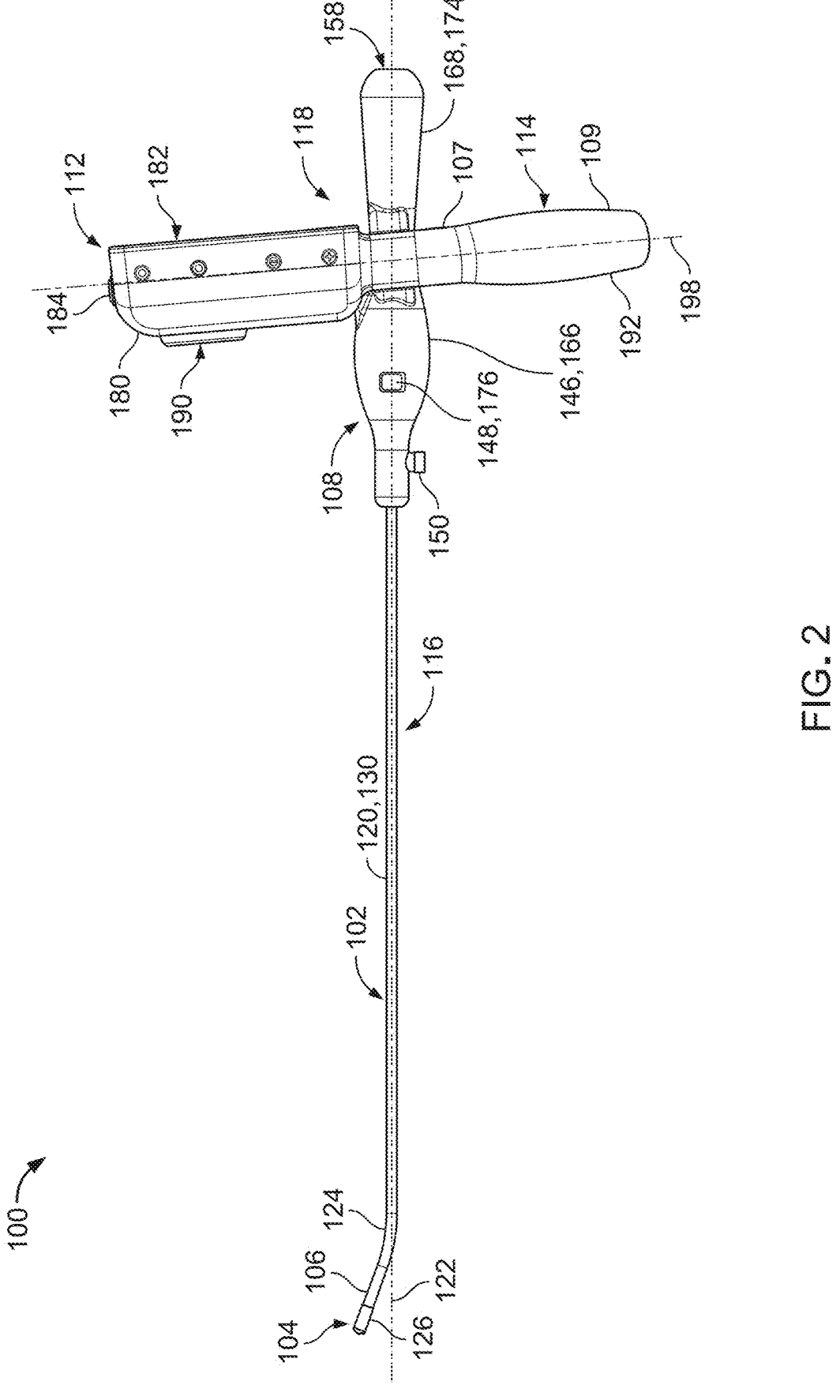
FIG. 2 is a side view of the endoscopic device of FIG. 1.

FIGS. 1 and 2 illustrate an endoscopic device 100 (e.g., a hysteroscope) that can be used to examine a patient's uterus (e.g., a uterine cavity). The endoscopic device 100 includes a cannula 102 that is formed to be inserted into the uterus (e.g., through the patient's vaginal canal and cervix), an imaging system 104 located at a distal tip 106 of the cannula 102 for imaging the uterus, and a connection hub 108 attached to a proximal end region 110 of the cannula 102. The endoscopic device 100 further includes a display 112 for viewing images acquired by the imaging system 104 and a handle 114 that extends from the display 112. The cannula 102, the imaging system 104, and the connection hub 108 together form a single-use portion 116 of the endoscopic device 100 that is designed to be disposed of following an examination of a single patient's uterus. The single-use portion 116 can be provided in a sealed, sterile package that can be stored until a time of use. The display 112 and the handle 114 together form a reusable portion 118 of the endoscopic device 100 that is designed to be attached to and detached from several single-use portions 116 to respectively examine multiple patients' uteruses. The reusable portion 118 is sterilized (e.g., cleaned and disinfected) following examination of each patient's uterus (e.g., prior to examining a next patient's uterus).

Referring to FIGS. 1-5, the cannula 102 is an elongate, generally tubular member that is sized to pass through a cervix into a uterus. The cannula 102 includes a shaft 120 and a cap 126 that secures the imaging system 104 to the distal tip 106 of the shaft 120. The shaft 120 includes a major portion 130 (e.g., including the proximal end region 110) with a central axis that defines a primary axis 122 of the cannula 102, the distal tip 106, and a distal bend 124 that connects the major portion 130 to the distal tip 106. The shaft 120 defines a lumen 128 that houses one or more electrical cables of the imaging system 104, that allows for passage of fluids between the distal tip 106 and the connection hub 108, and that allows for passage of a working tool extending distally from connection hub 108. The shaft 120 further defines a sidewall opening 144 along the proximal end region 110 through which fluid can be delivered to the lumen 128 or withdrawn (e.g., suctioned) from the lumen 128.

Figures 3, 4:
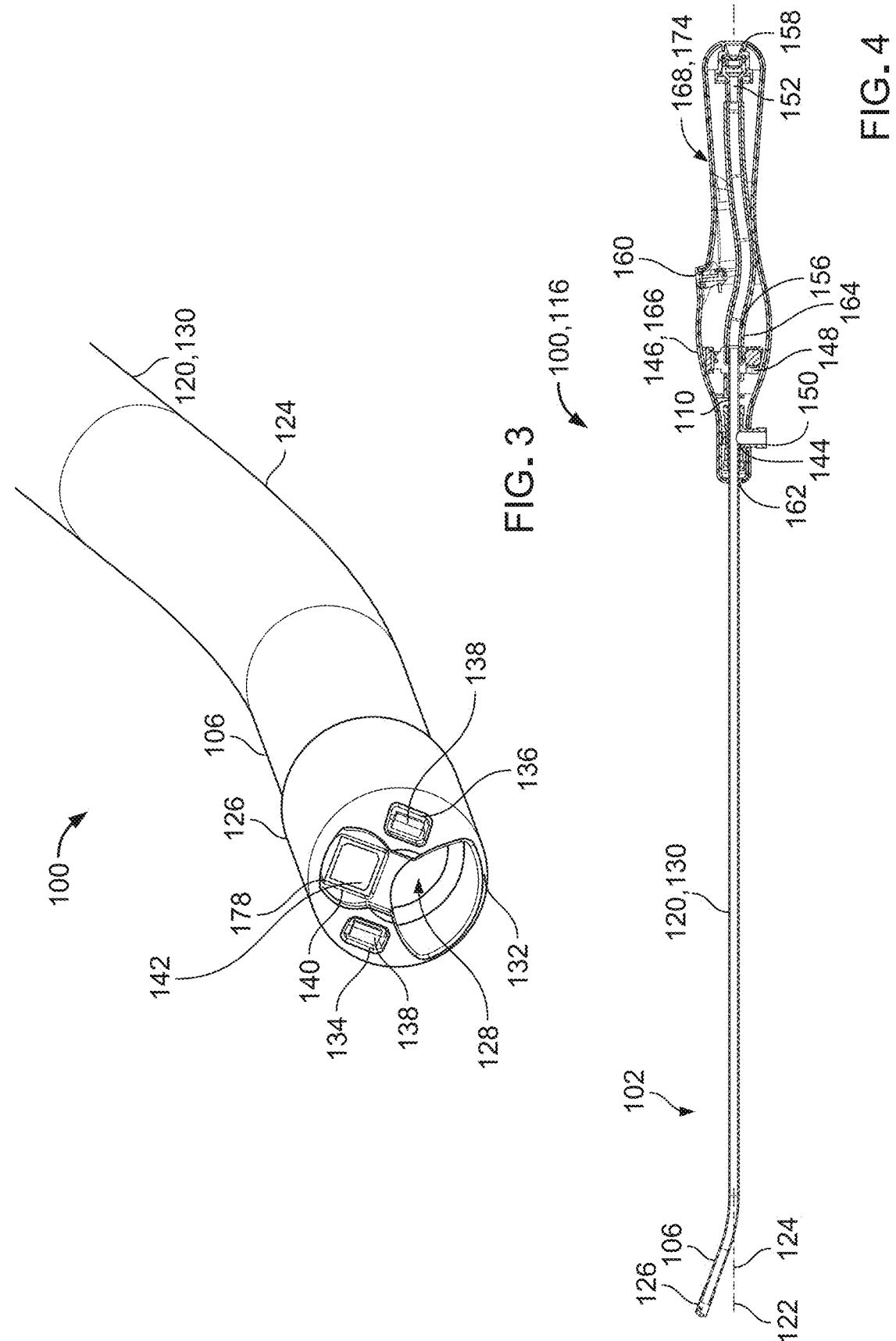
FIG. 3 is a perspective view of a distal end of the endoscopic device of FIG. 1.
FIG. 4 is a side cross-sectional view of a single-use portion of the endoscopic device of FIG. 1.

The cap 126 of the cannula 102 is secured to the distal tip 106 of the shaft 120 and defines multiple openings, as shown in FIG. 3. The openings include a luminal opening 132 (e.g., a forward facing fluid port) through which fluids and uterine tissue (e.g., endometrial tissue) can enter and exit the lumen 128 of the shaft 120, two lateral openings 134, 136 in which light emitting diodes (LEDs) 138 of the imaging system 104 are disposed, and a recessed opening 140 in which a camera 142 of the imaging system 104 is disposed.

The luminal opening 132 allows fluid (e.g., a saline solution, a hypotonic solution, or an isotonic fluid) to exit the distal tip 106 to flow into the uterus and to push tissue or other particulate matter away from the camera 142 so as to improve a quality of images acquired by the camera 142. For example, the luminal opening 132 can be useful in clearing away tissue debris that may collect on the distal tip 106 and otherwise impair imaging due to an overly bright appearance of the debris as light reflects from the debris. In some cases, the luminal opening 132 can also facilitate insertion of the cannula 102, as fluid exiting the luminal opening 132 may lubricate and partially distend tissues surrounding the distal tip 106. In this manner, the luminal opening 132 can reduce a risk of accidental damage to the vaginal cavity, to the cervix, or to the uterus during insertion of the cannula 102 into the patient. The luminal opening 132 is sized to permit passage of a 5 French biopsy tool. For example, the luminal opening 132 typically has a cross-sectional area of about 0.03 cm² to about 0.05 cm² and is about 50% to about 80% of a cross-sectional area of the lumen 128, itself.

The cannula 102 typically has a total length (e.g., as measured along the primary axis 122) of about 30.0 cm to about 34.0 cm (e.g., about 32.0 cm). The proximal end region 11—of the cannula 102 (e.g., the portion of the cannula 102 that is disposed within the connection hub 108) typically has a length of about 4.0 cm to about 4.6 cm (e.g., about 4.3 cm), such that a remaining portion of the cannula 102 extends distally from the connection hub 108 and is therefore exposed for insertion into the patient. The distal bend 124 typically has a radius of about 2.5 cm to about 7.5 cm (e.g., about 5.0 cm). The shaft 120 typically has a wall thickness of about 0.03 cm to about 0.05 cm (e.g., about 0.04 cm) and an inner diameter (e.g., a luminal diameter) of about 0.34 cm to about 0.36 cm (e.g., about 0.35 cm).

The shaft 120 is typically made of one or more materials that are flexible enough to allow the cannula 102 to bend by a small amount to be appropriately placed within the patient as desired, yet stiff enough to permit easy insertion into the vaginal canal. Example materials from which the shaft 120 is typically made include nylon, polysulfone, and polyether ether ketone (PEEK). The cannula 102 is typically manufactured primarily via extrusion and via secondary processes that may include one or more of punching, laser cutting, forming, and/or printing. The cap 126 is typically made of one or more materials including liquid crystal polymer (LCP) and is typically secured to the distal tip 106 of the shaft 120 via adhesive.

Figure 5:
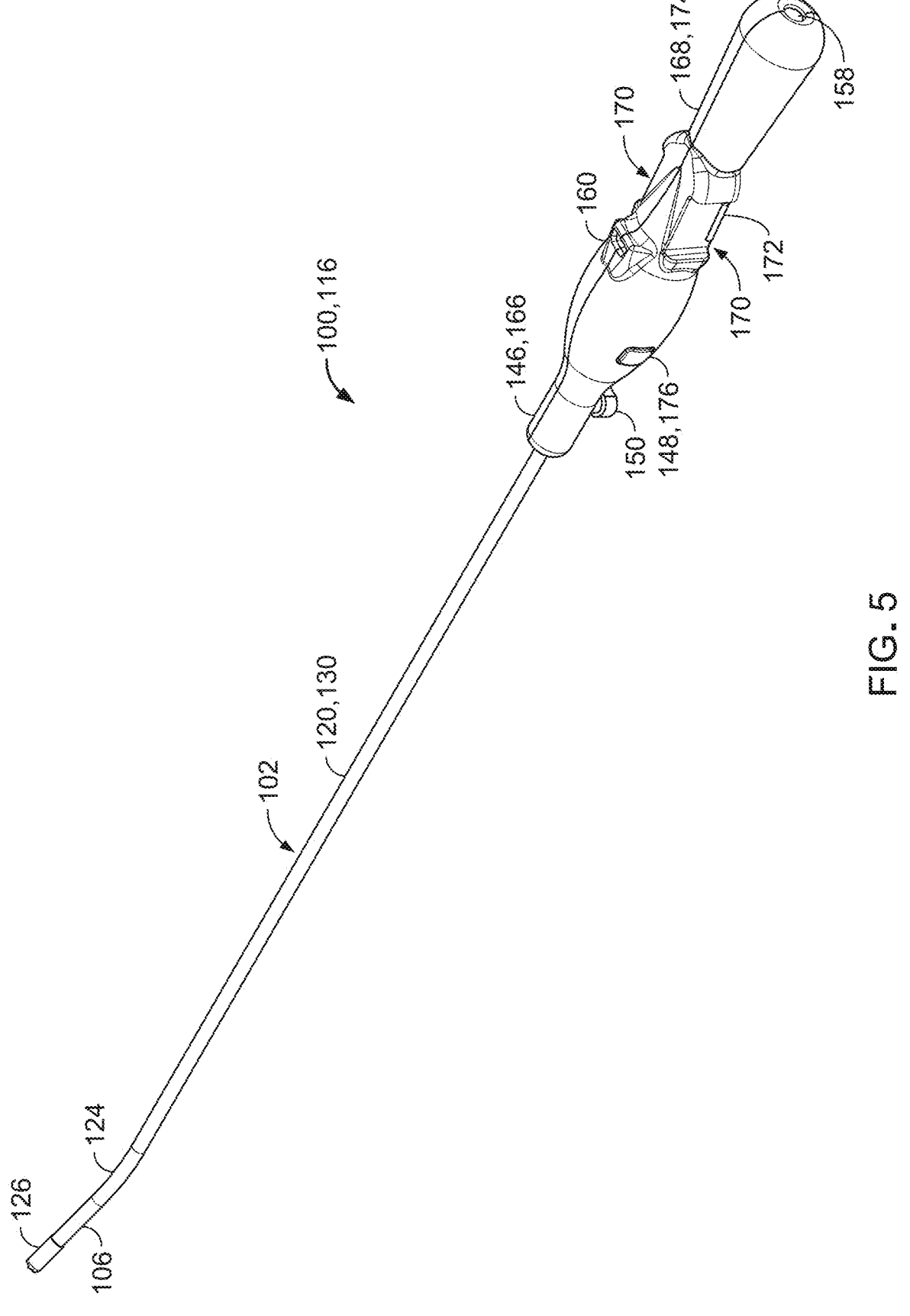
FIG. 5 is a perspective view of the single-use portion of FIG. 4.

Referring to FIGS. 4 and 5, the connection hub 108 surrounds the proximal end region 110 of the cannula 102 and serves as a mounting piece for the handle 114 of the reusable portion 118 of the endoscopic device 100. The connection hub 108 also provides several features for fluid and electrical communication between the proximal end region 110 of the cannula 102 and the distal tip 106 of the cannula 102. For example, the connection hub 108 includes a housing 146, a camera actuator 148 (e.g., providing two opposite push buttons 176), a fluid port 150 located adjacent the proximal end region 110 of the cannula 102, an entry port 152 disposed at a proximal opening 158 of the housing 146, and an operative conduit 156 that extends from the proximal end region 110 of the cannula 102 to the entry port 152.

The housing 146 is generally axially aligned with the primary axis 122 of the cannula 102 and has a generally curved profile that is laterally symmetric. The housing 146 defines a distal opening 162 through which the cannula 102 passes, an opening 154 (e.g., aligned with the sidewall opening 144 of the shaft 120) to which the fluid port 150 is secured, an operative channel 164 that surrounds the operative conduit 156, the proximal opening 158, and an upper connection port 160 (e.g., a micro HDMI port or another type of port) to which the display 112 or a display cable can be connected. In this regard, the connection hub 108 also includes electrical components (e.g., a small PCB or a flex circuit with an EEPROM, not shown) that communicate the camera actuator 148 with the connection port 160. The housing 146 further defines additional internal wall features (e.g., flanges, openings, brackets, tabs, etc.) that properly position the fluid port 150, the camera actuator 148, the connection port 160, and the entry port 152.

Referring particularly to FIG. 4, a distal portion 166 of the housing 146 provides fluid communication between the distal tip 106 of the cannula 102 (e.g., at the luminal opening 132) and the fluid port 150 and provides fluid communication between the distal tip 106 and the operative conduit 156 (e.g., for further fluid communication to the entry port 152).

The distal portion 166 of the housing 146 further provides electrical communication between the distal tip 106 of the cannula 102 (e.g., at the camera 142) and the camera actuator 148, and between the distal tip 106 (e.g., at the camera 142) and the display 112 (e.g., via the connection port 160).

Referring particularly to FIG. 5, a proximal portion 168 of the housing 146 provides two lateral receptacles 170 (e.g., slots) with detents 172 that mate with the handle 114 to secure the handle 114 (e.g., and the display 112 attached thereto) in place with respect to the connection hub 108, thereby locating the reusable portion 118 at a fixed position along the primary axis 122 of the cannula 102. The proximal portion 168 also provides a grip 174 that can be used to manipulate the single-use portion 116 of the endoscopic device 100 (e.g., or the display 112, when the reusable portion 118 of the endoscopic device 100 is attached to the single-use portion 116).

The housing 146 of the connection hub 108 typically has a length (e.g., as measured along the primary axis 122 of the cannula 102) of about 10 cm to about 20 cm (e.g., about 15 cm) and a maximum width of about 20 cm to about 30 cm (e.g., about 25 cm). The housing 146 typically has a handle seating width (e.g., as defined by a distance between opposite surfaces of the receptacles 170) of about 1.4 cm to about 1.8 cm (e.g., about 1.6 cm). The housing 146 is typically made of one or more materials including acrylonitrile butadiene styrene (ABS) or polycarbonate or copolyester and is typically manufactured via injection molding.

The fluid port 150 is formed as a T-connection and is typically made of one or materials including polycarbonate, ABS, or polypropylene. The fluid port 150 is formed to engage fluidic devices (e.g., syringes or extension tube sets) for delivering fluid to or withdrawing fluid from the lumen 128 of the cannula 102.

The operative conduit 156 may be curved (as shown) or straight and is typically made of one or more materials including polyvinyl chloride (PVC). In some embodiments, the curved profile of the operative conduit 156 provides space needed within the connection hub 108 for one or more electronic components, such as a PCB. The operative conduit 156 is sized to allow passage of a working tool from the entry port 152 to the distal tip 106 of the cannula 102. Example working tools that can be passed through the operative conduit 156 include various 5 French gauge biopsy instruments (e.g., forceps, graspers, and scissors).

The entry port 152 includes a valve assembly that is configured to receive a working tool without leakage of fluids or tissues from the entry port 152. Valve components of the entry port 152 are typically made of silicon or a thermoplastic elastomer. A rear location of the entry port 152 (e.g., at the proximal opening 158) facilitates insertion of a working tool into the endoscopic device 100, as compared to placement of a port along a top or side surface, as is typically the case with conventional devices.

Referring to FIGS. 3 and 4, the imaging system 104 includes the camera 142, the LEDs 138 located on opposite sides of the camera 142 to evenly illuminate surrounding tissues for image acquisition, the camera actuator 148, the one or more electrical cables (e.g., one or more video and control cables, not shown) that extend from the camera 142 and the LEDs 138 to the camera actuator 148 and to the connection port 160, and other electrical components that provide electrical communication amongst the various components of the imaging system 104 and the connection port 160 of the connection hub 108. In some embodiments, the one or more electrical cables extend through the lumen 128 of the cannula 102. In some embodiments, the one or more electrical cables extend within channels in a sidewall of the cannula 102. In some embodiments, the one or more electrical cables may be replaced with a flex circuit member to carry the electrical communications.

The push buttons 176 of the camera actuator 148 serve as Snap/Video buttons that control capture (e.g., recording and/or storing) of still images and video from the camera 142, such that pressing either or both of the push buttons 176 for a threshold period (e.g., 1 second) or less results in capture of a single, still photo, whereas pressing either or both of the push buttons 176 for longer than the threshold period results in capture of a video recording. While a video is being recorded, a single press of a push button 176 stops capture of the video. The push buttons 176 can be easily pressed with one or more of a user's fingers on the hand that is holding or inserting the endoscopic device 100. An overhanging edge 178 of the cap 126 acts as a lens hood that shields light from directly impinging on the LEDs 138 and from entering an aperture of the camera 142.

The camera 142 includes a complementary metal-oxide-semiconductor (CMOS) sensor module, a lens, and a glass cover. The CMOS sensor module includes a low voltage color CMOS image sensor core, an image sensor processor, and an image output interface circuitry. By providing integrated digital video processing within the CMOS sensor module, some aspects of video processing can be performed directly on the same printed circuit board (PCB) as the CMOS sensor module, or on the same substrate in which the CMOS is formed such that the imaging plane of the CMOS and the plane along which the video processing circuits extend substantially coincide. Furthermore, the display 112 includes an image signal processing (ISP) chip that can perform additional aspects of the image processing and that can support various video formats. The video signal from the CMOS sensor module can be in any suitable video format, such as National Television System Committee (NTSC), Phase Alternating Line (PAL), or another common video format.

Figure 6:
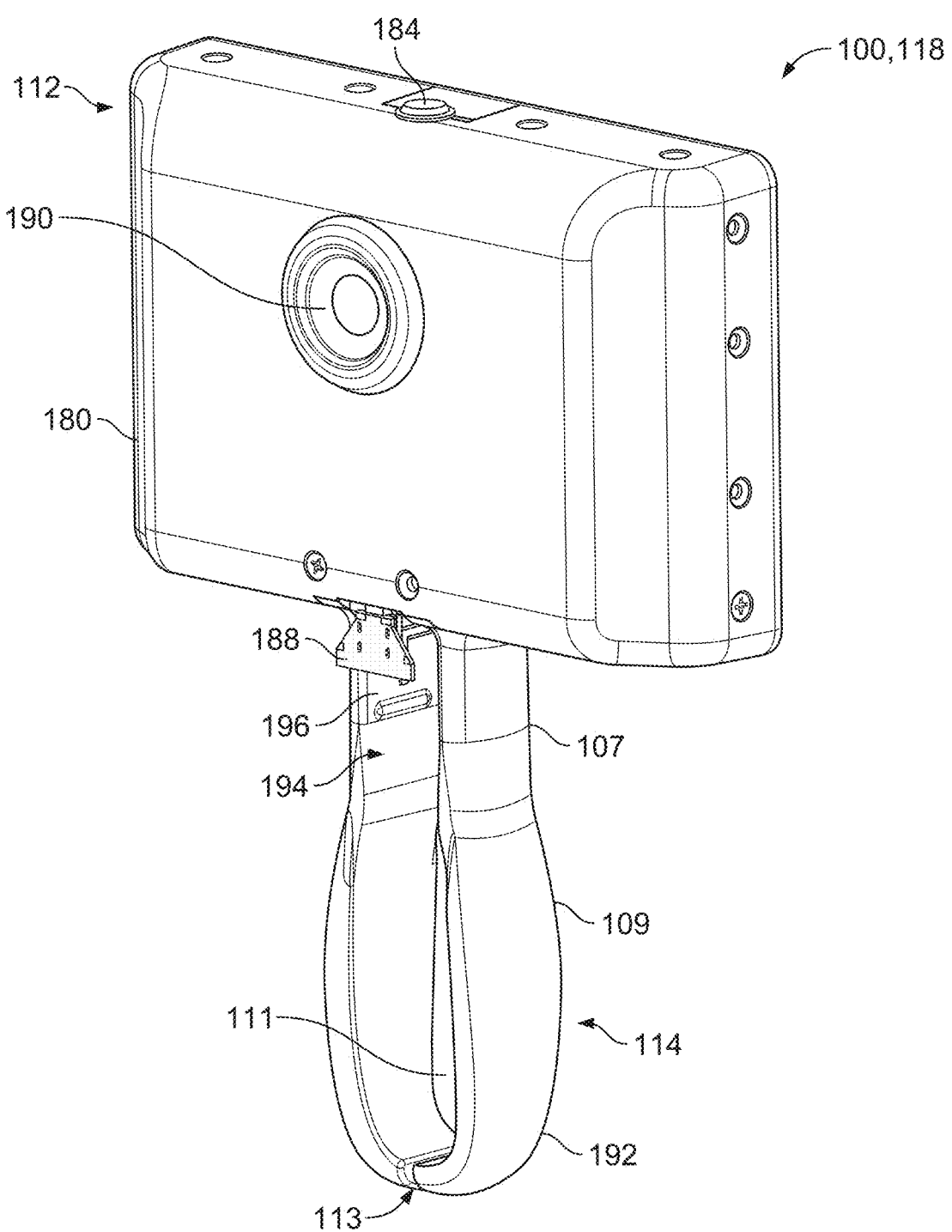
FIG. 6 is a rear perspective view of a reusable portion of the endoscopic device of FIG. 1.
Figure 7:
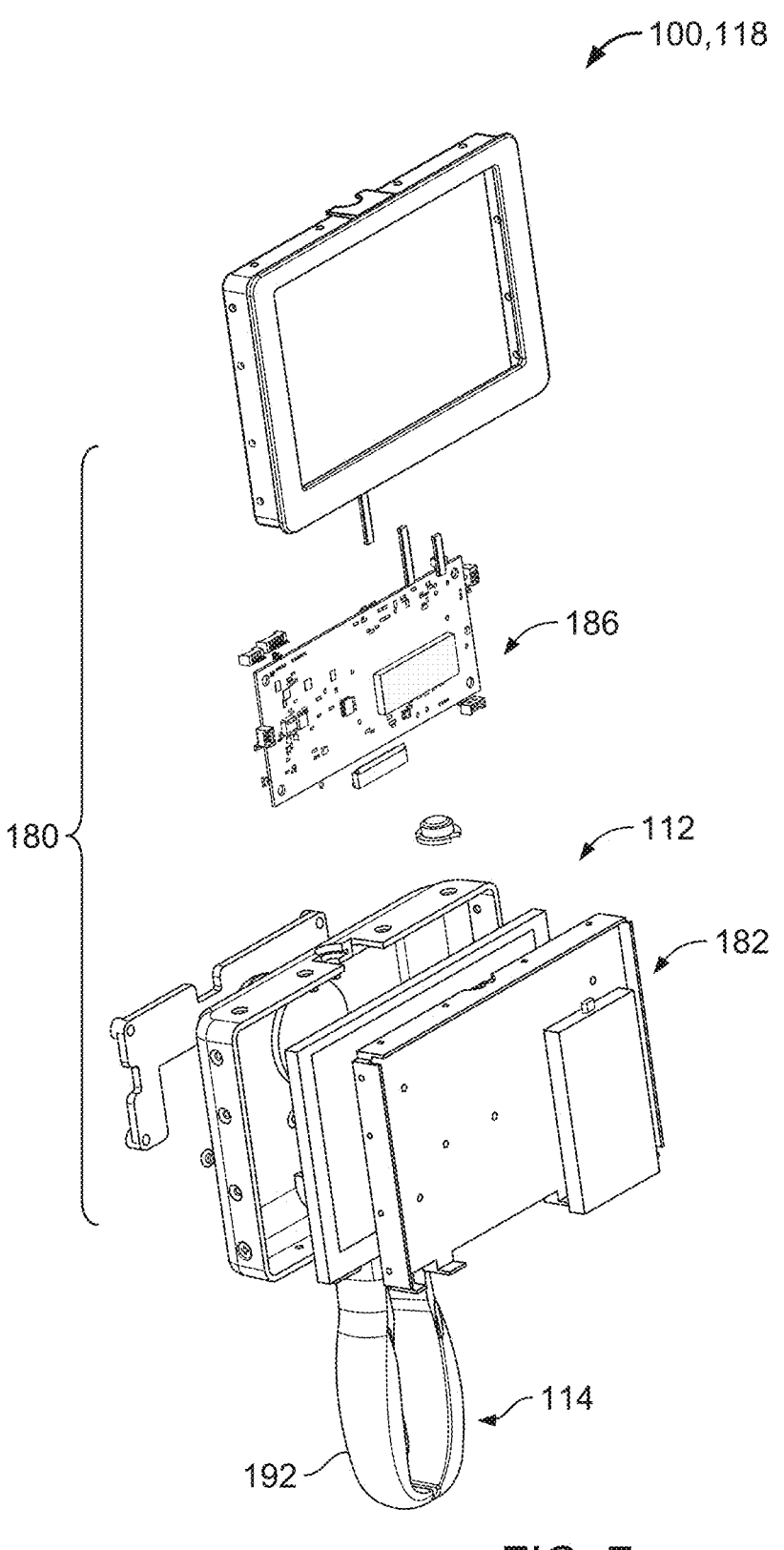
FIG. 7 is an exploded perspective view of the reusable portion of FIG. 6.
Figures 8, 9:
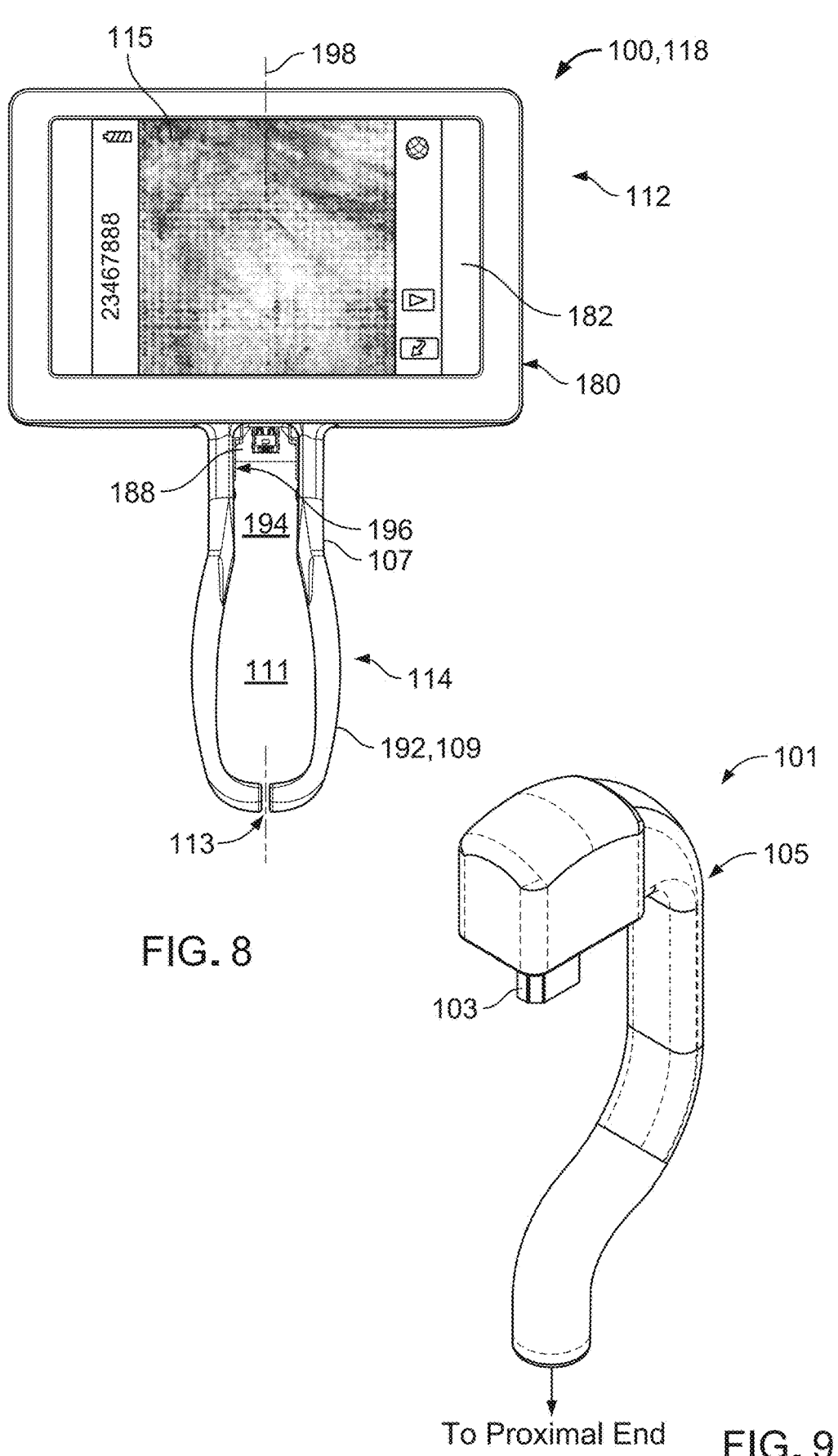
FIG. 8 is a front end view of the reusable portion of FIG. 6.
FIG. 9 is a perspective view of a portion of an extension cable of the endoscopic device of FIG. 1.

Referring to FIGS. 6-8, the display 112 of the endoscopic device 100 includes a housing 180, a screen 182 (e.g., a touchscreen) that presents multiple graphical user interfaces (GUIs) at which a user can manipulate control of the imaging system 104 and other functionalities of the endoscopic device 100, a power control 184 (e.g., a push button) by which the endoscopic device 100 can be turned on and off, internal electronics 186, an electrical connector 188 (e.g., a micro HDMI connector or another type of connector) that mates with the connection port 160 of the connection hub 108 to relay signals between the imaging system 104 and the internal electronics 186, and a magnet 190 by which the display can be secured to a metal support component when the reusable portion 118 of the endoscopic device 100 is detached from the single-use portion 116.

The internal electronics 186 are programmed or otherwise configured to process or manipulate data acquired by the camera 142, to generate GUIs displayed on the screen 182, to transmit data via a wired connection between the display 112 and the imaging system 104, to transmit data wirelessly between the display 112 and other devices (e.g., a computer, a smart phone, or a tablet) that are not mechanically connected to the endoscopic device 100, to power the endoscopic device on and off, and to implement various user-selected settings of the endoscopic device 100. The internal electronics 186 include a microprocessor, a PCB, an ISP, a WiFi module, a battery management circuit, a current monitor circuit, an on board memory (e.g., non-volatile storage memory), a USB interface, and a rechargeable battery with a charging capacity of about 2400 mAh needed to carry out the functionality of the imaging system 104 and other features of the endoscopic device 100. The endoscopic device 100 also includes a docking station (not shown) that is designed to be used with the reusable portion 118 for charging and USB connection.

The electrical connecter 188 serves multiple purposes, including video-out to an external display, connector to an AC adapter for charging the rechargeable battery, and/or as a port to a host PC for downloading and uploading images, video and/or settings, as well as for charging the rechargeable battery. The on board memory is used to accept flash memory cards used to store images, video and/or settings for the endoscopic device 100.

The handle 114 includes two handle portions 192 that extend from a lower surface of the housing 180 of the display 112. The handle portions 192 together define a seating channel 194 adjacent the display 112 at which the reusable portion 118 of the endoscopic device 100 can be slid and snapped onto the single-use portion 116. Substantially straight sections 107 of the handle portions 192 define interior profiles 196 along the seating channel 194 that allow the handle portions 192 to mate with and be secured to the receptacles 170 and the detents 172 on the proximal portion 168 of the connection hub 108. The handle portions 192 further include curved sections 109 that extend and bow outward from the straight sections 107 to define a wider separation channel 111 that further facilitates installation of the reusable portion 118 to the single-use portion 116.

The handle portions 192 are biased to the illustrated nominal position, but have a flexibility that is sufficient to allow the handle portions 192 to be urged apart from each other (e.g., pulled apart by a user or forced apart by the connection hub 108 disposed therebetween) to widen the seating channel 194 to facilitate sliding of the handle 114 onto the connection hub 108. For example, with the seating channel 194 of the handle 114 substantially aligned with the receptacles 170 of the connection hub 108, the single-use portion 116 (e.g., the connection hub 108) of the endoscopic device 100 can be urged through an opening 113 into the separation channel 111 and further towards the seating channel 194 until the interior profiles 196 of the handle portions 192 snap onto the receptacles 170 and the detents 172 in a spring-like manner according to the biased, nominal position of the handle portions 192.

The housing 180 of the display 112 typically has a length of about 11 cm to about 15 cm (e.g., about 13 cm), a width of about 7 cm to about 9 cm (e.g., about 8 cm), and a height of about 2 cm to about 4 cm (e.g., about 3 cm). The screen 180 typically has a diagonal length of about 11 cm to about 14 cm (e.g., about 12.5 cm). The handle 114 is centered with respect to a central axis 198 of the display 112. In the nominal position of the handle portions 192, the seating channel 194 has a width of about 14 cm to about 18 cm (e.g., about 16 cm), the separation channel 111 has a width of about 20 cm to about 30 cm (e.g., about 25 cm), and the handle portions 192 are spaced apart from each other by a distance of about 2 cm to about 4 cm (e.g., about 3 cm) at their free ends (e.g., at the opening 113). Referring particularly to FIG. 2, the reusable portion 118 of the endoscopic device 100 is typically oriented at an angle of about 80° to about 100° (e.g., about 90°) with respect to the single-use portion 116 of the endoscopic device, as measured between the primary axis 122 of the cannula 102 and the central axis 198 of the display 112.

In some embodiments, the handle 114 and the housing 180 of the display 112 are formed as a unitary, integrated component. The handle 114 and the housing 180 of the display 112 are typically made of one or more materials, such as ABS or polycarbonate or copolyester that can chemically withstand various, standard disinfecting solutions. The handle 114 and the housing 180 are typically manufactured via injection molding.

In some implementations, the reusable portion 118 of the endoscopic device 100 is attached to the single-use portion 116 at the connection hub 108 (e.g., at the connection port 160 and along the housing 146) prior to inserting the cannula 102 into the patient. In such cases, a user can view images acquired by the imaging system 104 on the screen 182 of the display 112 as the cannula 102 is advanced into the patient, and the handle 114 provides a pistol-type grip by which the user can grasp and manipulate the endoscopic device 100.

In some implementations, the reusable portion 118 of the endoscopic device 100 is not connected to the single-use portion 116 while the cannula 102 is inserted into the patient. In such cases, the reusable portion 118 can be located (e.g., mounted to an adjustable holding structure via the magnet 190 within a viewing region of a user and can be in wireless communication with the imaging system 104, such that the user can view images acquired by the imaging system 104 on the screen 182 of the display 112 as the cannula 102 is advanced into the patient. Additionally, the housing 146 of the connection hub 108 provides a handle by which the user can grasp and manipulate the single-use portion 116 of the endoscopic device 100. With a weight, a bulk, and a moment arm of the reusable portion 118 removed from the single-use portion 116, a user may be able to more easily and freely insert the cannula 102 into the patient (e.g., as compared to insertion of the cannula 102 with the reusable portion 118 attached to the single-use portion 116) while maintaining an ability to visualize the cervix and the uterus on the screen 182 as the cannula 102 is inserted into the patient.

In some implementations, the reusable portion 118 of the endoscopic device 100 is connected to the single-use portion 116 at the connection port 160 by an extension cable 101 (e.g., a display cable) prior to inserting the cannula 102 into the patient. Referring to FIG. 9, a distal connector 103 of the extension cable 101 can be attached to the connection port 160, a hook portion 105 of the extension cable 101 can be situated to clear the single-use portion 116 (e.g., in a manner such that the hook portion 105 avoids contact with the single-use portion so as not to obstruct manipulation of the single-use portion), and the display 112 can be attached to a proximal end of the extension cable 101 within a viewing region of the user. Accordingly, a user can view images acquired by the imaging system 104 on the screen 180 of the display 112 as the cannula 102 is advanced into the patient. Similar to a wireless configuration of the display 112, with a weight, a bulk, and a moment arm of the reusable portion 118 removed from the single-use portion 116, a user may be able to more easily and freely insert the cannula 102 into the patient (e.g., as compared to insertion of the cannula 102 with the reusable portion 118 attached to the single-use portion 116) while maintaining an ability to visualize the cervix and the uterus on the screen 182 as the cannula 102 is inserted into the patient.

Referring to FIG. 10, a method (200) of using an endoscopic device 100 to perform a hysteroscopic procedure for examining a patient's uterus initially involves obtaining a single-use portion 116 and a reusable portion 118. A single-use portion 116 of an endoscopic device 100 is removed from a sterile package, and a reusable portion 118 is cleaned and disinfected (or examined for existing cleanliness and sterilization) according to standard disinfection practices for use in the hysteroscopic procedures. The single-use portion 116 is communicated with the reusable portion (e.g., either attached directly to the reusable portion 118 at the connection port 160 and the electrical connector 188, connected to the reusable portion 118 via the extension cable 101, or positioned separately from the reusable portion 118 and wirelessly communicated with the reusable portion 118) (202).

Once the single-use portion 116 is communicated with the reusable portion 118 (e.g., either in a wired or wireless manner), the cannula 102 is inserted through the cervix and into the uterus (204), while fluid optionally flows out of the luminal opening 132 and into the patient ahead of the distal tip 106 of the cannula 102. Once the distal tip 106 of the cannula 102 is positioned as desired within the uterus, the user visually examines the uterine tissues by viewing live images 115 on the screen 182 of the display 112 (206). Furthermore, the user can optionally insert a working instrument through the operative conduit 156 and the distal tip 106 to perform a surgery on the uterus. The user can optionally press either of the push buttons 176 on the connection hub 108 to capture imaging data (e.g., still photos or video recordings and any associated metadata). Once the user has finished visually examining the uterus, performing any desired surgeries, and capturing any desired photos and videos, the user withdraws the cannula 102 from the patient (208).

Next, the single-use portion 116 is disconnected from the reusable portion 118 (if the portions 116, 118 were attached to each other), and the single-use portion 116 is disposed of (210). Any captured imaging data can be shown or replayed on the screen 182 of the display 112 using the various GUIs generated by the internal electronics 186 of the display 112. The imaging data can be shown or replayed while the cannula 102 is inserted within the patient 102 or after withdrawing the cannula 102 from the patient. A standard cleaning procedure is performed on the reusable portion 118. The display 112 can then be docked to a base station for battery recharging and/or for transferring images and patient information out of the display to other storage/processing components. The images and patient information can also be transferred wirelessly to another device, irrespective of docking to a base station.

Referring to FIG. 11, the internal electronics 186 of the display 112 can generate a home screen 300 that presents several user-selectable options, including a "start" option 302, a "preview" option 304, a "playback" option 306, and a "setup" option 308. The "start" option 302 allows a user to provide an alphanumeric identification string or barcode scan (e.g., using the camera 142) to be associated with a new patient. The preview option 304 allows a user to view a live video feed acquired by the camera 142 and to capture still photos and video recordings from the live video feed. The playback option 306 allows a user to show or replay stored, still photos and video recordings captured by the camera 142. The setup option 308 allows a user to set various features of the endoscopic device 100, such as a system clock, a video out format, and a memory card format.

Figure 12:
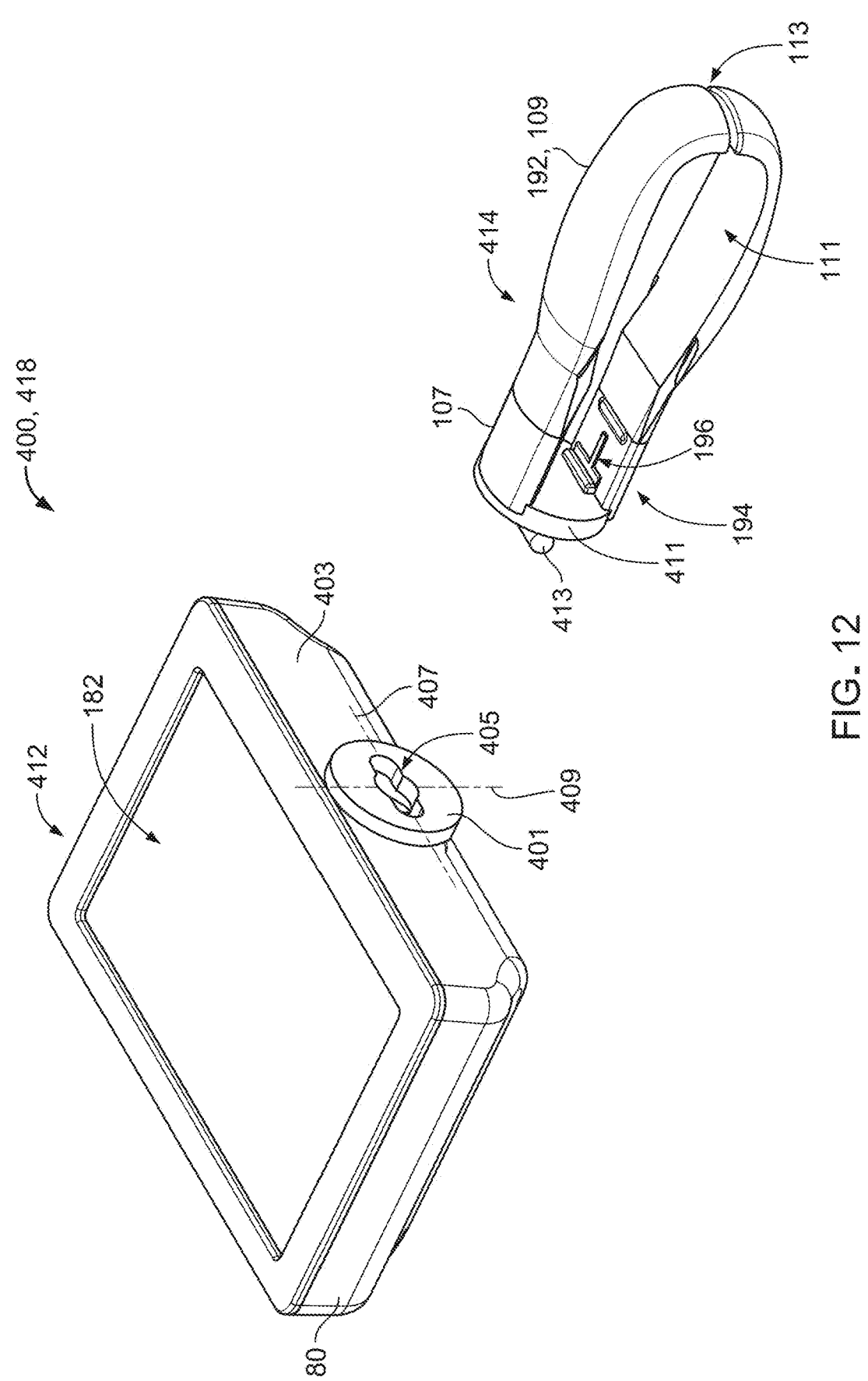
FIG. 12 is a perspective view of a reusable portion of an endoscopic device, including a separable display and handle.

While the endoscopic device 100 has been described and illustrated as including a display 112 and a handle 114 that are permanently attached to each other (e.g., inseparable from each other), in some embodiments, an endoscopic device includes a display and a handle that are detachable from each other. For example, FIGS. 12 and 13 illustrate a reusable portion 418 of an endoscopic device 400 that is substantially similar in construction and function to the endoscopic device 100, except that the endoscopic device 400 includes a display 412 and a handle 414 that are separable from each other. Accordingly, the endoscopic device 400 also includes the reusable portion 116 of the endoscopic device 100, as described above with respect to FIGS. 1-5.

The display 412 is substantially similar in construction and function to the display 112 of the endoscopic device 100, except that the display 412 includes an attachment plate 401 at which the display 412 can be attached to and detached from the handle 414. Accordingly, the display 412 includes the housing 180, the screen 182, the power control 184, the internal electronics 186, the electrical connector 188 (omitted from the figures for clarity), and the magnet 190. The attachment plate 401 is positioned along a lower surface 403 of the housing 180 and defines a slot 405. The slot 405 includes a major axis 407 at which the slot 405 has a relatively large length and a relatively small width, as well as a minor axis 409 at which the slot 405 has a relatively small length and a relatively large width. The slot 405 typically has a length (e.g., along the major axis 407) of about 0.10 cm to about 0.28 cm (e.g., about 0.18 cm) and a width (e.g., along the minor axis 409) of about 0.2 cm to about 0.6 cm (e.g., about 0.4 cm).

The handle 414 is substantially similar in construction and function to the handle 114 of the endoscopic device 100, except that the handle 414 includes an attachment plate 411 at which the handle 414 can be attached to and detached from the display 412. Accordingly, the handle 414 includes the handle portions 192 that define the seating channel 194, the interior profile 196, and the separation channel 111. The attachment plate 411 defines an upper portion of the handle 414 and defines a connection member 413. The connection member 413 is formed as an elongate bar that is sized to pass through the slot 405 along the major axis 407. The connection member 413 has a length that is smaller than the length of the slot 405 along the major axis 407, but longer than the width of the slot 405 along the minor axis 409. The attachment plates 401, 411 are made of one or more materials including ABS or polycarbonate or copolyester.

To attach the handle 414 to the display 412, the connection member 413 can be inserted into the slot 405 and past a wall of the housing 180 (e.g., to clear the wall) so that the handle 414 can be turned by about 90° to retain the connection member 413 within the housing 180 along the minor axis 409 of the slot 405. In the rotated position, the connection member 413 is prevented from passing through the slot 405, such that the handle 414, owing to a frictional fit between the connection member 413 and an internal cavity of the attachment plate 401, is secured to the display 414 in an orientation at which the receptacles 170 of the connection hub 108 can mate with the interior profiles 196 of the handle portions 192 (e.g., as the handle 114 is illustrated in FIG. 8). To detach the handle 414 from the display 412, the handle 414 can be rotated again by about 90° from the secured position to align the connection member 413 with the major axis 407 of the slot 405, such that the handle 414 can be removed (e.g. pulled) from the display 412. The handle 414 can be reattached and detached as desired. In some examples, separation of the display 412 from the handle 414 can facilitate procedures for cleaning and disinfecting the display 412 and the handle 414.

In some implementations, both the display 412 and the handle 414 of the endoscopic device 400 are attached to the single-use portion 116 at the connection hub 108 (e.g., at the connection port 160 and along the housing 146) prior to inserting the cannula 102 into the patient. In such cases, and as discussed above with respect to the reusable portion 118 of the endoscopic device 100, a user can view images acquired by the imaging system 104 on the screen 182 of the display 412 as the cannula 102 is advanced into the patient, and the handle 414 provides a pistol-type grip by which the user can grasp and manipulate the endoscopic device 400.

In some implementations, the display 412 of the endoscopic device 400 is not connected to the single-use portion 116 (e.g., and the handle 414 is attached or unattached to the single-use portion 116) while the cannula 102 is inserted into the patient. In such cases, the display 412 can be located (e.g., mounted to an adjustable holding structure) within a viewing region of a user and can be in wireless communication with the imaging system 104, such that the user can view images acquired by the imaging system 104 on the screen 182 of the display 412 as the cannula 102 is advanced into the patient. Additionally, the housing 146 of the connection hub 108 provides a handle by which the user can grasp and manipulate the single-use portion 116 of the endoscopic device 400. As discussed above with respect to the endoscopic device 100, with a weight, a bulk, and a moment arm of the reusable portion 418 removed from the single-use portion 116, a user may be able to more easily and freely insert the cannula 102 into the patient (e.g., as compared to insertion of the cannula 102 with the reusable portion 418 attached to the single-use portion 116) while maintaining an ability to visualize the cervix and the uterus on the screen 182 as the cannula 102 is inserted into the patient.

In some implementations, the display 412 of the endoscopic device 400 is connected to the single-use portion 116 at the connection port 160 by the extension cable 101 prior to inserting the cannula 102 into the patient, as discussed above with respect to FIG. 9. Accordingly, a user can view images acquired by the imaging system 104 on the screen 180 of the display 412 as the cannula 102 is advanced into the patient. With the display 412 connected to the single-use portion 116 by the extension cable 101, the handle 414 may be attached or unattached to the connection hub 108 of the single-use portion 116. If the handle 414 is attached to the connection hub 108, the handle 414 provides a pistol-type grip by which the user can grasp and manipulate the single-use portion 116 of the endoscopic device 400. Similar to a wireless configuration of the display 412, with a weight, a bulk, and a moment arm of the display 412 (e.g., and/or the handle 414) removed from the single-use portion 116, a user may be able to more easily and freely insert the cannula 102 into the patient (e.g., as compared to insertion of the cannula 102 with the reusable portion 418 attached to the single-use portion 116) while maintaining an ability to visualize the cervix and the uterus on the screen 182 as the cannula 102 is inserted into the patient.

In some embodiments, the handle 414, while attachable to and detachable from the display 412, may be a single-use handle or a multiple-use handle that, together with the reusable display 412, forms a multiple-use portion of the endoscopic device 400.

Figure 14:
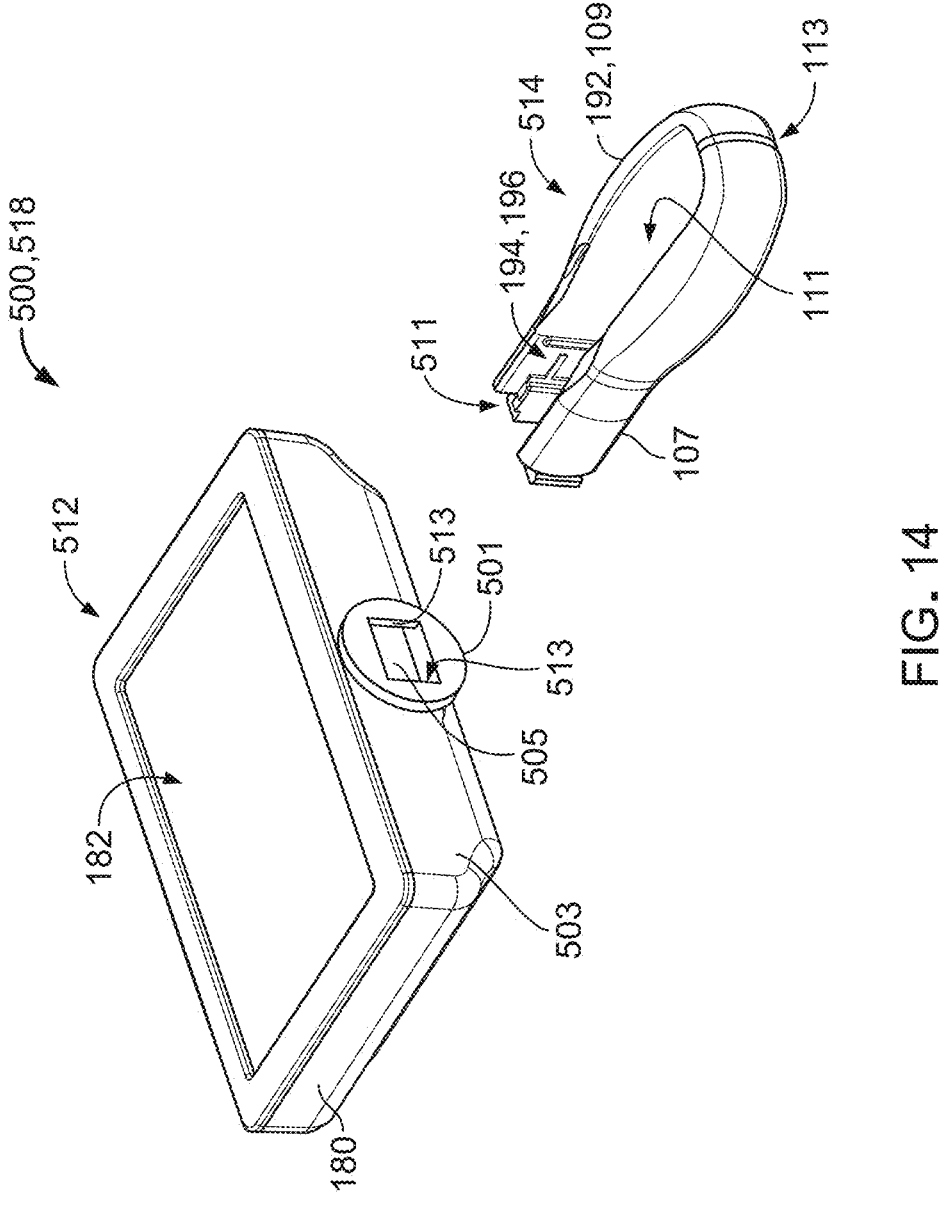
FIG. 14 is a perspective view of a reusable portion of an endoscopic device, including a separable display and handle.
Figure 15:
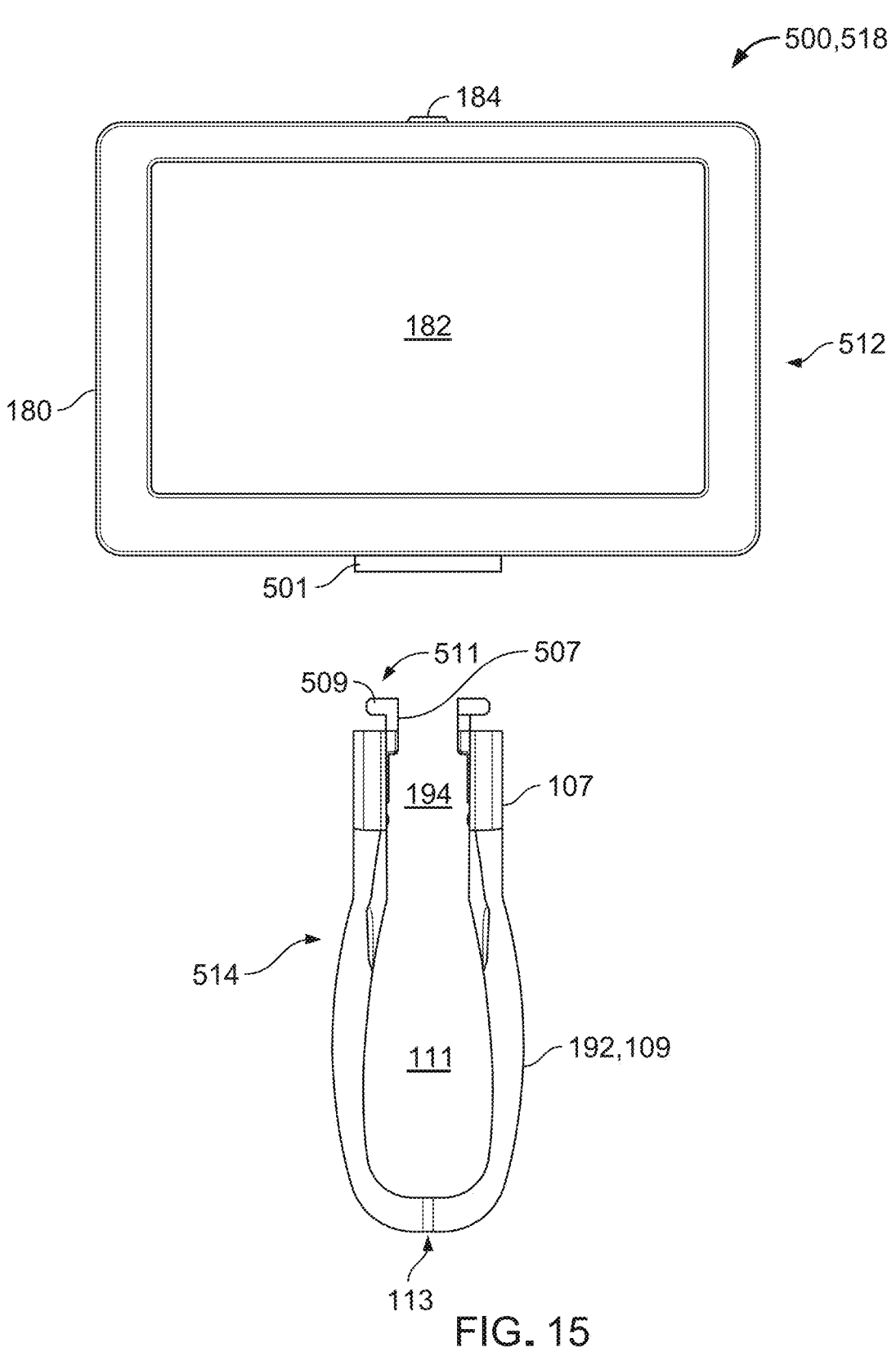
FIG. 15 is a front view of the reusable portion FIG. 14.

While the endoscopic device 400 has been described and illustrated as including a slot and bar mechanism for connecting and disconnecting the display 412 and the handle 414, in some embodiments, an endoscopic device includes a slot and flange mechanism for connecting and disconnecting a display and a handle. For example, FIGS. 14 and 15 illustrate a reusable portion 518 of an endoscopic device 500 that is substantially similar in construction and function to the endoscopic device 100, except that the endoscopic device 500 includes a display 512 and a handle 514 that are separable from each other. Accordingly, the endoscopic device 500 also includes the reusable portion 116 of the endoscopic device 100, as described above with respect to FIGS. 1-5.

The display 512 is substantially similar in construction and function to the display 112 of the endoscopic device 100, except that the display 512 includes an attachment plate 501 at which the display 512 can be attached to and detached from the handle 514. Accordingly, the display 512 includes the housing 180, the screen 182, the power control 184, the internal electronics 186, the electrical connector 188 (omitted from the figures for clarity), and the magnet 190. The attachment plate 501 is positioned along a lower surface 503 of the housing 180 and defines a square-shaped opening 505. The opening 505 typically has a length (e.g., extending between lateral edges 513) of about 1 cm to about 3 cm (e.g., about 2 cm) and a width of about 1.5 cm to about 3.5 cm (e.g., about 2.5 cm).

The handle 514 is substantially similar in construction and function to the handle 114 of the endoscopic device 100, except that the handle 514 includes two flanges 511 at which the handle 514 can be attached to and detached from the display 512. Accordingly, the handle 514 includes the handle portions 192 that define the seating channel 194, the interior profile 196, and the separation channel 111. The flanges 511 have an L-shape construction that is sized to be inserted within the opening 505. Each flange 511 includes a projection 507 that extends from a handle portion 192 and lip 509 that extends (e.g., overhangs) from each projection 507. The lips 509 define a total (e.g., end to end) length that is longer than the length of the opening 405. The attachment plate 501 and the flanges 511 are made of one or more materials including ABS or polycarbonate or copolyester. To attach the handle 514 to the display 512, the handle 514 is oriented with respect to the display 512 as shown in FIG. 15 and then moved towards the display 512 to position the flanges 511 in proximity to the opening 505. The handle 514 is tilted laterally to insert one of the lips 509 within the opening 505 in a manner such that the lip 509 is seated against a respective edge 513. In this configuration, the opposite lip 509 can be moved inside of the opening 505, and the handle 514 can be adjusted laterally such that both lips 509 are secured within the opening 505 against the respective lateral edges 513. To detach the handle 514 from the display 512, the handle 514 can be tilted laterally again until the lips 509 can be sequentially pulled from the opening 505 to remove the handle 514 from the display 512. The handle 514 can be reattached and detached as desired. In some examples, separation of the display 512 from the handle 514 can facilitate procedures for cleaning and disinfecting the display 512 and the handle 514.

As discussed above with respect to the endoscopic device 400, both the display 512 and the handle 514 of the endoscopic device 500 can be attached to the single-use portion 116 at the connection hub 108 (e.g., at the connection port 160 and along the housing 146) prior to inserting the cannula 102 into the patient, the display 512 can be unattached to (e.g., and in wireless communication with) the single-use portion 116 (e.g., with the handle 514 attached to or unattached to the single-use portion 116) while the cannula 102 is inserted into the patient, or the display 512 can be connected to the single-use portion 116 at the connection port 160 by the extension cable 101 prior to inserting the cannula 102 into the patient (e.g., with the handle 514 attached to or unattached to the single-use portion 116).

In some embodiments, the handle 514, while attachable to and detachable from the display 512, may be a single-use handle or a multiple-use handle that, together with the reusable display 512, forms a multiple-use portion of the endoscopic device 500.

Figure 16:
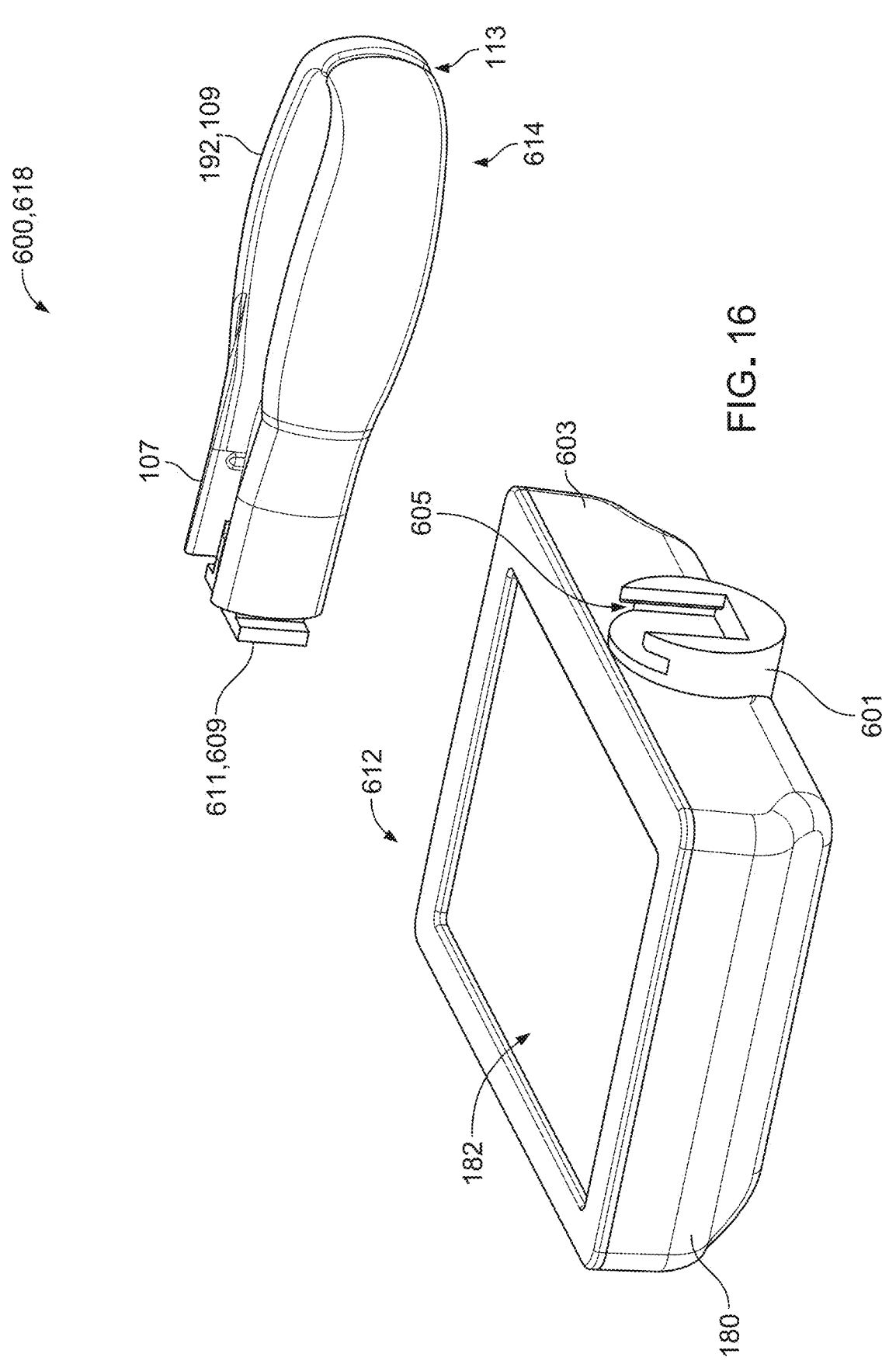
FIG. 16 is a perspective view of a reusable portion of an endoscopic device, including a separable display and handle.
Figures 17, 18:
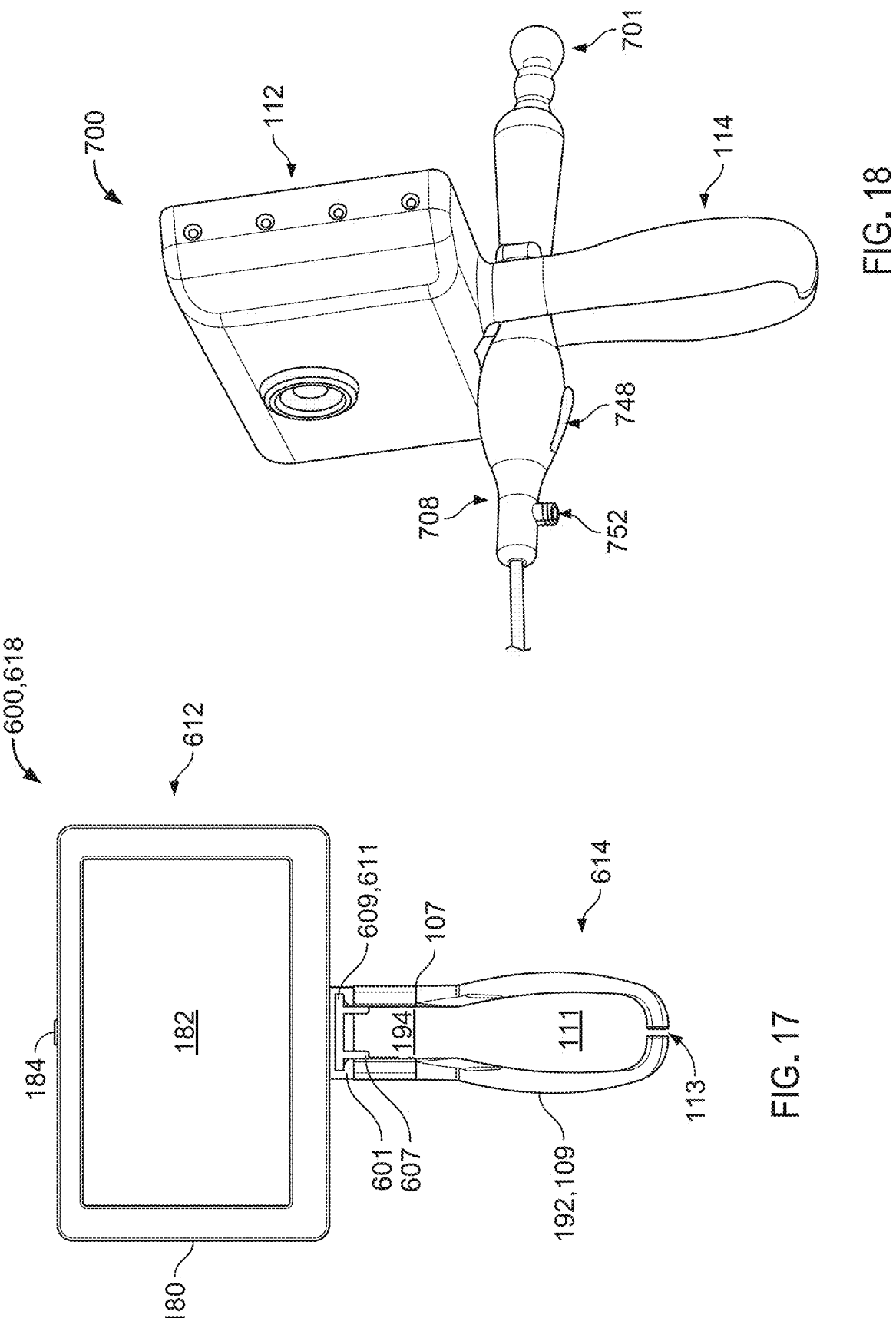
FIG. 17 is a front view of the reusable portion FIG. 16.
FIG. 18 is a perspective view of an endoscopic device including a camera push button along an underside of a connection hub.

FIGS. 16 and 17 illustrate a reusable portion 618 of an endoscopic device 600 that includes a sliding slot and flange mechanism. The endoscopic device 600 is substantially similar in construction and function to the endoscopic device 100, except that the endoscopic device 600 includes a display 612 and a handle 614 that are separable from each other. Accordingly, the endoscopic device 600 also includes the reusable portion 116 of the endoscopic device 100, as described above with respect to FIGS. 1-5.

The display 612 is substantially similar in construction and function to the display 112 of the endoscopic device 100, except that the display 612 includes an attachment plate 601 at which the display 612 can be attached to and detached from the handle 614. Accordingly, the display 612 includes the housing 180, the screen 182, the power control 184, the internal electronics 186, the electrical connector 188 (omitted from the figures for clarity), and the magnet 190. The attachment plate 601 is positioned along a lower surface 603 of the housing 180 and defines a channel 605. The channel 605 typically has an internal length of about 1 cm to about 3 cm (e.g., about 2 cm) and an internal depth of about 1 cm to about 3 cm (e.g., about 2 cm).

The handle 614 is substantially similar in construction and function to the handle 114 of the endoscopic device 100, except that the handle 614 includes a flange 611 at which the handle 614 can be attached to and detached from the display 612. Accordingly, the handle 614 includes the handle portions 192 that define the seating channel 194, the interior profile 196, and the separation channel 111. The flange 611 has a prong-like construction that is sized to be slid within the channel 605. The flange 611 includes two projections 607 that extend from the handle portions 192 and an attachment lip 609 that overhangs both projections 607 in opposite directions. The attachment lip 609 has a total (e.g., end to end) length and a thickness appropriately sized to be slidable within the channel 605. The attachment plate 601 and the flange 611 are made of one or more materials including ABS or polycarbonate or copolyester.

To attach the handle 614 to the display 612, the handle 614 is oriented with respect to the display 612 as shown in FIG. 17 and then moved towards the display 612 to position the flange 611 in proximity to the channel 605. The flange 611 is slid into the channel 605 until a rear surface of the flange 611 abuts a rear inner surface of the channel 605. The flange 611 is retained within the channel 605 by a frictional fit between the flange 611 and the channel 605. To detach the handle 614 from the display 612, the handle 614 can be pulled (e.g., slid) forward and out of the channel 605 to remove the handle 614 from the display 612. The handle 614 can be reattached and detached as desired. In some examples, separation of the display 612 from the handle 614 can facilitate procedures for cleaning and disinfecting the display 612 and the handle 614.

As discussed above with respect to the endoscopic devices 400, 500, both the display 612 and the handle 614 of the endoscopic device 600 can be attached to the single-use portion 116 at the connection hub 108 (e.g., at the connection port 160 and along the housing 146) prior to inserting the cannula 102 into the patient, the display 612 can be unattached to (e.g., and in wireless communication with) the single-use portion 116 (e.g., with the handle 614 attached to or unattached to the single-use portion 116)

while the cannula 102 is inserted into the patient, or the display 612 can be connected to the single-use portion 116 at the connection port 160 by the extension cable 101 prior to inserting the cannula 102 into the patient (e.g., with the handle 614 attached to or unattached to the single-use portion 116).

In some embodiments, the handle 614, while attachable to and detachable from the display 612, may be a single-use handle or a multiple-use handle that, together with the reusable display 612, forms a multiple-use portion of the endoscopic device 600.

While the endoscopic device 100 has been described and illustrated as including a camera actuator 148 that provides lateral push buttons 176, in some embodiments, an endoscopic device includes a camera push button actuator that is located along an underside of reusable portion. For example, FIG. 18 illustrates a portion of an endoscopic device 700 that is substantially similar in construction and function to the endoscopic device 100, except that the endoscopic device 700 includes a camera actuator 748 that is located along a bottom surface of a connection hub 708. Accordingly, the endoscopic device 700 also includes the cannula 102 and the reusable portion 118 of the endoscopic device 100, as described above with respect to FIGS. 1-8. Furthermore, the connection hub 708 is substantially similar in construction and function to the connection hub 108 of the endoscopic device 100, except that a housing 746 of the connection hub 108 is formed to mate with the camera actuator 148. The camera actuator 748 is formed as an elongate push button that can be easily pressed with one or more of a user's fingers (e.g., the index finger) on the hand that is supporting or inserting the endoscopic device 700 into the patient.

As shown in FIG. 18, an adapter 701 can also be attached to the connection hub 708 for facilitating insertion of a working tool into an internal entry port or connection of a fluidic device to the entry port. Such an adapter 701 can similarly be attached to the connection hub 108 of any of the endoscopic devices discussed above or any of the endoscopic devices discussed below.

While the endoscopic devices 100, 400, 500, 600, 700 have been described and illustrated as including embodiments of reusable handles 114, 414, 514, 614, in some embodiments, an endoscopic device includes a single-use, disposable handle. For example, FIGS. 19-23 illustrate various portions of an endoscopic device 800 that includes a single-use handle 814. The endoscopic device 800 is similar in construction and function to the above-discussed endoscopic devices and accordingly includes the cannula 102, the imaging system 104 (e.g., with the exception of the camera actuator 148), a connection hub 808, the handle 814, and a reusable display 812.

The connection hub 808 surrounds the proximal end region 110 of the cannula 102 and serves as a mounting piece for the handle 814. The connection hub 808 also provides several features for fluid and electrical communication between the proximal end region 110 of the cannula 102 and the distal tip 106 of the cannula 102. For example, the connection hub 808 includes a housing 846, a camera actuator 848 that interfaces with other components of the imaging system 104 (e.g., and providing two opposite push buttons 876), a fluid port 850 located adjacent the proximal end region 110 of the cannula 102, an internal entry port disposed at a proximal opening 858 of the housing 846, and an internal operative conduit that extends from the proximal end region 110 of the cannula 102 to the entry port.

The housing 846 is generally axially aligned with the primary axis 122 of the cannula 102 and has a generally curved profile that is laterally symmetric. The housing 846 defines a distal opening 862 through which the cannula 102 passes, an opening 854 (e.g., aligned with the sidewall opening 144 of the shaft 120) to which the fluid port 850 is secured, the proximal opening 858, and an upper connection port 860 (e.g., a micro HDMI port or another type of port) to which the display 812 or a display cable can be connected. In this regard, the connection hub 808 also includes electrical components that communicate the camera actuator 848 with the connection port 860. The housing 846 further defines additional internal wall features (e.g., flanges, openings, brackets, tabs, channels etc.) that properly position the fluid port 850, the camera actuator 848, the connection port 860, and the entry port.

Figures 19, 20:
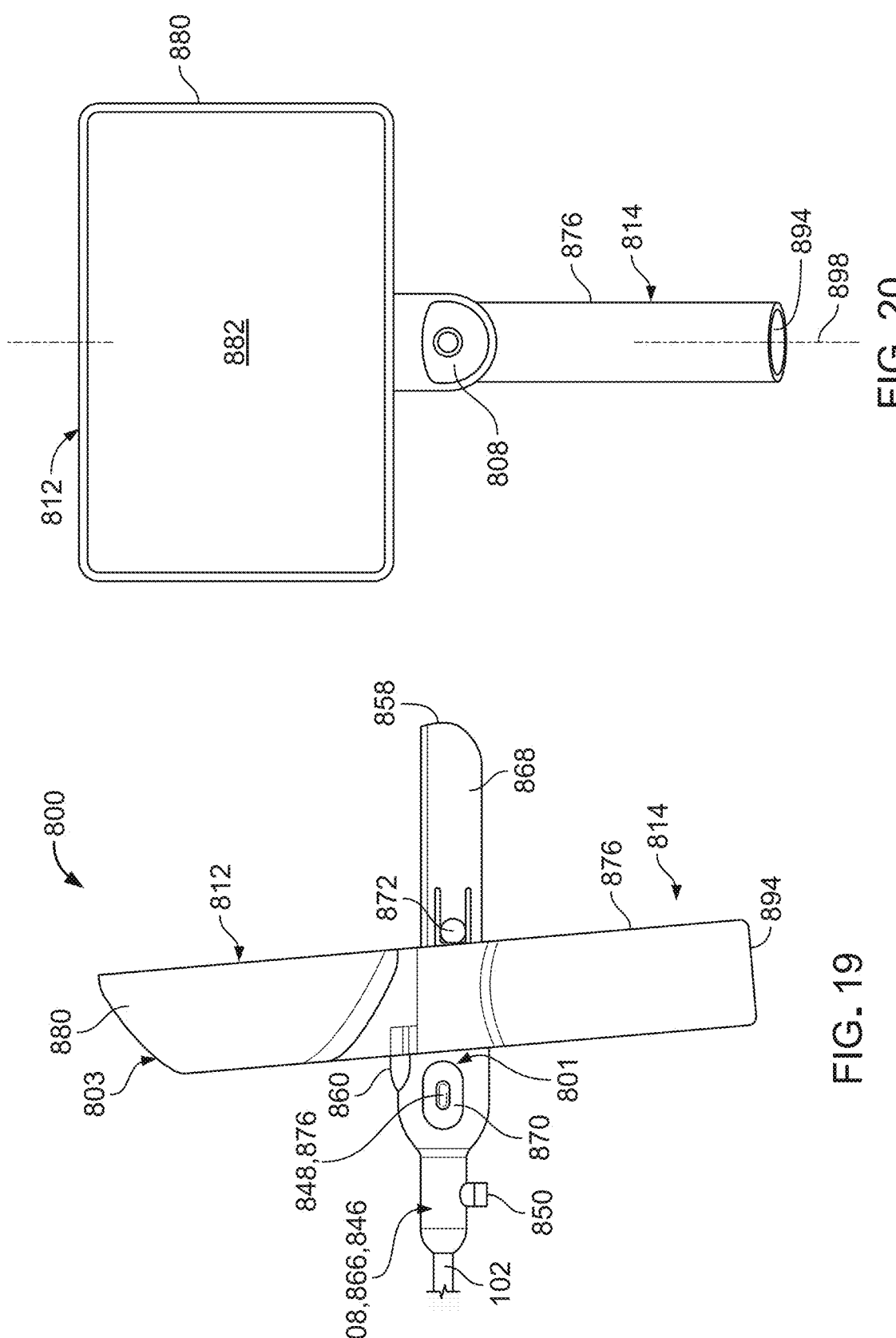
FIG. 19 is a side view of a portion of an endoscopic device including a single-use handle.
FIG. 20 is a front view of the endoscopic device of FIG. 19.

Referring particularly to FIG. 19, a distal portion 866 of the housing 846 provides fluid communication between the distal tip 106 of the cannula 102 (e.g., at the luminal opening 132) and the fluid port 850 and provides fluid communication between the distal tip 106 and the internal operative conduit (e.g., for further fluid communication to the entry port). The distal portion 866 of the housing 846 further provides electrical communication between the distal tip 106 of the cannula 102 (e.g., at the camera 142) and the camera actuator 848, and between the distal tip 106 (e.g., at the camera 142) and the display 812 (e.g., via the connection port 860). The distal portion 866 defines two receptacles 870 surrounding the push buttons 876 to facilitate location of the push buttons 876 with a user's fingers. The distal portion 866 further defines a shoulder 801 against which the handle 814 can abut for appropriate positioning of the handle 814.

Figure 21:
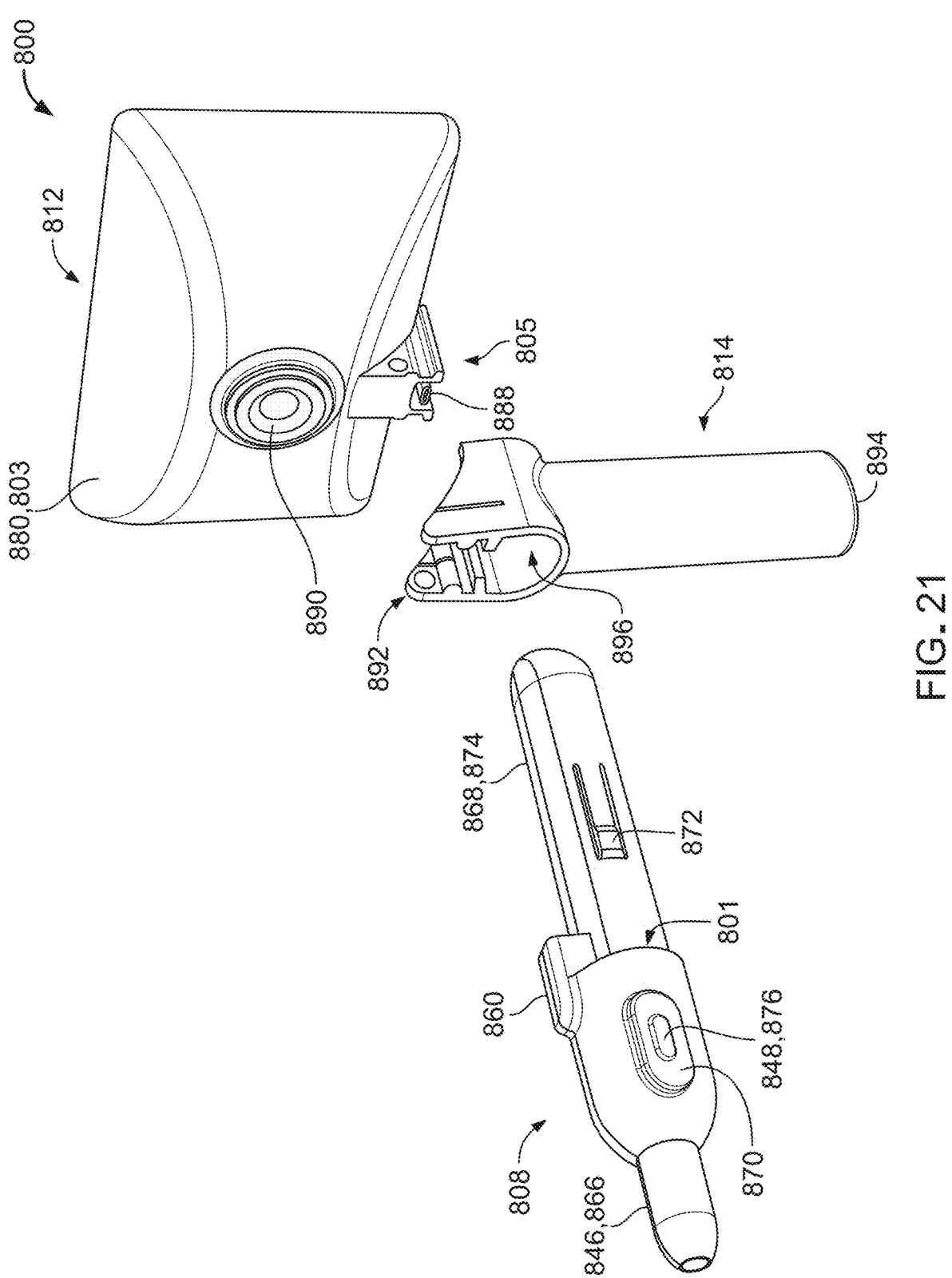
FIG. 21 is an exploded perspective of a portion of the endoscopic device of FIG. 19.

Referring particularly to FIG. 21, a proximal portion 868 of the housing 846 provides two flexible, elongate detents 872 that can secure (e.g., lock) the handle 814 to the connection hub 808, thereby locating the handle 814 (e.g., and the display 812, attached thereto) at a fixed position along the primary axis 122 of the cannula 102. The proximal portion 868 also provides a grip 874 that can be used to manipulate the endoscopic device 800.

The housing 846 of the connection hub 808 typically has a length (e.g., as measured along the primary axis 122 of the cannula 102) of about 10 cm to about 20 cm (e.g., about 15 cm) and a maximum width of about 15 cm to about 40 cm (e.g., about 25 cm). The proximal portion 868 of the housing 846 typically has a width (e.g., a handle seating width) of about 1.4 cm to about 1.8 cm (e.g., about 1.6 cm). The housing 846 is typically made of one or more materials including ABS or polycarbonate or copolyester and is typically manufactured via injection molding. The fluid port 850, the internal operative conduit, and the entry port are substantially similar in construction and function to the fluid port 150, the operative conduit 156, and the entry port 152 described above with respect to the endoscopic device 100.

The display 812 is similar in construction and function to the display 112 of the endoscopic device 100. Accordingly, the display 812 includes a housing 880, a screen 882 (e.g., a touchscreen) that presents multiple GUIs at which a user can manipulate control of the imaging system 104 and other functionalities of the endoscopic device 800, a power control 884 (e.g., a push button, shown in FIG. 23) by which the endoscopic device 100 can be turned on and off, the internal electronics 186, an electrical connector 888 (e.g., a micro HDMI connector or another type of connector) that mates with the connection port 860 of the connection hub 808 to relay signals between the imaging system 104 and the internal electronics 186, and a magnet 890. The power control 884 is positioned along a rear surface 803 of the housing 880 in order to reduce the risk of accidental actuation during use of the endoscopic device 800.

The display 812 also includes an attachment piece 805 that is formed to mate with the connection hub 808 and the handle 814. For example, the attachment piece 805 defines two flanges 807 and two receptacles 809 that are located on opposite sides of the attachment piece 805 and that are formed to engage the handle 814. The attachment piece 805 also includes an electrical connector 888 (e.g., a sheltered connector) that is formed to engage (e.g., slide over and mate with) the connection port 860 of the connection hub 808.

The housing 880 of the display 812 typically has a length of about 11 cm to about 15 cm (e.g., about 13 cm) and a height of about 7 cm to about 9 cm (e.g., about 8 cm). The housing 880 and the attachment piece 805 of the display 812 typically have a width of about 2 cm to about 4 cm (e.g., about 3 cm). The screen 882 typically has a diagonal length of about 11 cm to about 14 cm (e.g., about 12.5 cm). Referring particularly to FIG. 19, the display 812 and the handle 814 are typically oriented at an angle of about 80° to about 115° (e.g., about 95°) with respect to the connection hub 808, as measured between the primary axis 122 of the cannula 102 and a central axis 898 of the display 812. The housing 880 of the display 812 is typically made of one or more materials that can chemically withstand various sterilization solutions and procedures, such as polycarbonate or copolyester or ABS. The housing 880 is typically manufactured via injection molding.

In some embodiments, the handle 814 is designed to be disposed of after examination of a single patient's uterus. The handle 814 includes a gripping member 876 and an attachment piece 892 that is formed to mate with the connection hub 808 and the display 812. The gripping member 876 is an elongate, substantially tubular member that has a rounded (e.g., elliptical) cross-sectional shape and an open end 894. The attachment piece 892 defines a receptacle 896 by which the handle 814 can be slid along the proximal portion 868 of the connection hub 808 to attach the handle 814 to or remove the handle 814 from the connection hub 808. The attachment piece 892 further defines a channel 811 by which the handle 814 can be attached to or detached from the display 812. In particular, the channel 811 defines two slots 813 and two detents 815 located on opposite sides of the channel 811. The slots 813 and the detents 815 are respectively formed to engage the flanges 807 and the receptacles 809 of the attachment piece 805 of the handle 814.

To attach the handle 814 to the connection hub 808, the receptacle 896 of the attachment piece 892 is slid distally over the proximal portion 868 of the connection hub 808 until the attachment piece 892 passes the elongate detents 872 and abuts the shoulder 801 of the distal portion 866. As the attachment piece 892 is slid along the connection hub 808, the attachment piece 892 depresses the detents 872, which are biased to a position defining a distance that is otherwise wider than the receptacle 896. Once the attachment piece 892 passes the detents 872 to abut the shoulder 801, the detents 872 return (e.g., spring back) to the biased positions to lock the handle 814 in position along the connection hub 808. To detach the handle 814 from the connection hub 808, the detents 872 are manually depressed by a user to allow proximal sliding of the attachment piece 892, and the handle 814 is pulled (e.g., slid) off of the connection hub 808. In some examples, separation of the display 812 from the handle 814 can facilitate procedures for cleaning and disinfecting the display 812 and the handle 814.

The display 812 can be attached to the handle 814 after attaching the handle 814 to the connection hub 808. To attach the display 812 to the handle 814, the flanges 807 of the attachment piece 805 are slid distally into the slots 813 of the attachment piece 892 until the detents 815 snap into the receptacles 896 to secure the display 812 to the handle 814. With the display 812 attached to the handle 814, the display 812 can be electrically communicated with the connection hub 808 by mating the electrical connector 888 to the connection hub 860. To detach the display 812 from either or both of the handle 814 and the connection hub 808, walls 817 of the attachment piece 892 can be spread apart to withdraw the detents 815 from the receptacles 896 so that the display 812 can be pulled (e.g., slid) from either or both of the handle 814 and the connection hub 808.

As discussed above with respect to the endoscopic devices 400, 500, 600, both the display 812 and the handle 814 of the endoscopic device 800 can be attached to the connection hub 808 (e.g., at the connection port 860 and along the housing 846) prior to inserting the cannula 102 into the patient, the display 812 can be unattached to (e.g., and in wireless communication with) the connection hub 808 (e.g., with the handle 814 attached to or unattached to the connection hub 808) while the cannula 102 is inserted into the patient, or the display 812 can be connected to the connection hub 808 at the connection port 860 by a display cable prior to inserting the cannula 102 into the patient (e.g., with the handle 814 attached to or unattached to the connection hub 808).

Referring to FIG. 24, an extension cable 819 (e.g., a display cable) includes a connector 821 that is formed to be slid around the proximal portion 868 of the connection hub 808 and to be secured in position by the detents 872 to mate with the cable port 860.

The extension cable 819 further includes a cable 823 that extends from the connector 821 and that includes a proximal end formed to mate with the electrical connector 888 of the display 812.

Figure 25:
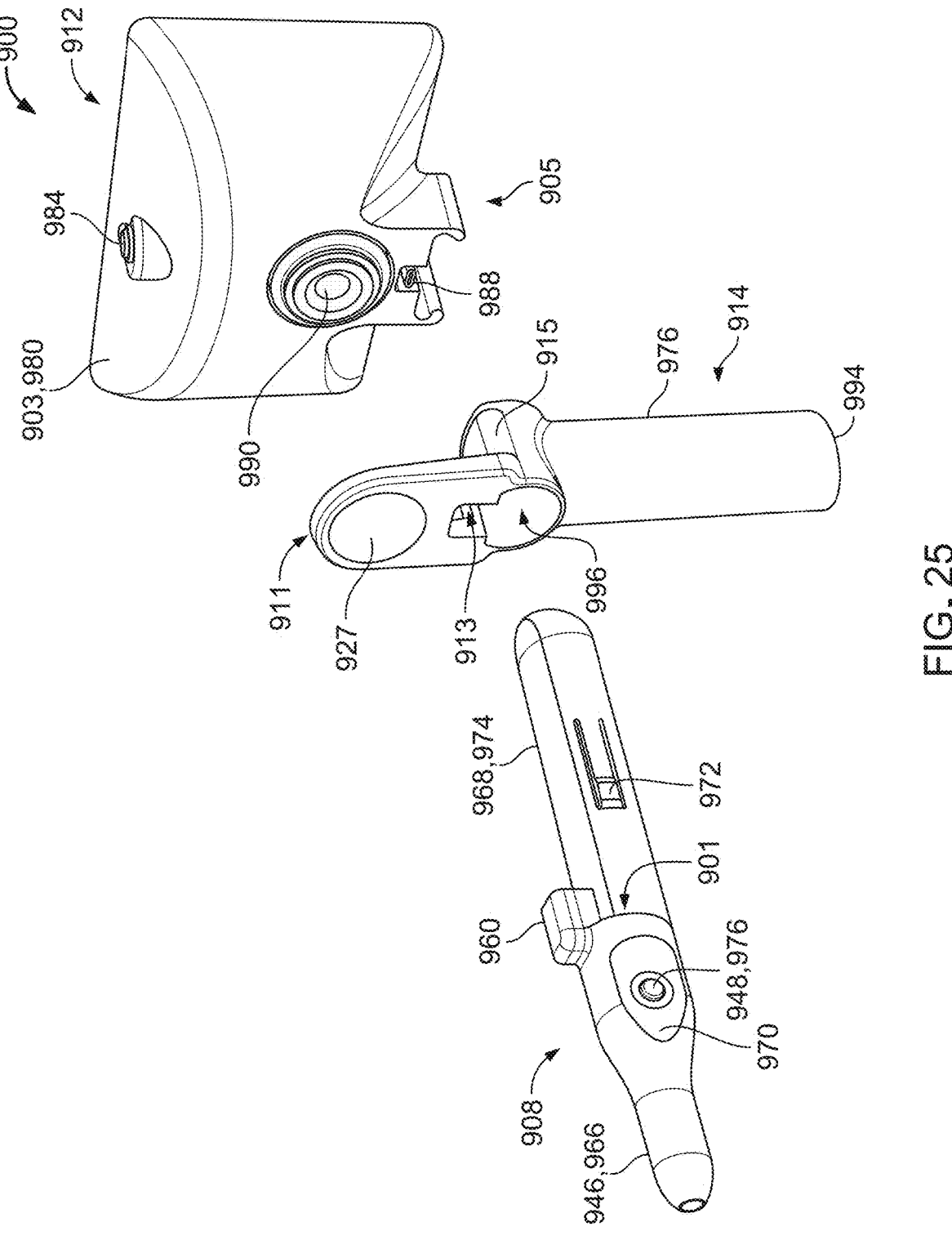
FIG. 25 is an exploded perspective view of a portion of an endoscopic device including a single-use handle.
Figures 26, 27:
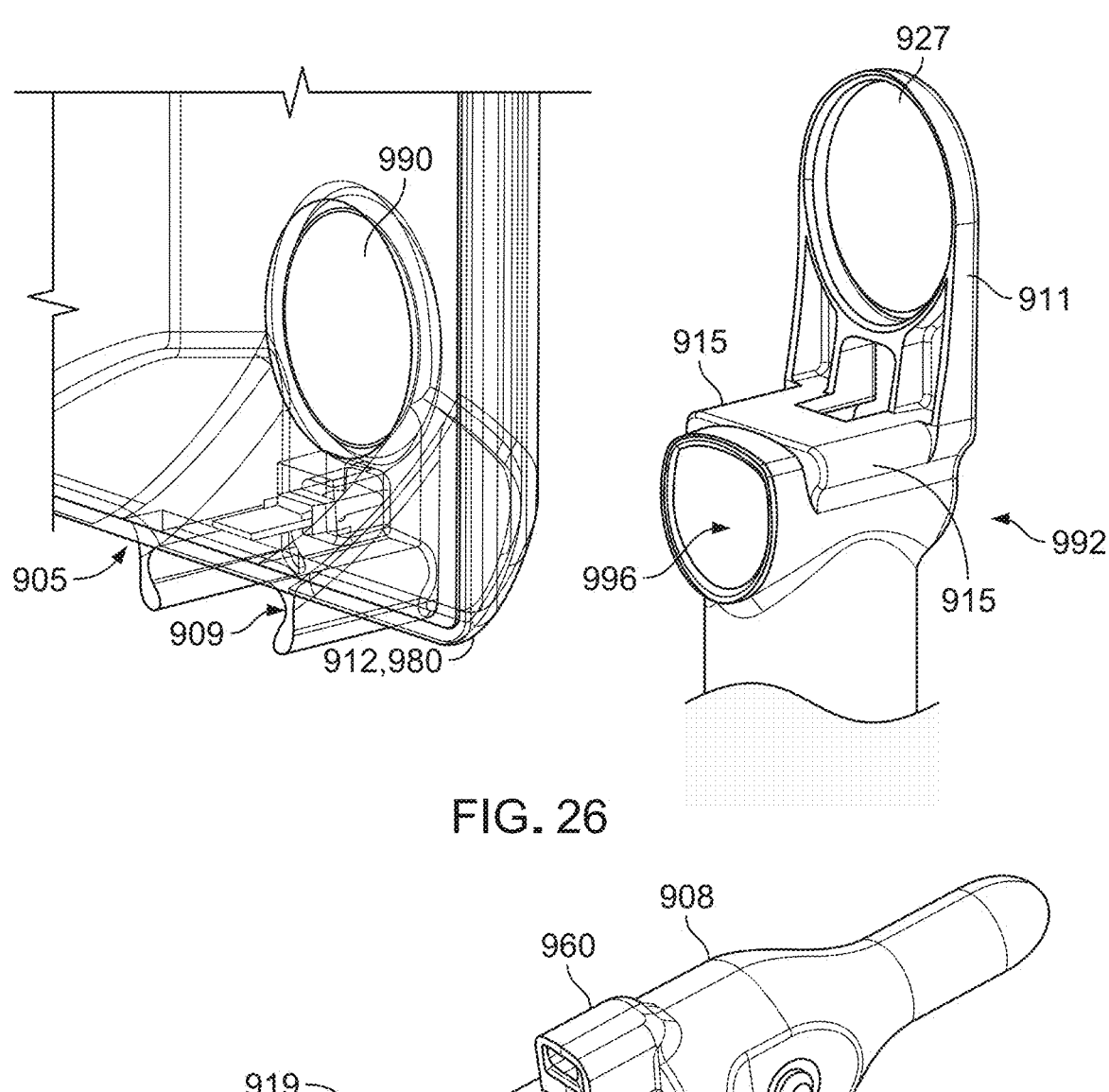
FIG. 26 is an enlarged exploded view of an attachment mechanism of the endoscopic device of FIG. 25.
FIG. 27 is an enlarged perspective view of an extension cable of the endoscopic device of FIG. 25.

While the endoscopic device 800 has been described and illustrated as including a handle and display attachment mechanism that includes slots, flanges, detents, and receptacles, in some embodiments, a handle and display can be releasably attached to each other with a magnetic attachment mechanism. For example, FIGS. 25 and 26 illustrate various portions of an endoscopic device 900 that includes such an attachment mechanism. The endoscopic device 900 is similar in construction and function to the endoscope 800 and accordingly includes the cannula 102, the imaging system 104 (e.g., with the exception of the camera actuator 148), a connection hub 908, a handle 914, and a reusable display 912.

The connection hub 908 surrounds the proximal end region 110 of the cannula 102 and serves as a mounting piece for the handle 914. The connection hub 908 also provides several features for fluid and electrical communication between the proximal end region 110 of the cannula 102 and the distal tip 106 of the cannula 102. For example, the connection hub 908 includes a housing 946, a camera actuator 948 that interfaces with other components of the imaging system 104 (e.g., providing two opposite push buttons 976), a fluid port (not shown) located adjacent the proximal end region 110 of the cannula 102, an internal entry port disposed at a proximal opening 958 of the housing 946, and an internal operative conduit that extends from the proximal end region 110 of the cannula 102 to the entry port.

The housing 946 is generally axially aligned with the primary axis 122 of the cannula 102 and has a generally curved profile that is laterally symmetric. The housing 946 defines a distal opening 962 through which the cannula 102 passes, an opening (e.g., aligned with the sidewall opening 144 of the shaft 120) to which the fluid port is secured, the proximal opening 958, and an upper connection port 960 (e.g., a micro HDMI port or another type of port) to which the display 912 or a display cable can be connected. In this regard, the connection hub 908 also includes electrical components that communicate the camera actuator 948 with the connection port 960. The housing 946 further defines additional internal wall features (e.g., flanges, openings, brackets, tabs, channels etc.) that properly position the fluid port, the camera actuator 948, the connection port 960, and the entry port.

A distal portion 966 of the housing 946 provides fluid communication between the distal tip 106 of the cannula 102 (e.g., at the luminal opening 132) and the fluid port and provides fluid communication between the distal tip 106 and the internal operative conduit (e.g., for further fluid communication to the entry port). The distal portion 966 of the housing 946 further provides electrical communication between the distal tip 106 of the cannula 102 (e.g., at the camera 142) and the camera actuator 948, and between the distal tip 106 (e.g., at the camera 142) and the display 912 (e.g., via the connection port 960). The distal portion 966 defines two receptacles 970 surrounding the push buttons 976 to facilitate location of the push buttons 976 with a user's fingers. The distal portion 966 further defines a shoulder 901 against which the handle 914 can abut for appropriate positioning of the handle 914.

A proximal portion 968 of the housing 946 provides two flexible, elongate detents 972 that can secure (e.g., lock) the handle 914 to the connection hub 908, thereby locating the handle 914 (e.g., and the display 912, attached thereto) at a fixed position along the primary axis 122 of the cannula 102. The proximal portion 968 also provides a grip 974 that can be used to manipulate the endoscopic device 900.

The housing 946 of the connection hub 908 typically has a length (e.g., as measured along the primary axis 122 of the cannula 102) of about 10 cm to about 20 cm (e.g., about 15 cm) and a maximum width of about 15 cm to about 40 cm (e.g., about 25 cm). The proximal portion 968 of the housing 946 typically has a width (e.g., a handle seating width) of about 1.4 cm to about 1.8 cm (e.g., about 1.6 cm). The housing 946 is typically made of one or more materials including ABS or polycarbonate or copolyester and is typically manufactured via injection molding. The fluid port, the internal operative conduit, and the entry port are substantially similar in construction and function to the fluid port 150, the operative conduit 156, and the entry port 152 described above with respect to the endoscopic device 100.

The display 912 is similar in construction and function to the display 812 of the endoscopic device 800, except that the display 912 includes a different mechanism for attachment to the handle 914. Accordingly, the display 912 includes a housing 980, the screen 882, a power control 984 positioned along a rear surface 903 of the housing 980, the internal electronics 186, an electrical connector 988 (e.g., a micro HDMI connector or another type of connector) that mates with the connection port 960 of the connection hub 908 to relay signals between the imaging system 104 and the internal electronics 186, and a magnet 990 that can secure the display 912 to the handle 914.

The display 912 also includes an attachment piece 905 that is formed to mate with the connection hub 908 and the handle 914. For example, the attachment piece 905 defines two receptacles 909 that are located on opposite sides of the attachment piece 905 and that are formed to engage the handle 914. The attachment piece 905 also includes an electrical connector 988 (e.g., a sheltered connector) that is formed to engage (e.g., slide into and mate with) the connection port 960 of the connection hub 908.

The housing 980 of the display 912 typically has a length and a height that are about equal to the length and the height of the housing 880 of the display 812. The housing 980 and the attachment piece 905 of the display 912 typically have a width of about 2 cm to about 4 cm (e.g., about 3 cm). The display 912 and the handle 914 are typically oriented at an angle of about 80° to about 115° (e.g., about 95°) with respect to the connection hub 908, as measured between the primary axis 122 of the cannula 102 and a central axis 998 of the display 912. The housing 980 of the display 912 is typically made of the same materials from which the housing 880 of the display 812 are made, and the housing 980 is typically manufactured the same techniques used to manufacture the housing 880.

In some embodiments, the handle 914 is designed to be disposed of after examination of a single patient's uterus. The handle 914 includes a gripping member 976 and an attachment piece 992 that is formed to mate with the connection hub 908 and the display 912. The gripping member 976 is an elongate, substantially tubular member that has a rounded (e.g., elliptical) cross-sectional shape and an open end 994. The attachment piece 992 defines a receptacle 996 by which the handle 914 can be slid along the proximal portion 968 of the connection hub 908 to attach the handle 914 to or remove the handle 914 from the connection hub 908. The attachment piece 992 further defines two flanges 815 and an extension piece 811 by which the handle 914 can be attached to or detached from the display 912. The extension piece 911 defines a channel 913 through which the electrical connector 988 can pass to mate with the connection port 960. The extension piece also includes a metal component 927 (e.g., a steel disk) that can attract the magnet 990 to secure the display 912 to the handle 914.

To attach the handle 914 to the connection hub 908, the receptacle 996 of the attachment piece 992 is slid distally over the proximal portion 968 of the connection hub 908 until the attachment piece 992 passes the elongate detents 972 and abuts the shoulder 901 of the distal portion 966. As the attachment piece 992 is slid along the connection hub 908, the attachment piece 992 depresses the detents 972, which are biased to a position defining a distance that is otherwise wider than the receptacle 996. Once the attachment piece 992 passes the detents 972 to abut the shoulder 901, the detents 972 return (e.g., spring back) to the biased positions to lock the handle 914 in position along the connection hub 908. To detach the handle 914 from the connection hub 908, the detents 972 are manually depressed by a user to allow proximal sliding of the attachment piece 992, and the handle 914 is pulled (e.g., slid) off of the connection hub 908.

The display 912 can be attached to the handle 914 after attaching the handle 914 to the connection hub 908. To attach the display 912 to the handle 914, the receptacles 909 of the attachment piece 905 are slid distally into the flanges 915 of the attachment piece 992 until the magnet 990 snaps (e.g., due to magnetic attraction) to the metal component 927 to secure the display 912 to the handle 914. With the display 912 attached to the handle 914, the display 912 can be electrically communicated with the connection hub 908 by mating the electrical connector 988 to the connection hub 960. To detach the display 912 from either or both of the handle 914 and the connection hub 908, the display 912 can be pulled (e.g., slid) from either or both of the handle 914 and the connection hub 908. In some examples, separation of the display 912 from the handle 914 can facilitate procedures for cleaning and disinfecting the display 912 and the handle 914.

As discussed above with respect to the endoscopic device 800, both the display 912 and the handle 914 of the endoscopic device 900 can be attached to the connection hub 908 (e.g., at the connection port 960 and along the housing 946) prior to inserting the cannula 102 into the patient, the display 912 can be unattached to (e.g., and in wireless communication with) the connection hub 908 (e.g., with the handle 914 attached to or unattached to the connection hub 908) while the cannula 102 is inserted into the patient, or the display 912 can be connected to the connection hub 908 at the connection port 960 by a display cable prior to inserting the cannula 102 into the patient (e.g., with the handle 914 attached to or unattached to the connection hub 908).

Referring to FIG. 27, an extension cable 919 (e.g., a display cable) includes a connector 921 that is formed to be slid around the proximal portion 968 of the connection hub 908 and to be secured in place by the detents 972 to mate with the cable port 960. The extension cable 919 further includes a cable 923 that extends from the connector 921 and that includes a proximal end formed to mate with the electrical connector 988 of the display 912.

Figures 28, 29:
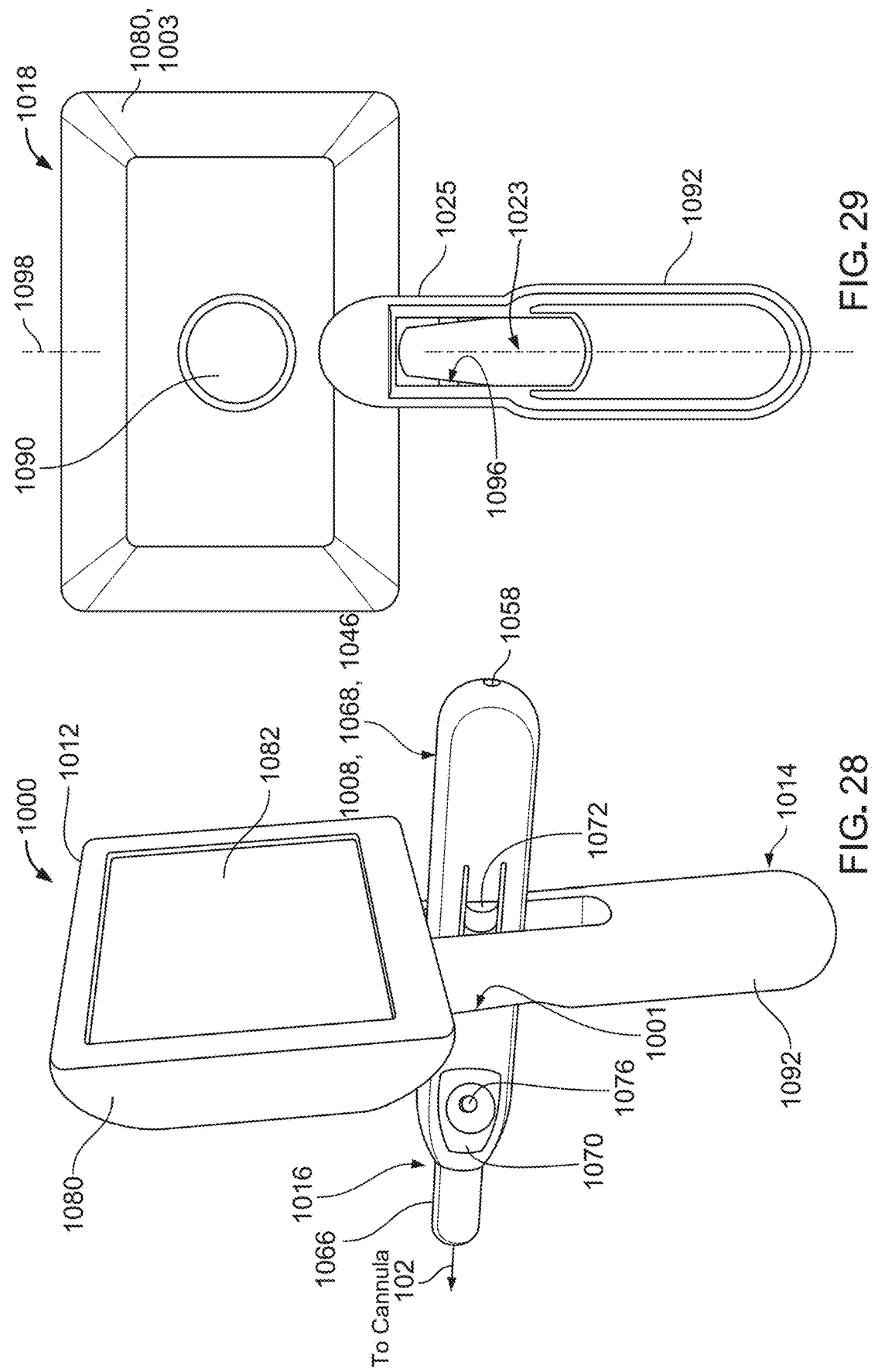
FIG. 28 is a perspective view of a portion of an endoscopic device including a handle that can be slid over a single-use portion of the endoscopic device.
FIG. 29 is a rear view of a reusable portion of the endoscopic device of FIG. 28.

While the endoscopic device 100 has been described and illustrated as including a flexible handle 114 with components that can be urged apart to secure the handle 114 to the connection hub 108, in some embodiments, an endoscopic device includes a rigid handle that can be slid over a connection hub of the endoscopic device to secure a reusable portion of the endoscopic device to a single-use portion of the endoscopic device. For example, FIGS. 28 and 29 illustrate an endoscopic device 1000 that includes a rigid handle 1014. The endoscopic device 1000 is similar in construction and function in several aspects to the above-discussed endoscopes and accordingly includes the cannula 102, the imaging system 104 (e.g., with the exception of the camera actuator 148), a connection hub 1008, the handle 1014, and a display 1012. The cannula 102, the imaging system 104, and the connection hub 1008 together form a single-use portion 1016 of the endoscopic device 1000, while the display 1012 and the handle 1014 together form a reusable portion 1018 of the endoscopic device 1000.

The connection hub 1008 surrounds the proximal end region 110 of the cannula 102 and is sized to pass through a channel 1023 of the handle 1014. The connection hub 1008 also provides several features for fluid and electrical communication between the proximal end region 110 of the cannula 102 and the distal tip 106 of the cannula 102. For example, the connection hub 1008 includes a housing 1046, a camera actuator 1048 (e.g., providing two opposite push buttons 1076), a fluid port (not shown) located adjacent the proximal end region 110 of the cannula 102, an internal entry port disposed at a proximal opening 1058 of the housing 1046, and an internal operative conduit that extends from the proximal end region 110 of the cannula 102 to the entry port.

The housing 1046 is generally axially aligned with the primary axis 122 of the cannula 102 and has a generally curved profile that is laterally symmetric. The housing 1046 defines a distal opening 1062 through which the cannula 102 passes, an opening (e.g., aligned with the sidewall opening 144 of the shaft 120) to which the fluid port is secured, the proximal opening 1058, and an upper connection port 1060 (e.g., a micro HDMI port or another type of port) to which the display 1012 or a display cable can be connected. In this regard, the connection hub 1008 also includes electrical components that communicate the camera actuator 1048 with the connection port 1060. The housing 1046 further defines additional internal wall features (e.g., flanges, openings, brackets, tabs, channels etc.) that properly position the fluid port, the camera actuator 1048, the connection port 1060, and the entry port.

A distal portion 1066 of the housing 1046 provides fluid communication between the distal tip 106 of the cannula 102 (e.g., at the luminal opening 132) and the fluid port and provides fluid communication between the distal tip 106 and the internal operative conduit (e.g., for further fluid communication to the entry port). The distal portion 1066 of the housing 1046 further provides electrical communication between the distal tip 106 of the cannula 102 (e.g., at the camera 142) and the camera actuator 1048, and between the distal tip 106 (e.g., at the camera 142) and the display 1012 (e.g., via the connection port 1060). The distal portion 1066 defines two receptacles 1070 surrounding the push buttons 1076 to facilitate location of the push buttons 1076 with a user's fingers. The distal portion 1066 further defines a shoulder 1001 against which the handle 1014 can abut for appropriate positioning of the handle 1014.

A proximal portion 1068 of the housing 1046 provides two flexible, elongate detents 1072 that can secure (e.g., lock) the handle 1014 to the connection hub 1008, thereby locating the handle 1014 (e.g., and the display 1012, attached thereto) at a fixed position along the primary axis 122 of the cannula 102. The proximal portion 1068 also provides a grip 1074 that can be used to manipulate the endoscopic device 1000.

The housing 1046 of the connection hub 1008 typically has a length (e.g., as measured along the primary axis 122 of the cannula 102) of about 10 cm to about 20 cm (e.g., about 15 cm) and a maximum width of about 15 cm to about 40 cm (e.g., about 25 cm). The proximal portion 1068 of the housing 1046 typically has a width (e.g., a handle seating width) of about 1.4 cm to about 1.8 cm (e.g., about 1.6 cm). The housing 1046 is typically made of one or more materials including ABS or polycarbonate or copolyester and is typically manufactured via injection molding. The fluid port, the internal operative conduit, and the entry port are substantially similar in construction and function to the fluid port 150, the operative conduit 156, and the entry port 152 described above with respect to the endoscopic device 100.

The display 1012 is similar in construction and function to the display 112 of the endoscopic device 100. Accordingly, the display 1012 includes a housing 1080, a screen 1082 (e.g., a touchscreen) that presents multiple GUIs at which a user can manipulate control of the imaging system 104 and other functionalities of the endoscopic device 1000, a power control (e.g., a push button, not shown) located along an upper rear surface of the display 1012, the internal electronics 186, an electrical connector 1088 (e.g., a micro HDMI connector or another type of connector) that mates with the connection port 1060 of the connection hub 1008 to relay signals between the imaging system 104 and the internal electronics 186, and a magnet 1090. The housing 1080 of the display 1012 typically has a length of about 11 cm to about 15 cm (e.g., about 13 cm), a width of about 2 cm to about 4 cm (e.g., about 3 cm), and a height of about 7 cm to about 9 cm (e.g., about 8 cm). The screen 1082 typically has a diagonal length of about 11 cm to about 14 cm (e.g., about 12.5 cm).

The handle 1014 defines a lower gripping portion 1092 and an upper wall portion 1025 that defines the channel 1023 by which the reusable portion 1018 of the endoscopic device 1000 can be slid over and secured to the single-use portion 1016. The upper wall portion 1025 defines two cutouts 1096 that are positioned to slide along the detents 1072 on the connection hub 1008 to secure the handle 1014 to the connection hub 1008. The handle 1014 has a length (e.g., along the central axis 1098) of about 8 cm to about 12 cm (e.g., about 10 cm). The channel 1023 of the handle typically has a width of about 1 cm to about 3 cm (e.g., about 2 cm). Referring particularly to FIG. 28, the reusable portion 1018 of the endoscopic device 1000 is typically oriented at an angle of about 80° to about 115° (e.g., about 95°) with respect to the connection hub 1008, as measured between the primary axis 122 of the cannula 102 and a central axis 1098 of the display 1012.

In some embodiments, the handle 1014 and the housing 1080 of the display 1012 are formed as a unitary, integrated component. The handle 1014 and the housing 1080 of the display 1012 are typically made of one or more materials that can chemically withstand various sterilization solutions and procedures, such as polycarbonate or copolyester or ABS. The handle 1014 and the housing 1080 are typically manufactured via injection molding.

To attach the handle 1014 (e.g., and the display 1012 attached thereto) to the connection hub 1008, the receptacle channel 1023 is slid distally over the proximal portion 1068 of the connection hub 1008 until the upper wall portion 1025 passes the elongate detents 1072 and abuts the shoulder 1001 of the distal portion 1066. As the upper wall portion 1025 is slid along the connection hub 1008, the upper wall portion 1025 depresses the detents 1072, which are biased to a position defining a distance that is otherwise wider than the receptacle 1096. Once the upper wall portion 1025 passes the detents 1072 to abut the shoulder 1001, the detents 1072 return (e.g., spring back) to the biased positions to lock the handle 1014 in position along the connection hub 1008. To detach the handle 1014 from the connection hub 1008, the detents 1072 are manually depressed by a user to allow proximal sliding of the upper wall portion 1025, and the handle 1014 is pulled (e.g., slid) off of the connection hub 1008.

As discussed above with respect to the endoscopic device 100, the reusable portion 1018 of the endoscopic device 1000 can be attached to the connection hub 1008 (e.g., at the connection port 1060 and along the housing 1046) prior to inserting the cannula 102 into the patient, the reusable portion 1018 can be unattached to (e.g., and in wireless communication with) the connection hub 1008 while the cannula 102 is inserted into the patient, or the reusable portion 1018 can be connected to the connection hub 1008 at the connection port 1060 by a display cable prior to inserting the cannula 102 into the patient.

Figure 30:
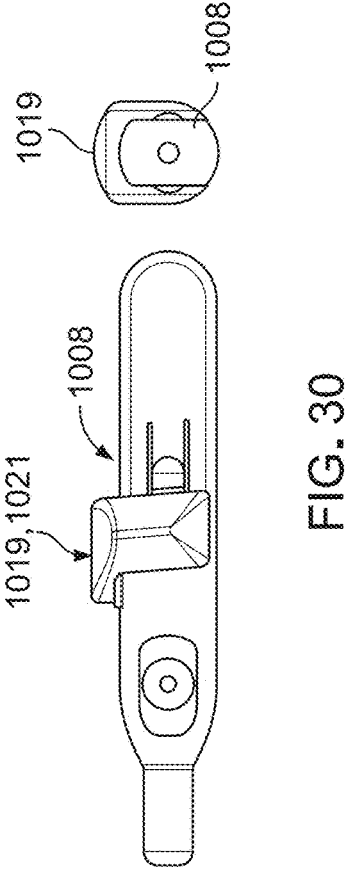
FIG. 30 provides a side view and an end view illustrating an extension cable connector of the endoscopic device of FIG. 28.

Referring to FIG. 30, an extension cable 1019 (e.g., a display cable) includes a connector 1021 that is formed to be slid past the detents 1072 on the proximal portion 868 of the connection hub 1008 and to mate with the cable port 1060. The extension cable 1019 further includes a cable (not shown) that extends from the connector 1021 and that includes a proximal end formed to mate with the electrical connector 1088 of the display 1012.

Figure 31:
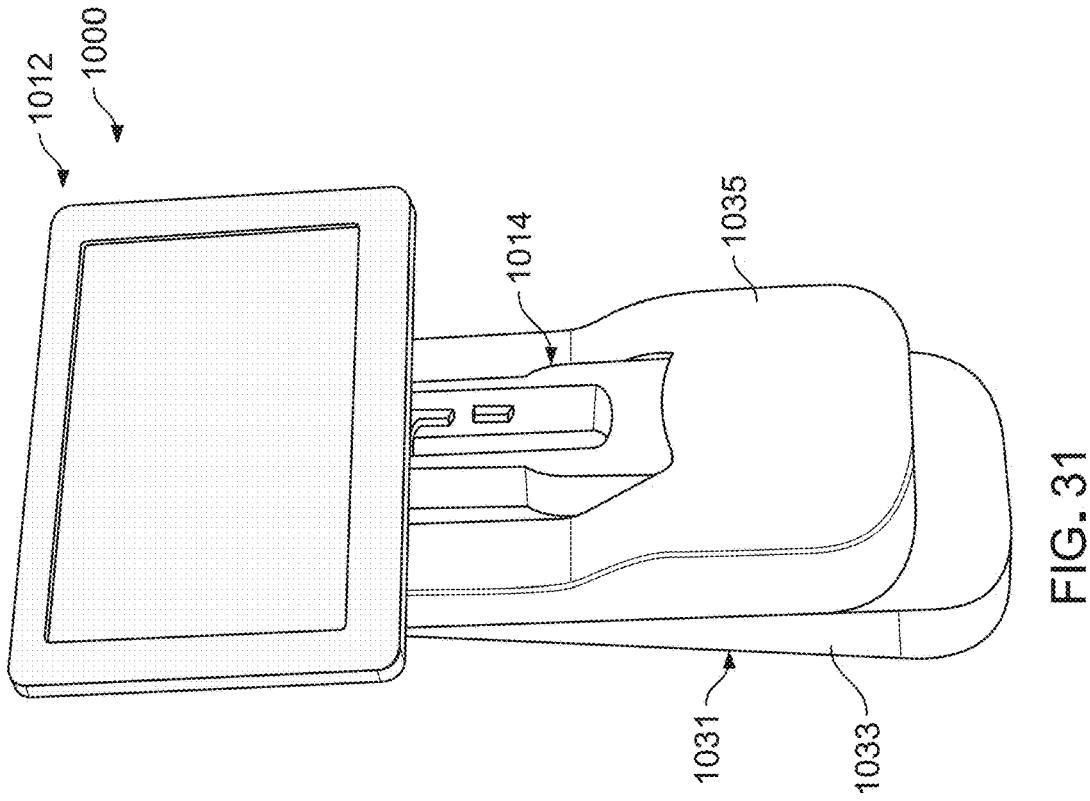
FIG. 31 is a perspective view of the endoscopic device of FIG. 28 secured to a docking station.

Referring to FIG. 31, the reusable portion 1018 of the endoscopic device 1000 is designed to be supported by (e.g., held and mated or attached to) a docking station 1031. The docking station 1031 includes a wall mount 1033, a holding unit 1035, and a metal component (not) shown that is sized and position to attract the magnet 1090 in the display 1012 to secure the reusable portion to the docking station 1031.

FIGS. 32-35 illustrate various portions of an endoscopic device 1100 that includes a handle 1114 and a display 1112 that are separable from each other. The endoscopic device 1100 is similar in construction and function in several aspects to the endoscopic device 1000 and accordingly includes the cannula 102, the imaging system 104 (e.g., with the exception of the camera actuator 104), a connection hub 1108, the handle 1114, and a reusable display 1112. The cannula 102, the imaging system 104, and the connection hub 1108 together form a single-use portion 1116 of the endoscopic device 1100. The handle 1114, while attachable to and detachable from the display 1112, may be a single-use handle or a multiple-use handle that, together with the reusable display 1112, forms a multiple-use portion of the endoscopic device 1100. In some embodiments, the handle may be single-use or multiple-use in any of the above-discussed or below-discussed endoscopic devices where the handle is attachable to and detachable from the respective display.

The connection hub 1108 surrounds the proximal end region 110 of the cannula 102 and is sized to pass through a channel 1123 of the handle 1114. The connection hub 1108 also provides several features for fluid and electrical communication between the proximal end region 110 of the cannula 102 and the distal tip 106 of the cannula 102. For example, the connection hub 1108 includes a housing 1146, a camera actuator 1148 (e.g., providing two opposite push buttons 1176), a fluid port (not shown) located adjacent the proximal end region 110 of the cannula 102, an internal entry port disposed at a proximal opening 1158 of the housing 1146, and an internal operative conduit that extends from the proximal end region 110 of the cannula 102 to the entry port.

The housing 1146 is generally axially aligned with the primary axis 122 of the cannula 102 and has a generally curved profile that is laterally symmetric. The housing 1146 defines a distal opening 1162 through which the cannula 102 passes, an opening (e.g., aligned with the sidewall opening 144 of the shaft 120) to which the fluid port is secured, the proximal opening 1158, and an upper connection port 1160 (e.g., a micro HDMI port or another type of port) to which the display 1112 or a display cable can be connected. In this regard, the connection hub 1108 also includes electrical components that communicate the camera actuator 1148 with the connection port 1160. The housing 1146 further defines additional internal wall features (e.g., flanges, openings, brackets, tabs, channels etc.) that properly position the fluid port, the camera actuator 1148, the connection port 1160, and the entry port.

A distal portion 1166 of the housing 1146 provides fluid communication between the distal tip 106 of the cannula 102 (e.g., at the luminal opening 132) and the fluid port and provides fluid communication between the distal tip 106 and the internal operative conduit (e.g., for further fluid communication to the entry port). The distal portion 1166 of the housing 1146 further provides electrical communication between the distal tip 106 of the cannula 102 (e.g., at the camera 142) and the camera actuator 1148, and between the distal tip 106 (e.g., at the camera 142) and the display 1112 (e.g., via the connection port 1160). The distal portion 1166 defines two receptacles 1170 surrounding the push buttons 1176 to facilitate location of the push buttons 1176 with a user's fingers. The distal portion 1166 further defines a shoulder 1101 against which the handle 1114 can abut for appropriate positioning of the handle 1114.

A proximal portion 1168 of the housing 1146 provides two flexible, elongate detents 1172 that can secure (e.g., lock) the handle 1114 to the connection hub 1108, thereby locating the handle 1114 (e.g., and the display 1112, attached thereto) at a fixed position along the primary axis 122 of the cannula 102. The proximal portion 1168 also provides a grip 1174 that can be used to manipulate the endoscopic device 1100.

The housing 1146 of the connection hub 1108 typically has a length (e.g., as measured along the primary axis 122 of the cannula 102) of about 10 cm to about 20 cm (e.g., about 15 cm) and a maximum width of about 15 cm to about 40 cm (e.g., about 25 cm). The proximal portion 1168 of the housing 1146 typically has a width (e.g., a handle seating width) of about 2 cm to about 4 cm (e.g., about 3 cm). The housing 1146 is typically made of one or more materials including ABS or polycarbonate or copolyester and is typically manufactured via injection molding. The fluid port, the internal operative conduit, and the entry port are substantially similar in construction and function to the fluid port 150, the operative conduit 156, and the entry port 152 described above with respect to the endoscopic device 100.

The display 1112 is similar in construction and function to the display 1012 of the endoscopic device 1000. Accordingly, the display 1112 includes a housing 1180, a screen 1182 (e.g., a touchscreen) that presents multiple GUIs at which a user can manipulate control of the imaging system 104 and other functionalities of the endoscopic device 1100, a power control (e.g., a push button, not shown) located along an upper rear surface of the display 1112, the internal electronics 186, an electrical connector 1188 (e.g., a micro HDMI connector or another type of connector) that mates with the connection port 1160 of the connection hub 1108 to relay signals between the imaging system 104 and the internal electronics 186, and a magnet 1190. The display 1112 also includes attachment flanges 1105 that are formed to mate with the handle 1114. The housing 1180 of the display 1112 typically has a length of about 11 cm to about 15 cm (e.g., about 13 cm), a width of about 2 cm to about 4 cm (e.g., about 3 cm), and a height of about 7 cm to about 9 cm (e.g., about 8 cm). The screen 1182 typically has a diagonal length of about 11 cm to about 14 cm (e.g., about 12.5 cm).

Figures 32, 33:
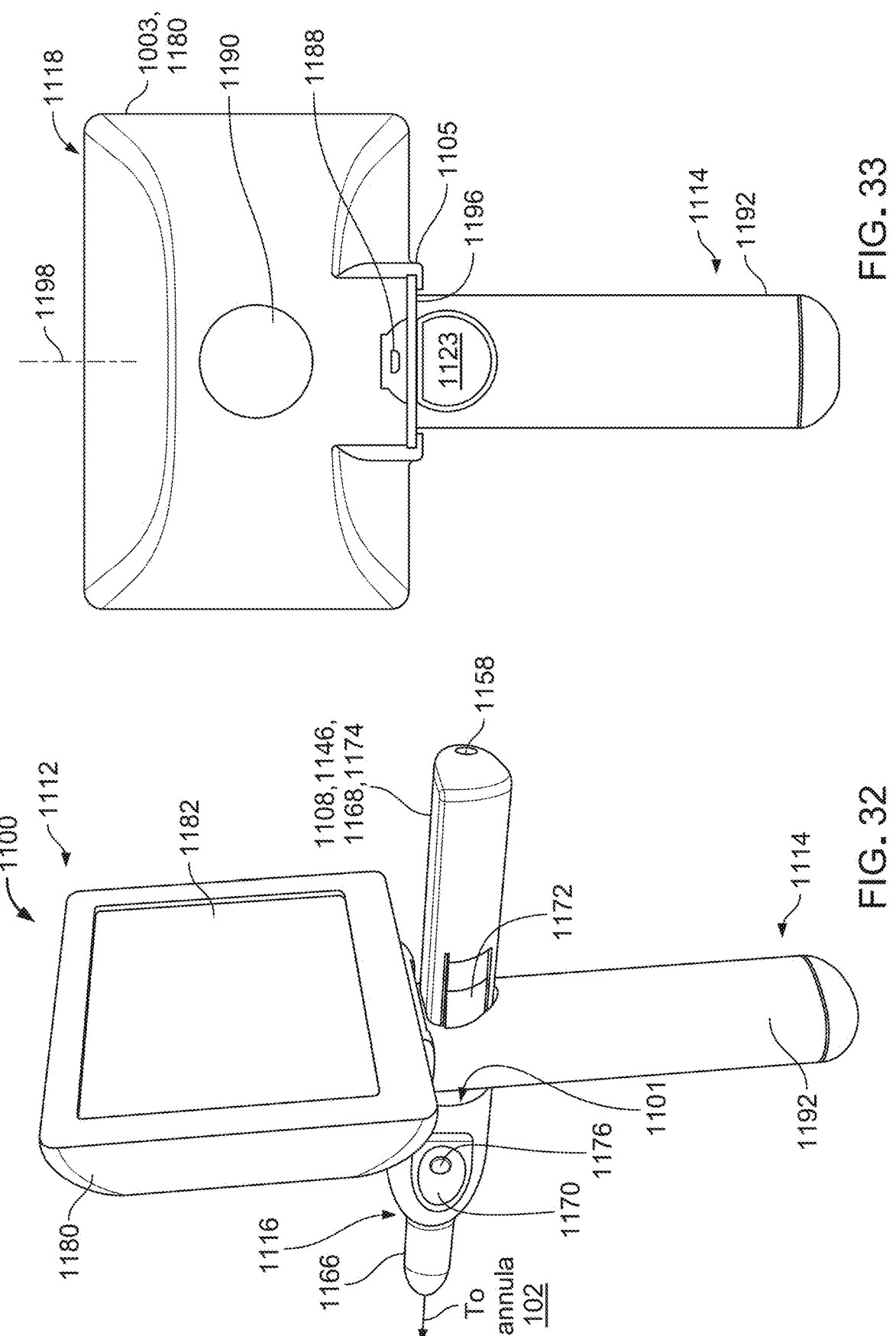
FIG. 32 is a perspective view of a portion of an endoscopic device including a handle that can be separated from a display and that can be slid over a single-use portion of the endoscopic device.
FIG. 33 is a rear view of a display and the handle of the endoscopic device of FIG. 32.

The handle 1114 includes a gripping portion 1192 that defines the channel 1123 by which the handle 1114 can be slid over and secured to the connection hub 1108. The handle 1114 also includes an attachment plate 1196 by which the handle 1114 can be secured to the display 1112. The handle 1114 handle has a length (e.g., along the central axis 1198) of about 8 cm to about 12 cm (e.g., about 10 cm), a width of about 2 cm to about 4 cm (e.g., about 3 cm), and a thickness of about 2 cm to about 4 cm (e.g., about 3 cm). Referring particularly to FIG. 32, the handle 1114 and the display 1112 are typically oriented at an angle of about 80° to about 115° (e.g., about 95°) with respect to the connection hub 1108, as measured between the primary axis 122 of the cannula 102 and the central axis 1198 of the display 1112.

The housing 1180 of the display 1112 and the handle 1114 are typically made of one or more materials that can chemically withstand various sterilization solutions and procedures, such as polycarbonate or copolyester or ABS. The handle 1114 and the housing 1180 are typically manufactured via injection molding.

To attach the handle 1114 to the connection hub 1108, the channel 1123 is slid distally over the proximal portion 1168 of the connection hub 1108 until the gripping portion 1192 passes the elongate detents 1172 and abuts the shoulder 1101 of the distal portion 1166. As the gripping portion 1192 is slid along the connection hub 1108, gripping portion 1192 depresses the detents 1172, which are biased to a position defining a distance that is otherwise wider than the channel 1123. Once gripping portion 1192 passes the detents 1172 to abut the shoulder 1101, the detents 1172 return (e.g., spring back) to the biased positions to lock the handle 1114 in position along the connection hub 1108. To detach the handle 1114 from the connection hub 1108, the detents 1172 are manually depressed by a user to allow proximal sliding of the gripping portion 1192, and the handle 1114 is pulled (e.g., slid) off of the connection hub 1108.

The display 1112 can be attached to the handle 1114 after attaching the handle 1114 to the connection hub 1108. To attach the display 1112 to the handle 1114, the flanges 1105 are slid distally onto the attachment plate 1196 to secure the display 1112 to the handle 1114 (e.g., via a friction fit). With the display 1112 attached to the handle 1114, the display 1112 can be electrically communicated with the connection hub 1108 by mating the electrical connector 1188 to the connection hub 1160. To detach the display 1112 from either or both of the handle 1114 and the connection hub 1108, the display 1112 can be pulled (e.g., slid) from either or both of the handle 1114 and the connection hub 1108. In some examples, separation of the display 1112 from the handle 1114 can facilitate procedures for cleaning and disinfecting the display 1112 and the handle 1114.

As discussed above with respect to the endoscopic devices 400, 500, 500, 800, 900, both the display 1112 and the handle 1114 of the endoscopic device 1100 can be attached to the single-use portion 1116 at the connection hub 1108 (e.g., at the connection port 1160 and along the housing 1146) prior to inserting the cannula 102 into the patient, the display 1112 can be unattached to (e.g., and in wireless communication with) the single-use portion 1116 (e.g., with the handle 1114 attached to or unattached to the single-use portion 1116) while the cannula 102 is inserted into the patient, or the display 1112 can be connected to the single-use portion 1116 at the connection port 1160 by an extension cable 1101 prior to inserting the cannula 102 into the patient (e.g., with the handle 1114 attached to or unattached to the single-use portion 1116).

Figure 34:
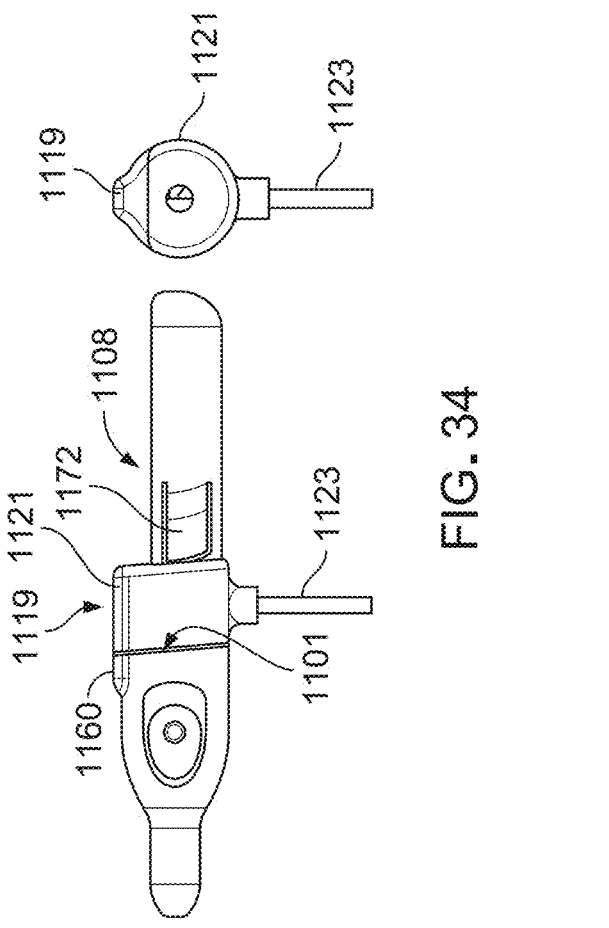
FIG. 34 provides a side view and an end view illustrating an extension cable connector of the endoscopic device of FIG. 32.

Referring to FIG. 34, an extension cable 1119 (e.g., a display cable) includes a connector 1121 that is formed to be slid past the detents 1172 on the proximal portion 1168 of the connection hub 1108 and to mate with the cable port 1160. The extension cable 1119 further includes a cable (not shown) that extends from the connector 1121 and that includes a proximal end formed to mate with the electrical connector 1188 of the display 1112.

Figure 35:
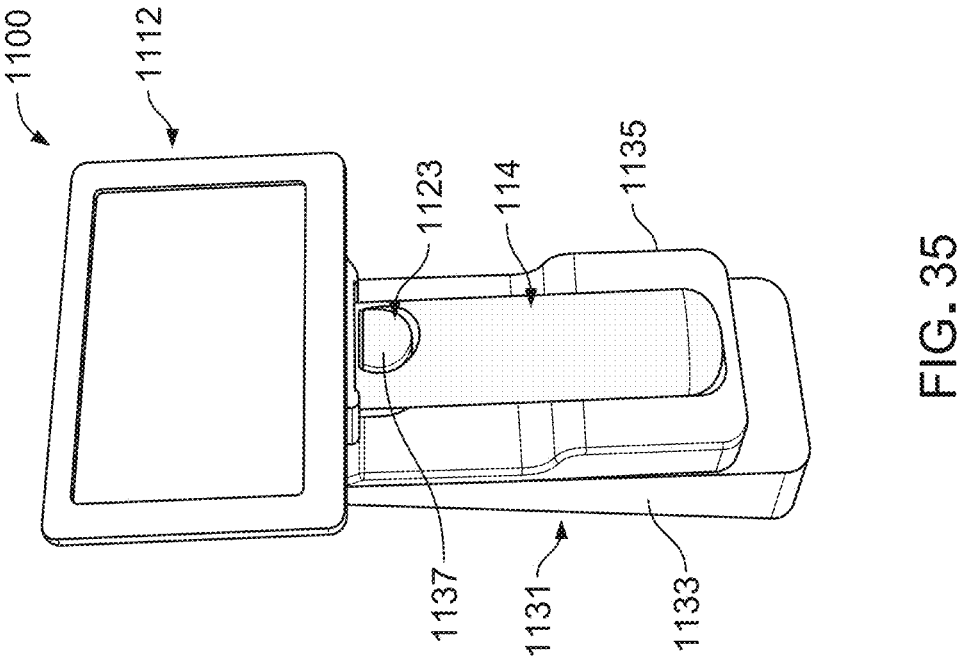
FIG. 35 is a perspective view of the endoscopic device of FIG. 32 secured to a docking station.

Referring to FIG. 35, the display 1112 and the handle 1114 of the endoscopic device 1100 are designed to be supported by (e.g., held and mated or attached to) a docking station 1131. The docking station 1131 includes a wall mount 1133, a holding unit 1135 including a protrusion 1137 that can support the handle 1114 at the channel 1123, and a metal component (not) shown that is sized and position to attract the magnet 1190 in the display 1112 to secure the display 1112 to the docking station 1131.

Figures 36, 37:
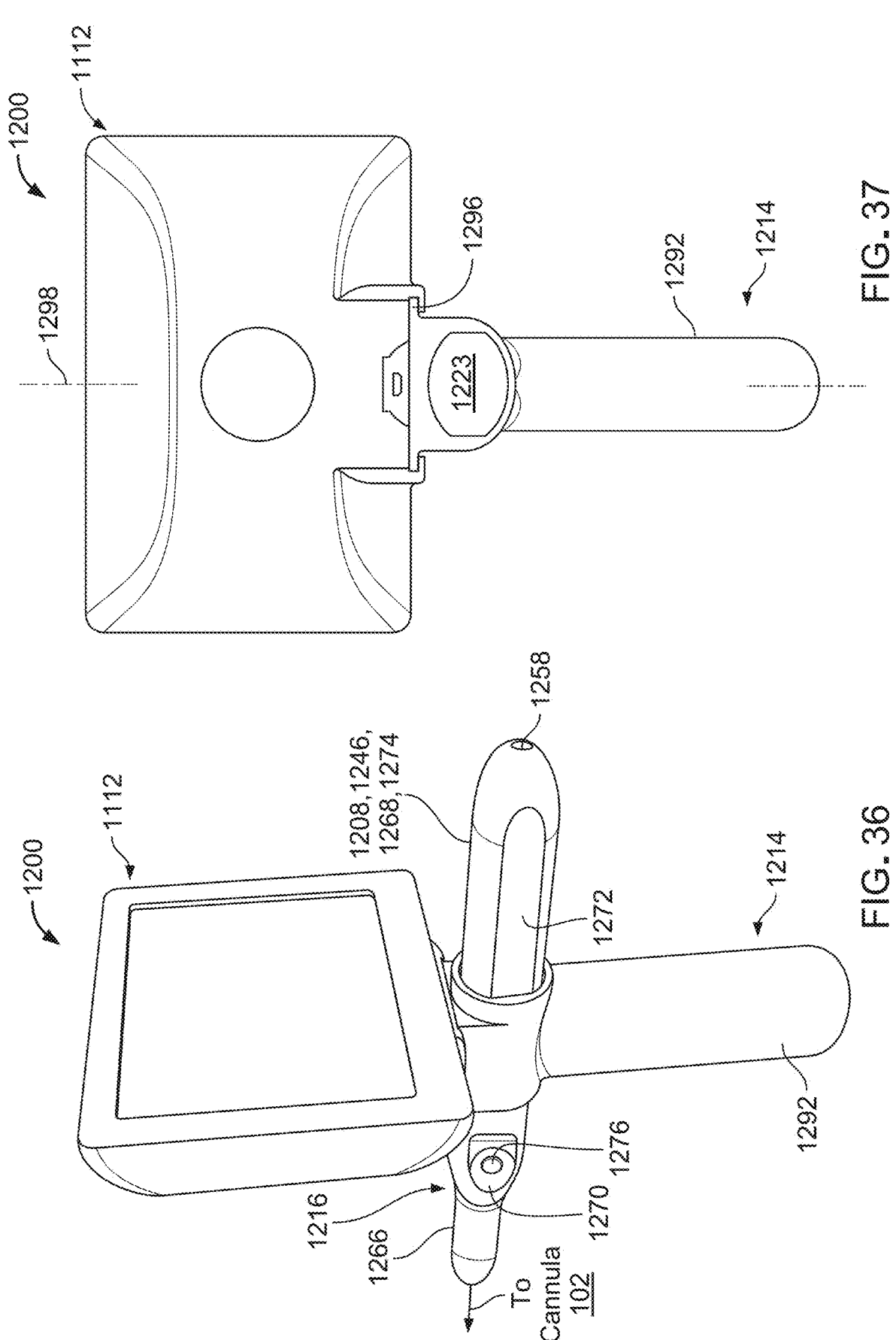
FIG. 36 is a perspective view of a portion of an endoscopic device including a handle that can be separated from a display and that can be slid over a single-use portion of the endoscopic device.
FIG. 37 is a rear view of a display and the handle of the endoscopic device of FIG. 36.
Figure 38:
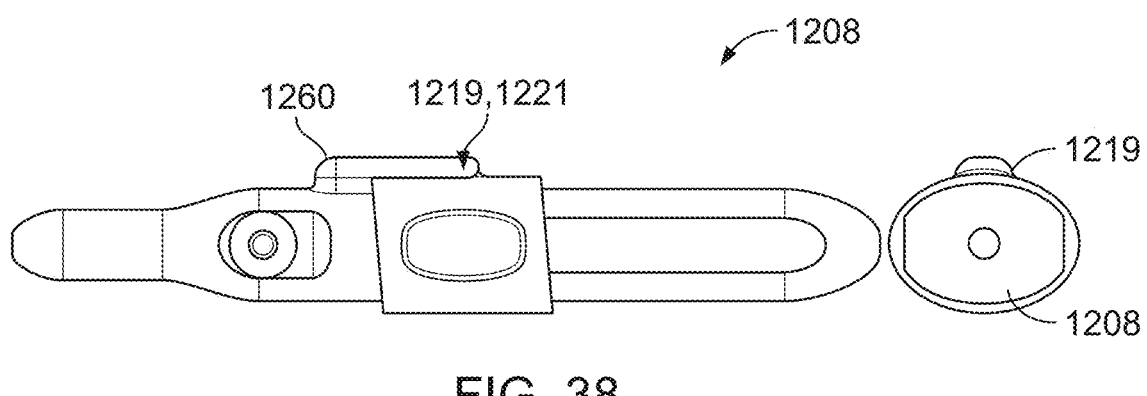
FIG. 38 provides a side view and an end view illustrating an extension cable connector of the endoscopic device of FIG. 36.

FIGS. 36-38 illustrate various portions of another endoscopic device 1200 that includes a handle 1214 that is separable from the display 1112. The endoscopic device 1200 is similar in construction and function in several aspects to the endoscopic device 1100 and accordingly includes the cannula 102, the imaging system 104 (e.g., with the exception of the camera actuator 148), a connection hub 1208, the handle 1214, and the reusable display 1112. The cannula 102, the imaging system 104, and the connection hub 1208 together form a single-use portion 1216 of the endoscopic device 1200. The handle 1214, while attachable to and detachable from the display 1112, may be a single-use handle or a multiple-use handle that, together with the reusable display 1112, forms a multiple-use portion of the endoscopic device 1200.

The connection hub 1208 surrounds the proximal end region 110 of the cannula 102 and is sized to pass through a channel 1223 of the handle 1214. The connection hub 1208 also provides several features for fluid and electrical communication between the proximal end region 110 of the cannula 102 and the distal tip 106 of the cannula 102. For example, the connection hub 1208 includes a housing 1246, a camera actuator 1248 (e.g., providing two opposite push buttons 1276), a fluid port (not shown) located adjacent the proximal end region 110 of the cannula 102, an internal entry port disposed at a proximal opening 1258 of the housing 1246, and an internal operative conduit that extends from the proximal end region 110 of the cannula 102 to the entry port.

The housing 1246 is generally axially aligned with the primary axis 122 of the cannula 102 and has a generally curved profile that is laterally symmetric. The housing 1246 defines a distal opening 1262 through which the cannula 102 passes, an opening (e.g., aligned with the sidewall opening 144 of the shaft 120) to which the fluid port is secured, the proximal opening 1258, and an upper connection port 1260 (e.g., a micro HDMI port or another type of port) to which the display 1112 or a display cable can be connected. In this regard, the connection hub 1208 also includes electrical components that communicate the camera actuator 1248 with the connection port 1260. The housing 1246 further defines additional internal wall features (e.g., flanges, openings, brackets, tabs, channels etc.) that properly position the fluid port, the camera actuator 1248, the connection port 1260, and the entry port.

A distal portion 1266 of the housing 1246 provides fluid communication between the distal tip 106 of the cannula 102 (e.g., at the luminal opening 132) and the fluid port and provides fluid communication between the distal tip 106 and the internal operative conduit (e.g., for further fluid communication to the entry port). The distal portion 1266 of the housing 1246 further provides electrical communication between the distal tip 106 of the cannula 102 (e.g., at the camera 142) and the camera actuator 1248, and between the distal tip 106 (e.g., at the camera 142) and the display 1112 (e.g., via the connection port 1260). The distal portion 1266 defines two receptacles 1270 surrounding the push buttons 1276 to facilitate location of the push buttons 1276 with a user's fingers. The distal portion 1266 further defines a shoulder 1201 against which the handle 1214 can abut for appropriate positioning of the handle 1214.

A proximal portion 1268 of the housing 1246 provides two locking features 1272 that can secure (e.g., lock) the handle 1214 to the connection hub 1208, thereby locating the handle 1214 (e.g., and the display 1112, attached thereto) at a fixed position along the primary axis 122 of the cannula 102. The proximal portion 1268 also provides a grip 1274 that can be used to manipulate the endoscopic device 1200.

The fluid port, the internal operative conduit, and the entry port are substantially similar in construction and function to the fluid port 150, the operative conduit 156, and the entry port 152 described above with respect to the endoscopic device 100.

The handle 1214 includes a gripping portion 1292 that defines the channel 1223 by which the handle 1214 can be slid over and secured to the connection hub 1208. The handle 1214 also includes an attachment plate 1296 by which the handle 1214 can be secured to the display 1112.

To attach the handle 1214 to the connection hub 1208, the channel 1223 is slid distally over the proximal portion 1268 of the connection hub 1208 until the gripping portion 1292 passes the elongate detents and abuts the shoulder 1201 of the distal portion 1266. To detach the handle 1214 from the connection hub 1208, the detents 1272 are manually depressed by a user to allow proximal sliding of the gripping portion 1292, and the handle 1214 is pulled (e.g., slid) off of the connection hub 1208.

The display 1112 can be attached to the handle 1214 after attaching the handle 1214 to the connection hub 1108. To attach the display 1112 to the handle 1214, the flanges 1105 are slid distally onto the attachment plate 1296 to secure the display 1112 to the handle 1214 (e.g., via a friction fit). With the display 1112 attached to the handle 1214, the display 1112 can be electrically communicated with the connection hub 1208 by mating the electrical connector 1188 to the connection hub 1260. To detach the display 1112 from either or both of the handle 1214 and the connection hub 1208, the display 1112 can be pulled (e.g., slid) from either or both of the handle 1214 and the connection hub 1208.

As discussed above with respect to the endoscopic devices 400, 500, 500, 800, 900, 1100, both the display 1112 and the handle 1214 of the endoscopic device 1200 can be attached to the single-use portion 1216 at the connection hub 1208 (e.g., at the connection port 1260 and along the housing 1246) prior to inserting the cannula 102 into the patient, the display 1112 can be unattached to (e.g., and in wireless communication with) the single-use portion 1216 (e.g., with the handle 1214 attached to or unattached to the single-use portion 1216) while the cannula 102 is inserted into the patient, or the display 1112 can be connected to the single-use portion 1216 at the connection port 1260 by an extension cable 1201 prior to inserting the cannula 102 into the patient (e.g., with the handle 1214 attached to or unattached to the single-use portion 1216).

Referring to FIG. 38, an extension cable 1219 (e.g., a display cable) includes a connector 1221 that is formed to be slid past the detents 1272 on the proximal portion 1268 of the connection hub 1208 and to mate with the cable port 1260. The extension cable 1219 further includes a cable (not shown) that extends from the connector 1221 and that includes a proximal end formed to mate with the electrical connector 1288 of the display 1112.

Figure 39:
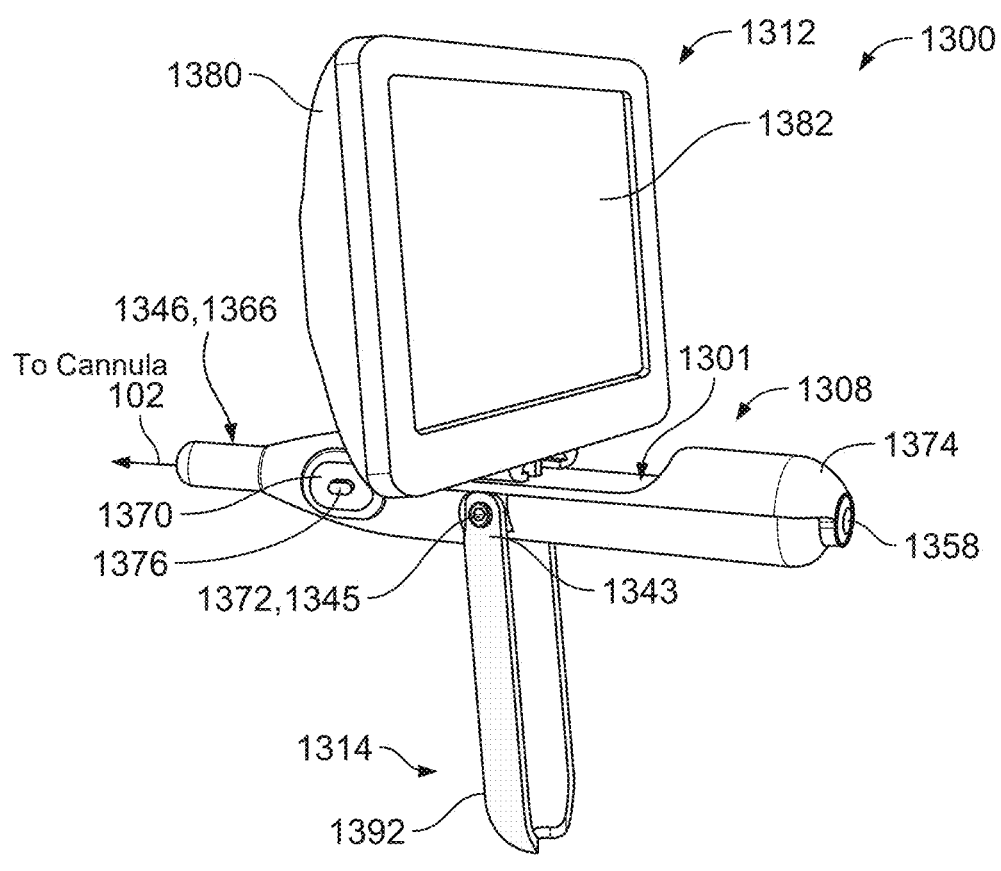
FIG. 39 is a perspective view of a portion of an endoscopic device including a display that is supported by a connection hub.
Figure 40:
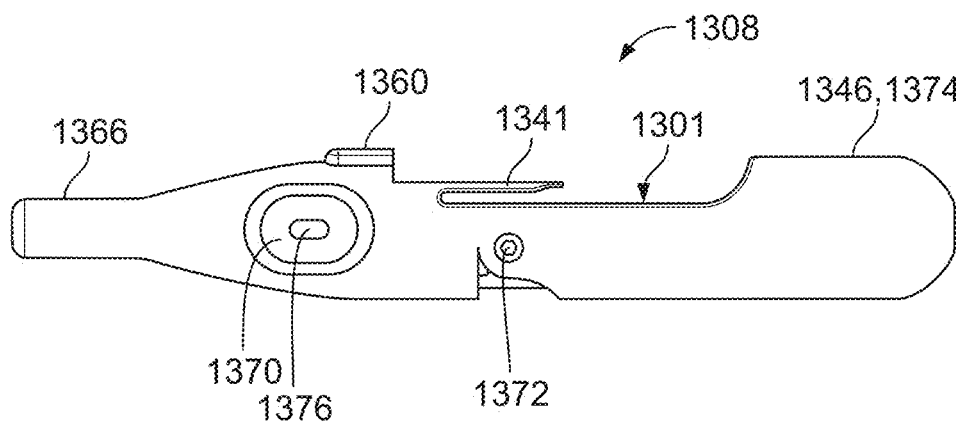
FIG. 40 is a side view of the connection hub of the endoscopic device of FIG. 39.
Figure 41:
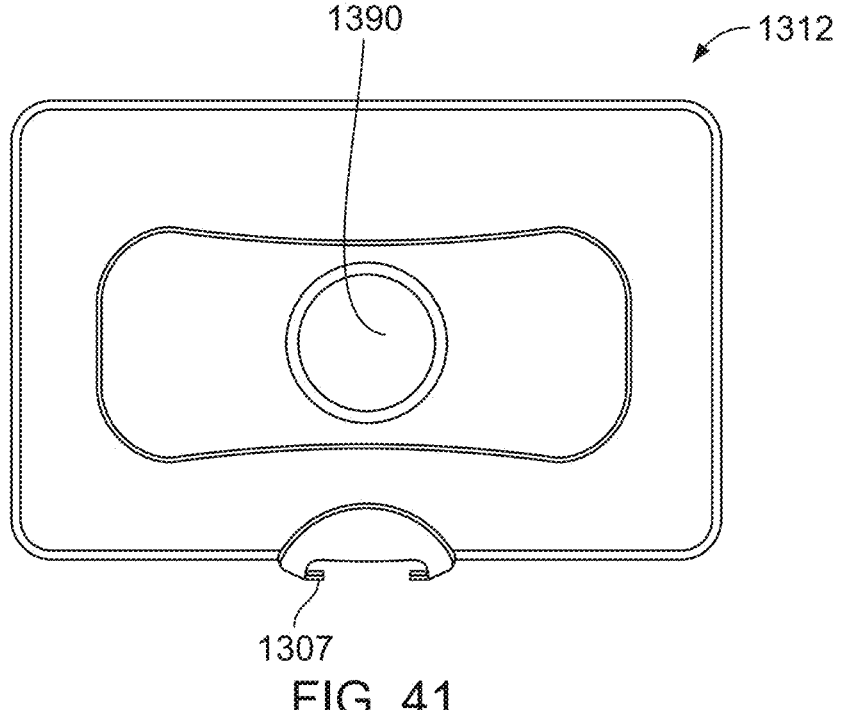
FIG. 41 is a rear view of the display of the endoscopic device of FIG. 39.

While the above-mentioned endoscopic devices have been described and illustrated as including displays that are supported by the handles, in some embodiments, an endoscopic device includes a display that is attachable to and supported by a connection hub. For example, FIGS. 39-41 illustrate various portions of an endoscopic device 1300 that includes such a display 1312 and connection hub 1308. The endoscopic device 1300 is similar in construction and function in several aspects to the above-discussed endoscopic devices and accordingly includes the cannula 102, the imaging system 104 (e.g., with the exception of the camera actuator 148), the connection hub 1308, a handle 1314, and the display 1312. The cannula 102, the imaging system 104, and the connection hub 1308 together form a single-use portion 1316 of the endoscopic device 1300, while the display 1312 and the handle 1314, though not directly connected to each other, form a reusable portion 1318 of the endoscopic device 1300.

The connection hub 1308 surrounds the proximal end region 110 of the cannula 102 and serves as a mounting piece for both the display 1312 the handle 1314. The connection hub 1308 also provides several features for fluid and electrical communication between the proximal end region 110 of the cannula 102 and the distal tip 106 of the cannula 102. For example, the connection hub 1308 includes a housing 1346, a camera actuator 1348 (e.g., providing two opposite push buttons 1376), a fluid port (not shown) located adjacent the proximal end region 110 of the cannula 102, an internal entry port disposed at a proximal opening 1358 of the housing 1346, and an internal operative conduit that extends from the proximal end region 110 of the cannula 102 to the entry port.

The housing 1346 is generally axially aligned with the primary axis 122 of the cannula 102 and has a generally curved profile that is laterally symmetric. The housing 1346 defines a distal opening 1362 through which the cannula 102 passes, an opening (e.g., aligned with the sidewall opening 144 of the shaft 120) to which the fluid port is secured, the proximal opening 1358, and an upper connection port 1360 (e.g., a micro HDMI port or another type of port) to which the display 1312 or a display cable can be connected. In this regard, the connection hub 1308 also includes electrical components that communicate the camera actuator 1348 with the connection port 1360. The housing 1346 further defines additional internal wall features (e.g., flanges, openings, brackets, tabs, channels etc.) that properly position the fluid port, the camera actuator 1348, the connection port 1360, and the entry port.

A distal portion 1366 of the housing 1346 provides fluid communication between the distal tip 106 of the cannula 102 (e.g., at the luminal opening 132) and the fluid port and provides fluid communication between the distal tip 106 and the internal operative conduit (e.g., for further fluid communication to the entry port). The distal portion 1366 of the housing 1346 further provides electrical communication between the distal tip 106 of the cannula 102 (e.g., at the camera 142) and the camera actuator 1348, and between the distal tip 106 (e.g., at the camera 142) and the display 1312 (e.g., via the connection port 1360). The distal portion 1366 defines two receptacles 1370 surrounding the push buttons 1376 to facilitate location of the push buttons 1376 with a user's fingers.

A proximal portion 1368 of the housing 1346 supports a pin 1372 to which the handle 1314 can be secured and pivoted with respect to the primary axis 128 of the elongate cannula 102. Accordingly, the pin 1372 locates the handle 1314 (e.g., one end of the handle 1314) at a fixed position along the primary axis 122 of the cannula 102. The proximal portion 1368 also provides a grip 1374 that can be used to manipulate the endoscopic device 1300. The proximal portion 1368 further defines a seat 1301 on which the display 1312 can be supported and a retention member 1341 for securing the display 1312 in an operable position, as shown in FIG. 39. The seat 1301 is formed as flat recessed surface, and the retention member 1341 is provided as a thin, elongate extension that is formed to mate with attachment flanges 1307 of the display 1312.

The housing 1346 of the connection hub 1308 typically has a length (e.g., as measured along the primary axis 122 of the cannula 102) of about 10 cm to about 20 cm (e.g., about 15 cm) and a maximum width of about 15 cm to about 40 cm (e.g., about 25 cm). The proximal portion 1368 of the housing 1346 typically has a width (e.g., a handle seating width) of about 2 cm to about 4 cm (e.g., about 3 cm). The housing 1346 is typically made of one or more materials including ABS or polycarbonate or copolyester and is typically manufactured via injection molding. The fluid port, the internal operative conduit, and the entry port are substantially similar in construction and function to the fluid port 150, the operative conduit 156, and the entry port 152 described above with respect to the endoscopic device 100.

The display 1312 is similar in construction and function to the display 1112 of the endoscopic devices 1100, 1200. Accordingly, the display 1312 includes a housing 1380, the screen 1182, a power control (e.g., a push button, not shown) located along an upper rear surface of the display 1312, the internal electronics 186, an electrical connector 1388 (e.g., a micro HDMI connector or another type of connector) that mates with the connection port 1360 of the connection hub 1308 to relay signals between the imaging system 104 and the internal electronics 186, and a magnet 1390. The housing 1380 of the display 1312 typically has a length of about 11 cm to about 15 cm (e.g., about 13 cm), a width of about 2 cm to about 4 cm (e.g., about 3 cm), and a height of about 7 cm to about 9 cm (e.g., about 8 cm). Referring particularly to FIG. 39, the display 1312 is typically oriented at an angle of about 80° to about 115° (e.g., about 95°) with respect to the connection hub 1308, as measured between the primary axis 122 of the cannula 102 and a central axis 1398 of the display 1012. The housing 1380 of the display 1312 is typically manufactured via injection molding.

The handle 1314 defines a gripping portion 1392 that includes two connection tabs 1343 with holes 1345 by which the handle 1314 can be attached to the pin 1372 on the connection hub 1308 and by which the handle 1314 can be pivoted about the pin 1372. The handle 1314 is accordingly made of one or more materials that allow the connection tabs 1343 to flex to be slid around both ends of the pin 1372, as well as that can chemically withstand various sterilization solutions and procedures, such as polycarbonate or copolyester or ABS. The handle 1314 has a length of about 8 cm to about 12 cm (e.g., about 10 cm) and a width of about 2 cm to about 4 cm (e.g., about 3 cm).

The handle 1314 is attached to the connection hub 1308 prior to inserting the cannula 102 into the patient. To attach the handle 1314 to the connection hub 1308, the grip 1374 is squeezed to move the connection tabs 1343 farther apart from each other (e.g., to a widen a gap between the connection tabs 1343) until both connection tabs 1343 can be placed about both ends of the pin 1372. Once the connection tabs 1343 are aligned with the pin 1372, the grip 1374 is released to allow the connection tabs 1343 to retract (e.g., move inwardly) onto respective ends of the pin 1372. The grip 1374 can pivot about the pin 1372 and is held in a desired pivotal position by a detent feature between the connection tabs 1343 and the housing 1346. To detach the handle 1314 from the connection hub 1308, the grip 1374 is again squeezed to move the connection tabs 1343 farther apart and off of the pin 1372, at which time the handle 1314 can be moved away from the connection hub 1308.

The display 1312 can be attached to the connection hub 1308 prior to inserting the cannula 102 into the patient, the display 1312 can be unattached to (e.g., and in wireless communication with) the connection hub 1308 while the cannula 102 is inserted into the patient, or the display 1312 can be connected to the connection hub 1308 at the connection port 1360 by a display cable prior to inserting the cannula 102 into the patient. To attach the display 1312 to the connection hub 1308, the display 1312 is placed at a proximal end of the seat 1301 and moved distally to slide the flanges 1307 onto the retention member 1341 of the connection hub 1308 until the electrical connector 1388 mates with the connection port 1360. The display 1312 is held in place on the retention member 1341 by a frictional fit. The handle 1314 may be attached or unattached to the connection hub 1308 for any of these configurations related to the connection between the display 1312 and the connection hub 1308. To disconnect the display 1312 from the connection hub 1308, the display 1312 is pulled proximally relative to the connection hub 1360 to move the flanges 1307 off of the retention member 1341. In some examples, providing the display 1312 and the handle 1314 as separate components can facilitate procedures for cleaning and disinfecting the display 1312 and the handle 1314.

While several of the above-mentioned endoscopic devices have been described and illustrated as including a magnet that is designed to interface with a separate metal accessory, in some embodiments, an endoscopic device that is substantially similar in construction and function to any of the endoscopic devices discussed above may alternatively include a metal plate that is designed to interface with a separate magnet accessory.

Figure 42:
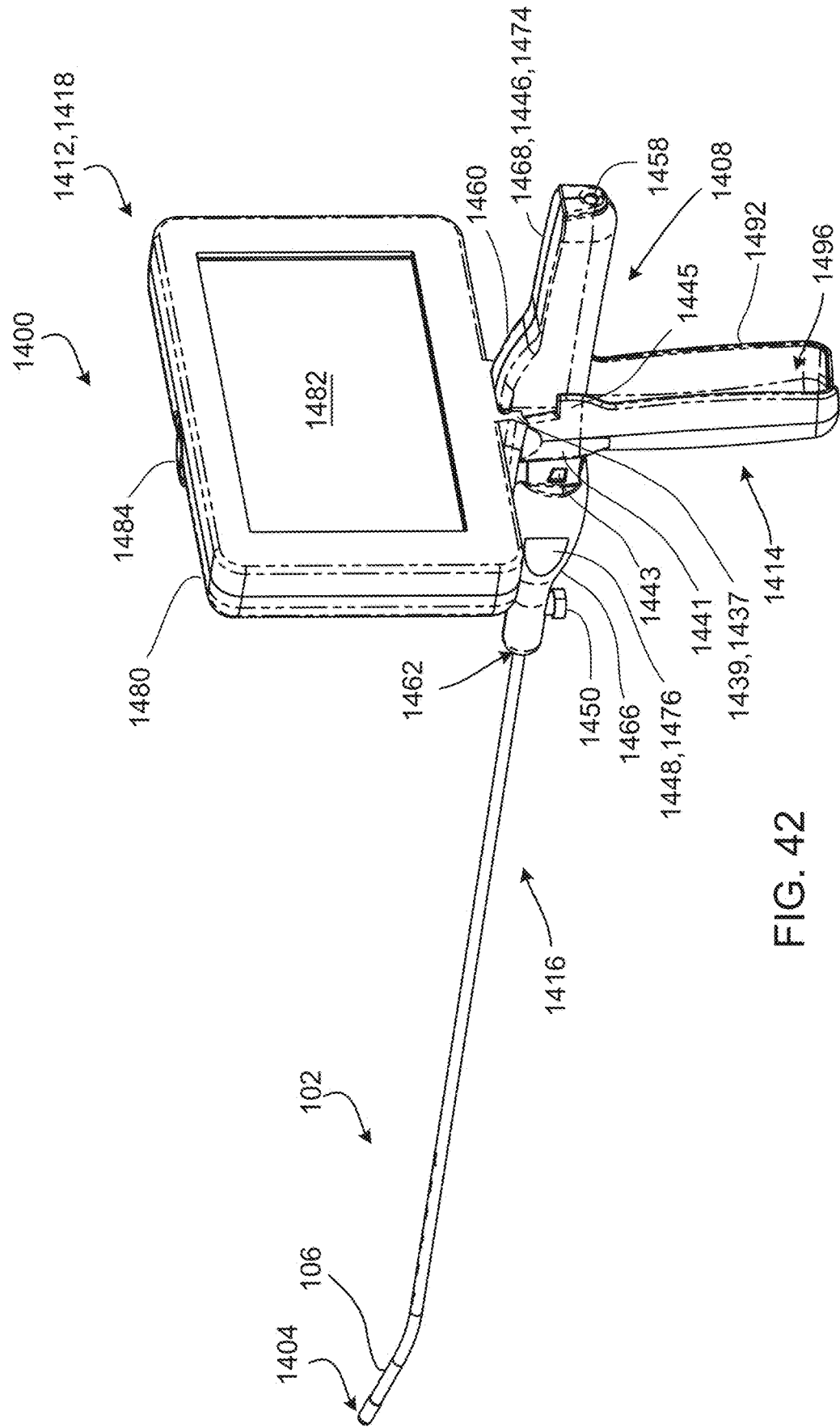
FIG. 42 is a perspective view of an endoscopic device including a pivotable handle.
Figure 43:
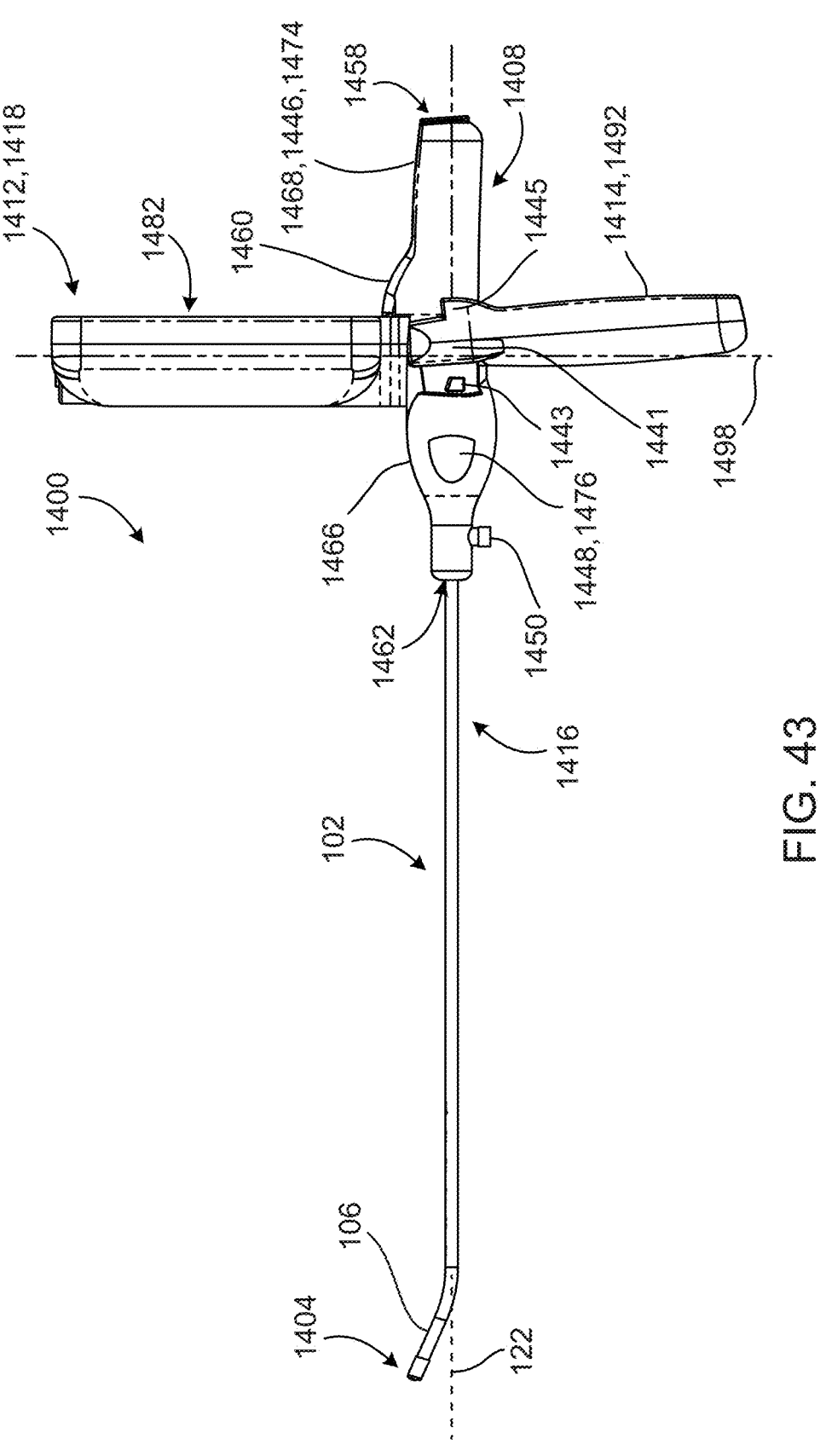
FIG. 43 is a side view of the endoscopic device of FIG. 42.

FIGS. 42 and 43 illustrate another endoscopic device 1400 that includes a display 1412 and a pivotable handle 1414 that are supported by a connection hub 1408. The endoscopic device 1400 is similar in construction and function in several aspects to the above-discussed endoscopic devices and accordingly further includes the cannula 102 and an imaging system 1404. The cannula 102, the imaging system 1404, the connection hub 1408, and the handle 1414 together form a single-use portion 1416 of the endoscopic device 1400, while the display 1412 provides a reusable portion 1418 of the endoscopic device 1400.

Figures 44, 45:
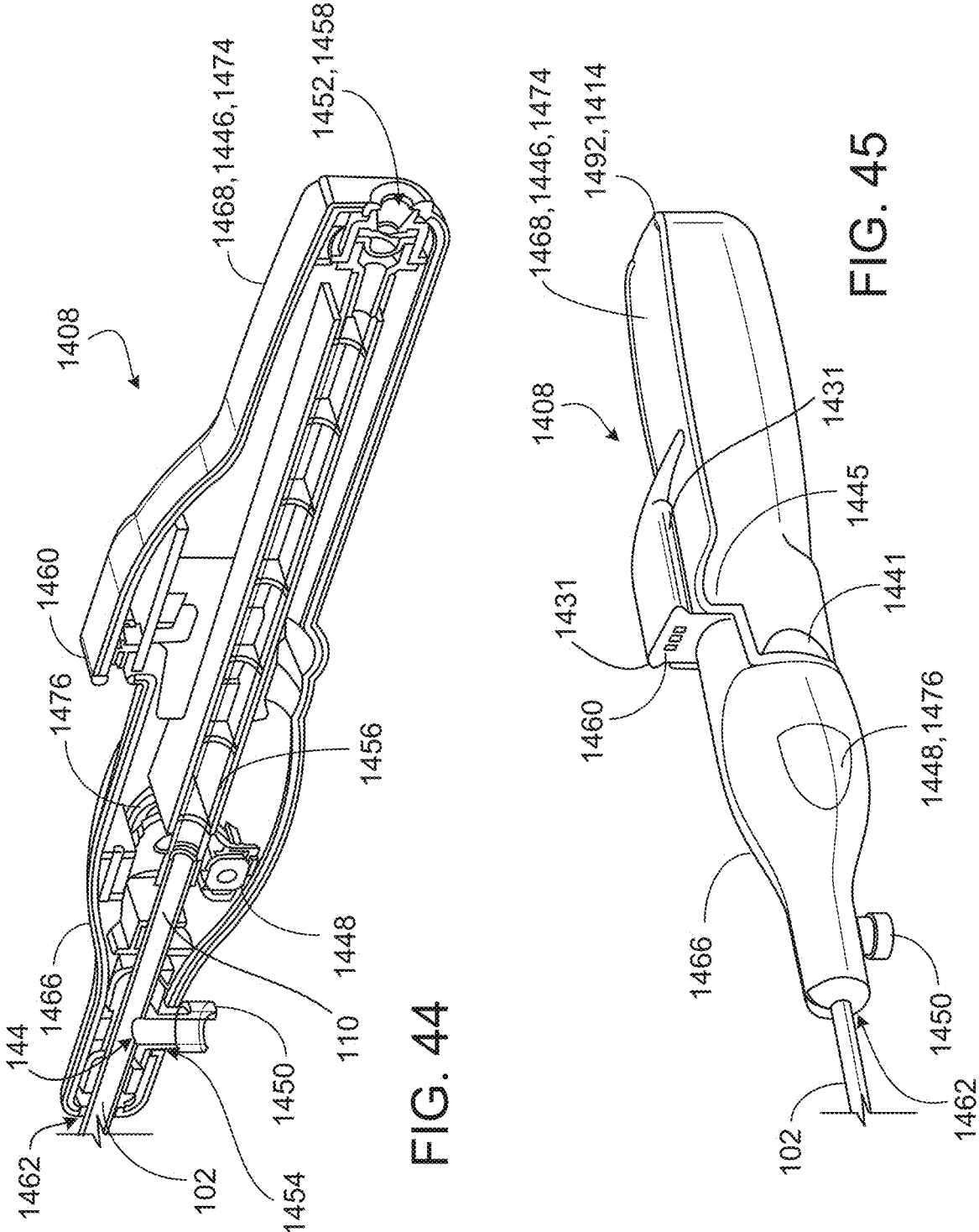
FIG. 44 is a perspective cross-sectional view of a connection hub of the endoscopic device of FIG. 42.
FIG. 45 is a perspective view of the connection hub of FIG. 44.

Referring to FIGS. 44 and 45, the connection hub 1408 surrounds the proximal end region 110 of the cannula 102 and serves as a mounting piece for the reusable display 1412. The connection hub 1408 also provides several features for fluid and electrical communication between the proximal end region 110 of the cannula 102 and the distal tip 106 of the cannula 102. For example, the connection hub 1408 includes a housing 1446, a camera actuator 1448 (e.g., providing two opposite push buttons 1476), a fluid port 1450 located adjacent the proximal end region 110 of the cannula 102, an entry port 1452 disposed at a proximal opening 1458 of the housing 1446, and a straight operative conduit 1456 that extends from the proximal end region 110 of the cannula 102 to the entry port 1452.

The housing 1446 is generally axially aligned with the primary axis 122 of the cannula 102 and has a generally curved profile that is laterally symmetric. The housing 1446 defines a distal opening 1462 through which the cannula 102 passes, an opening 1454 (e.g., aligned with the sidewall opening 144 of the shaft 120) to which the fluid port is secured, the proximal opening 1458, and a horizontally oriented upper connection port 1460 (e.g., a micro HDMI port or another type of port) to which the display 1412 or a display cable can be connected. In this regard, the connection hub 1408 also includes electrical components that communicate the camera actuator 1448 with the connection port 1460. The connection port 1460 defines opposite, elongate flanges 1431 that can be engaged with the display 1412 to secure the display 1412 to the connection hub 1408. The housing 1446 further defines additional internal wall features (e.g., flanges, openings, brackets, tabs, channels etc.) that properly position the fluid port 1450, the camera actuator 1448, the connection port 1460, and the entry port 1452.

A distal portion 1466 of the housing 1446 provides fluid communication between the distal tip 106 of the cannula 102 (e.g., at the luminal opening 132) and the fluid port 1450 and provides fluid communication between the distal tip 106 and the operative conduit 1456 (e.g., for further fluid communication to the entry port 1452). The distal portion 1466 of the housing 1446 further provides electrical communication between the distal tip 106 of the cannula 102 (e.g., at the camera 142) and the camera actuator 1448, and between the distal tip 106 (e.g., at the camera 142) and the display 1412 (e.g., via the connection port 1460).

A proximal portion 1468 of the housing 1446 supports an internal pin to which the handle 1414 is secured and pivoted with respect to the primary axis 128 of the elongate cannula 102. Accordingly, the pin locates the handle 1414 (e.g., one end of the handle 1414) at a fixed position along the primary axis 122 of the cannula 102. The proximal portion 1468 also provides a grip 1474 that can be used to manipulate the endoscopic device 1400.

The housing 1446 of the connection hub 1408 typically has a length (e.g., as measured along the primary axis 122 of the cannula 102) of about 10 cm to about 20 cm (e.g., about 15 cm) and a maximum width of about 20 cm to about 30 cm (e.g., about 25 cm). The proximal portion 1468 of the housing 1446 (e.g., excluding the handle 1414) typically has a width of about 1.4 cm to about 1.8 cm (e.g., about 1.6 cm). The housing 1446 is typically made of one or more materials, such as ABS or polycarbonate or copolyester and is typically manufactured via injection molding. The fluid port 1450, the operative conduit 1456, and the entry port 1452 are substantially similar in construction and function to the fluid port 150, the operative conduit 156, and the entry port 152 described above with respect to the endoscopic device 100, except that the entry port 1452 is straight instead of curved.

The imaging system 1404 is also similar in construction and function to the imaging system 104. For example, the imaging system 1404 includes the camera 142, the LEDs 138 located on opposite sides of the camera 142 to evenly illuminate surrounding tissues for image acquisition, the camera actuator 1448, one or more electrical cables (e.g., one or more video and control cables, not shown) that extend from the camera 142 and the LEDs 138 to the camera actuator 1448 and to the connection port 1460, and other electrical components that provide electrical communication amongst the various components of the imaging system 1404 and the connection port 1460 of the connection hub 1408. In some embodiments, the one or more electrical cables extend through the lumen 128 of the cannula 102. In some embodiments, the one or more electrical cables extend within channels in a sidewall of the cannula 102. In some embodiments, the imaging system 1404 includes a flex circuit member to carry the electrical communications instead of one or more electrical cables. The push buttons 1476 are flexible components that may be formed from an overmolded elastomer such that when either or both of the push buttons 1476 are depressed, the push buttons 1476 temporarily move internal components of the camera actuator to 1448 to initiate image capture, as described above with respect to the push buttons 176 and the camera actuator 148.

Figures 46, 47:
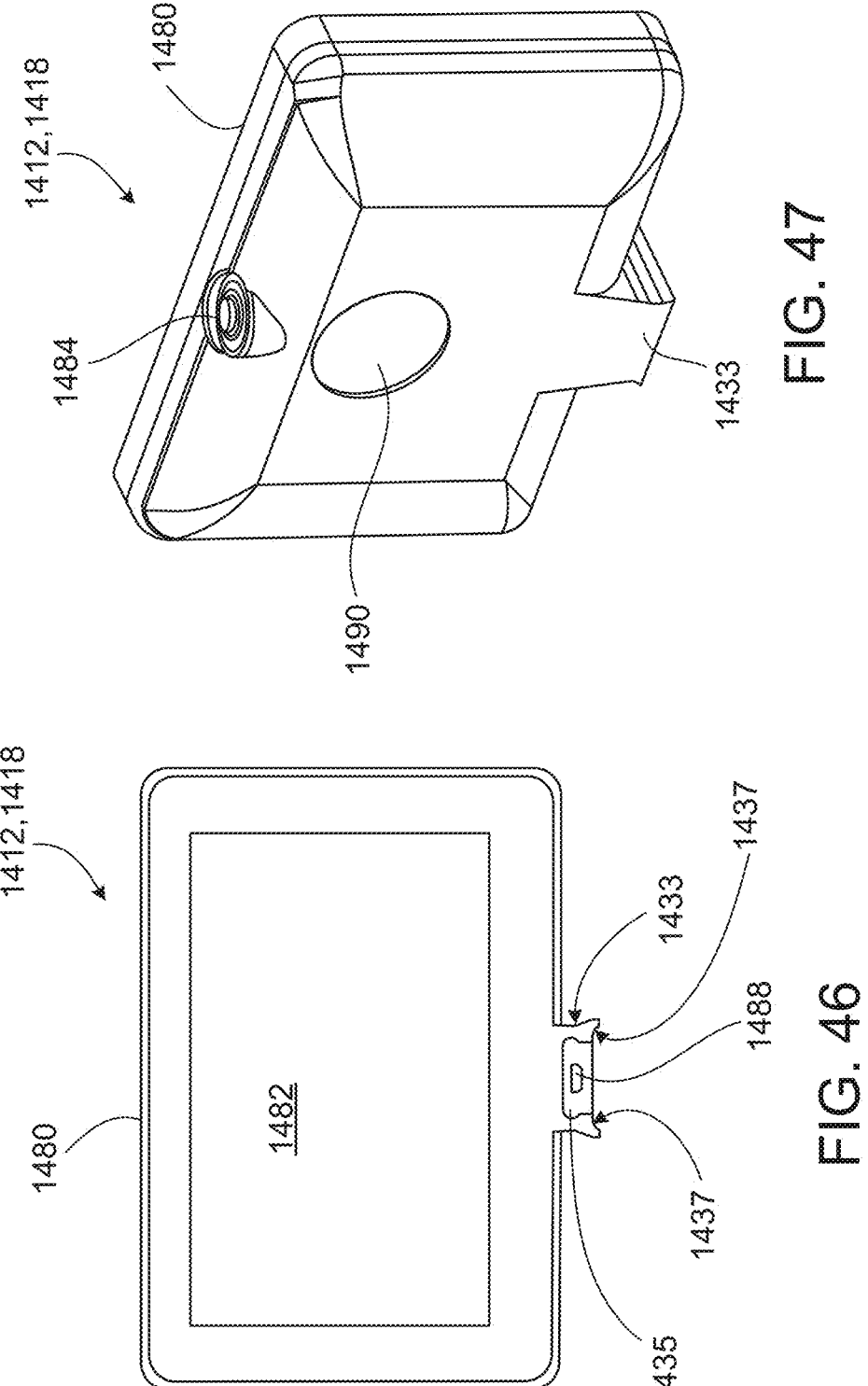
FIG. 46 is a front view of a display of the endoscopic device of FIG. 42.
FIG. 47 is a rear perspective view of the display of FIG. 46.
Figure 48:
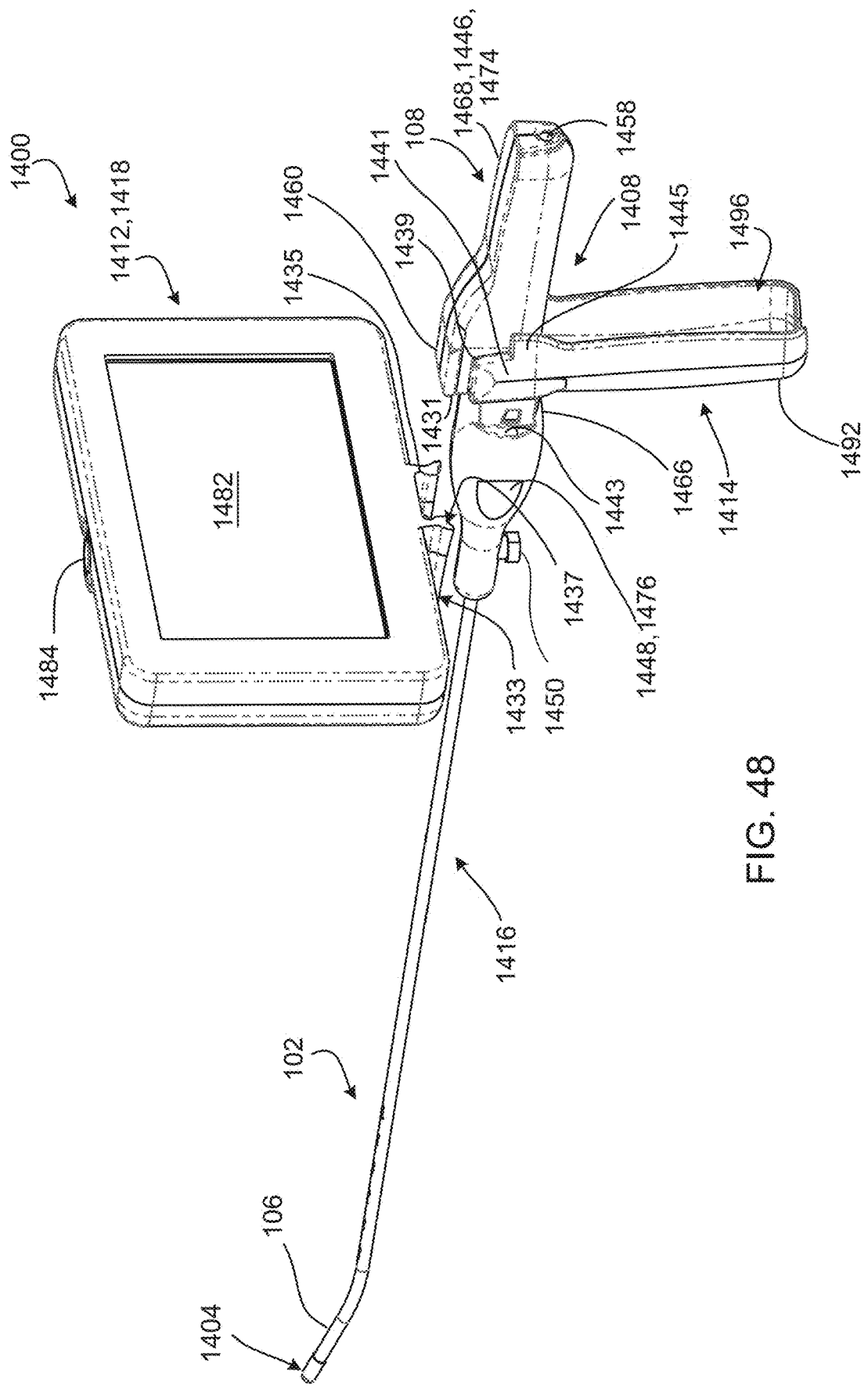
FIG. 48 is a perspective view of the endoscopic device of FIG. 42, with the display separated from the connection hub.

Referring to FIGS. 46 and 47, the display 1412 is similar in construction and function to the displays of the endoscopic devices discussed above. Accordingly, the display 1412 includes a housing 1480, a screen 1482, a power button 1484 located along an upper rear surface of the display 1412, the internal electronics 186, an electrical connector 1488 (e.g., a micro HDMI connector or another type of connector) that mates with the connection port 1460 of the connection hub 1408 to relay signals between the imaging system 1404 and the internal electronics 186, and a round metal plate 1490. The metal plate 1490 is designed to be supported by or otherwise interface with a magnet and a flexible accessory arm when the display 1412 is decoupled from the single-use portion 1416 of the endoscopic device 1400. Referring additionally to FIG. 48, the display 1412 further includes an attachment piece 1433 that defines a slot 1435 at which the display 1412 can be slid proximally to be attached to the connection hub 1408 along the flanges 1431 of the connection port 1460 and at which the display 1412 can be slid distally from the flanges 1431 to disassemble the display 1412 from the connection hub 1408. The slot 1435 typically has a maximum width of about 10 cm to about 30 cm (e.g., about 20 cm) for proper frictional mating with the flanges 1431 of the connection port 1460. The attachment piece 1433 further defines opposite channels 1437 that are complementary to and that contact upper edges 1439 of the handle 1414 when the display 1412 is secured to the connection hub 1408.

The housing 1480 of the display 1412 typically has a length of about 11 cm to about 15 cm (e.g., about 13 cm), a width of about 7 cm to about 9 cm (e.g., about 8 cm), and a height of about 2 cm to about 4 cm (e.g., about 3 cm). Referring particularly to FIG. 43, the display 1412 is typically oriented at an angle of about 80° to about 100° (e.g., about 90°) with respect to the connection hub 1408, as measured between the primary axis 122 of the cannula 102 and a central axis 1498 of the display 1412. The housing 1480 of the display 1412 is typically manufactured via injection molding.

Referring to FIGS. 42 and 45, the handle 1414 defines a gripping portion 1492 by which the handle 1414 can be grasped to be pivoted towards the connection hub 1408 to an in-line orientation (shown in FIG. 45) in which the handle 1414 is oriented in-line with the connection hub 1408 and the primary axis 122 of the cannula 102. The gripping portion 1492 defines a channel 1496 that surrounds the proximal portion 1468 of the connection hub 1408 when the handle 1414 is oriented in the in-line orientation. In addition to the gripping portion 1492, the handle 1414 also defines two opposite tabs 1441 that have interior detents (not shown) that snap into recesses 1443 disposed along the proximal portion 1468 of the connection hub 1408 to maintain the handle 1414 in the in-line orientation. The tabs 1441 include respective protrusions 1445 that prevent the display 1412 from being slid along the connection port 1460 to be attached to the connection hub 1408 when the handle 1414 is oriented in the in-line orientation.

The handle 1414 can also be pivoted from the in-line orientation to an off-axis orientation (shown in FIG. 42) in which the handle 1414 is oriented an angle of about 90° to about 100° (e.g., about 95°) with respect to the connection hub 1408 (FIG. 42) to provide a pistol-type grip. When the handle 1414 is in the off-axis orientation, the display 1412 can be slid along the connection port 1460 to be attached to the connection hub 1408. The channels 1437 of the attachment piece 1433 are in contact with the upper edges 1439 along the tabs 1441 of the handle 1414 when the display 1412 is attached to the connection hub 1408. To adjust the handle 1414 from the in-line orientation to the off-axis orientation, the force applied to the gripping portion 1492 of the handle 1414 must be high enough to push the interior detents of the tabs 1441 out of the recesses 1443 along the connection hub 1408. The handle 1414 is accordingly made of one or more materials (e.g., polycarbonate or copolyester or ABS) that allow the tabs 1441 to flex with respect to the recesses 1443, as well as that can chemically withstand various sterilization solutions and procedures. The handle 1414 has a length of about 7 cm to about 12 cm (e.g., about 9 cm) and a width of about 1 cm to about 3 cm (e.g., about 2 cm).

The display 1412 can be attached to the connection hub 1408 prior to inserting the cannula 102 into the patient, the display 1412 can be unattached to (e.g., and in wireless communication with) the connection hub 1408 while the cannula 102 is inserted into the patient (e.g., with the handle 1414 in the in-line orientation), or the display 1412 can be connected to the connection hub 1408 at the connection port 1460 by a display cable prior to inserting the cannula 102 into the patient (e.g., with the handle 1414 in the in-line orientation). Referring to FIG. 48, to attach the display 1412 to the connection hub 1408, the display 1412 is placed near the proximal portion 1468 and moved proximally to slide the slot 1435 onto the flanges 1431 of the connection hub 1408 until the electrical connector 1488 mates with the connection port 1460. The display 1412 is held in place on the flanges 1431 by a frictional fit. To disconnect the display 1412 from the connection hub 1408, the display 1412 is pulled distally relative to the connection hub 1460 to move the slot 1435 off of the flanges 1441.

While the above-discussed endoscopic devices has been described and illustrated as including certain dimensions, shapes, and material formulations, in some embodiments, an endoscopic device that is similar in construction and function to any of the above-discussed endoscopic devices may include one or more dimensions, shapes, and/or materials formulations that are different from the ones discussed above. Other embodiments are within the scope of the following claims.

Figure 49:
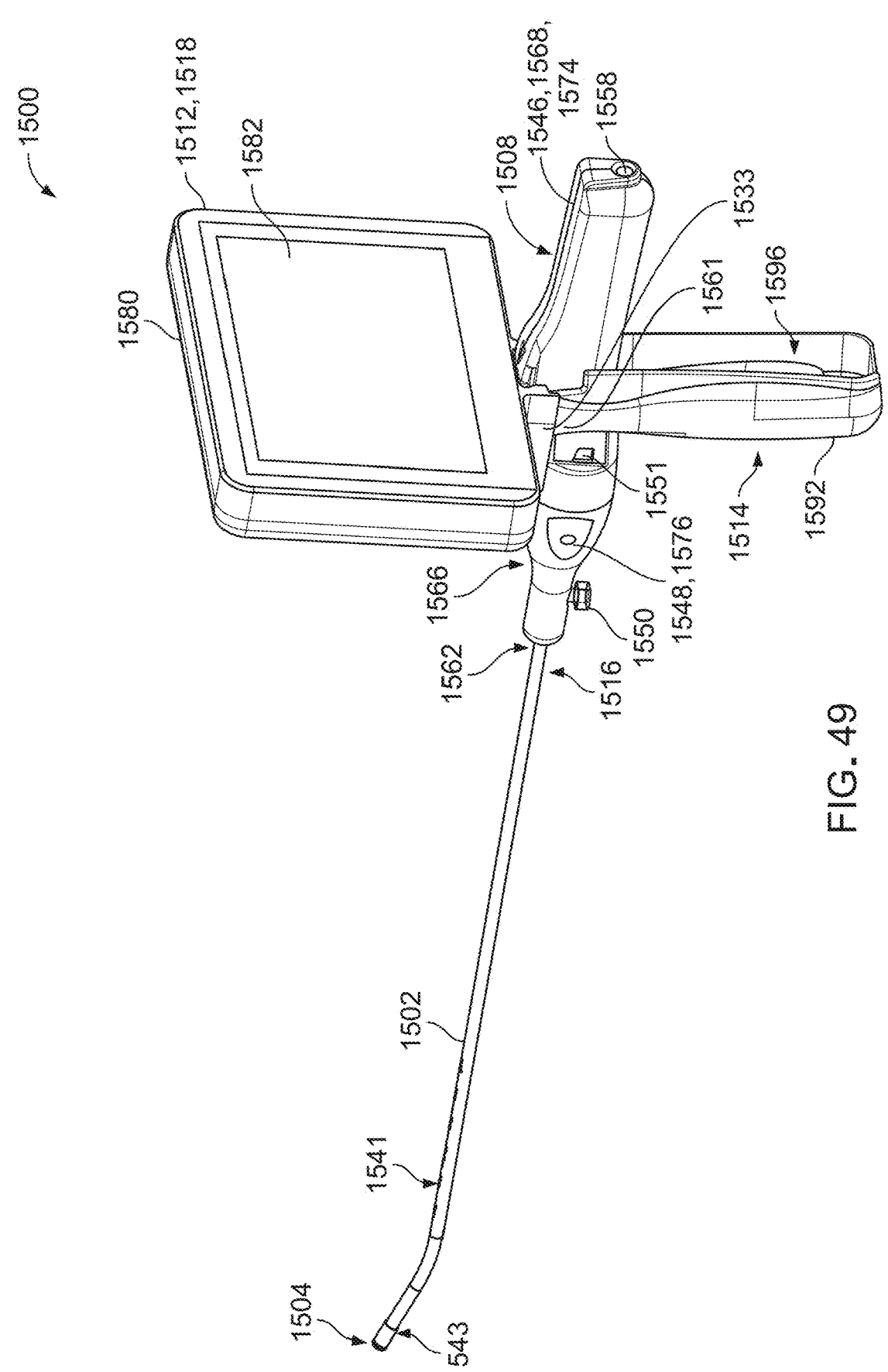
FIG. 49 is a perspective view of an endoscopic device including a pivotable handle.
Figure 50:
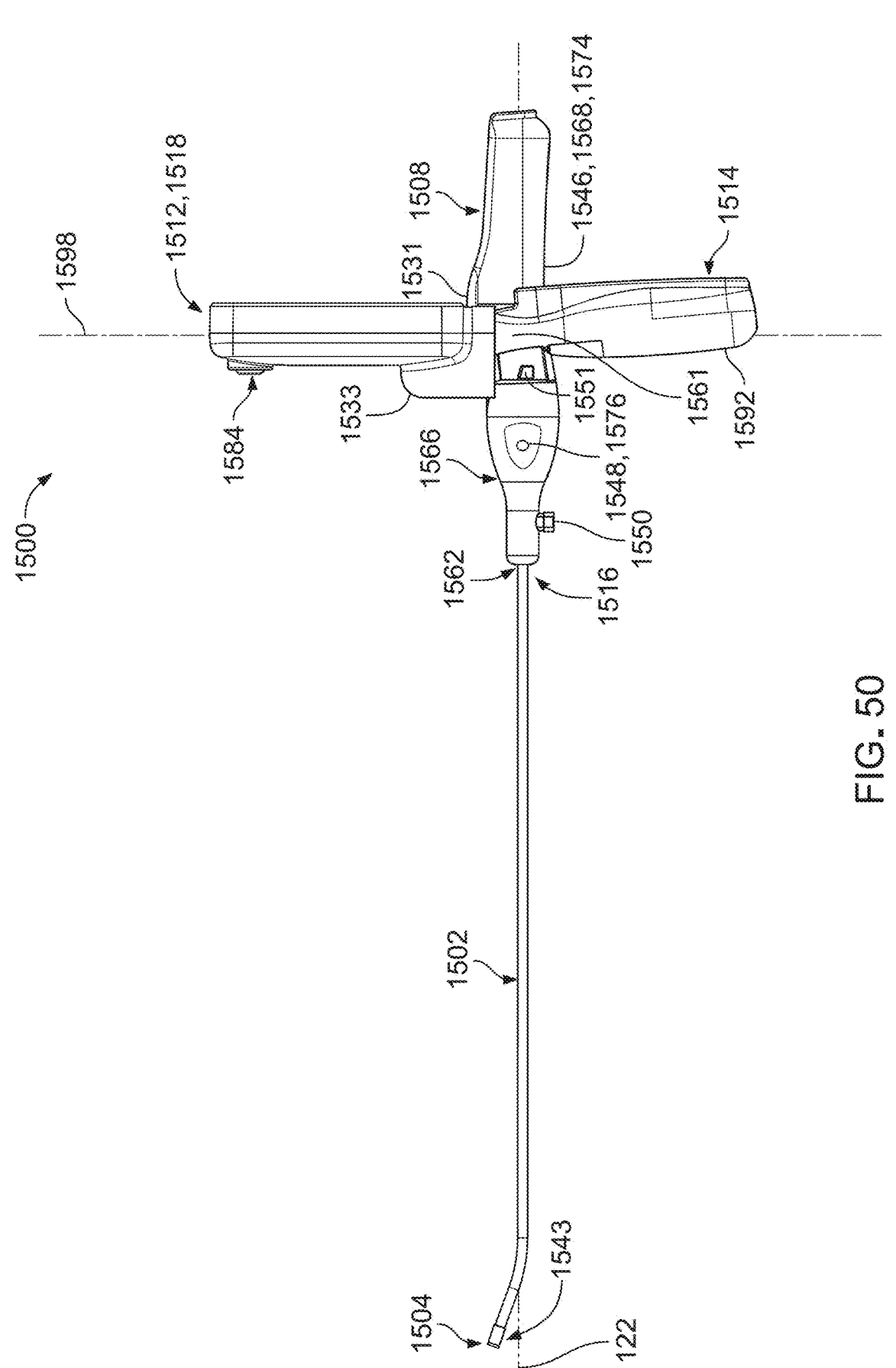
FIG. 50 is a side view of the endoscopic device of FIG. 49.
Figure 51:
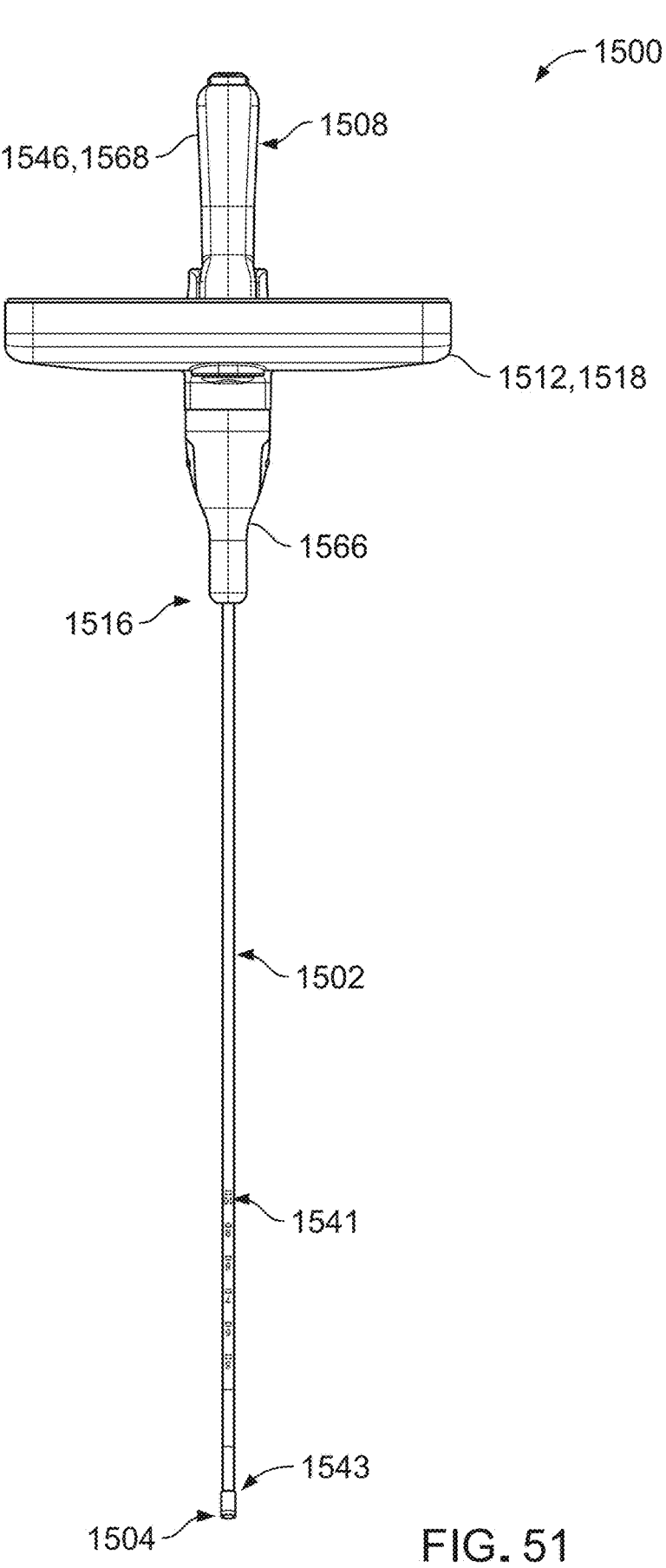
FIG. 51 is a top view of the endoscopic device of FIG. 49.
Figure 52:
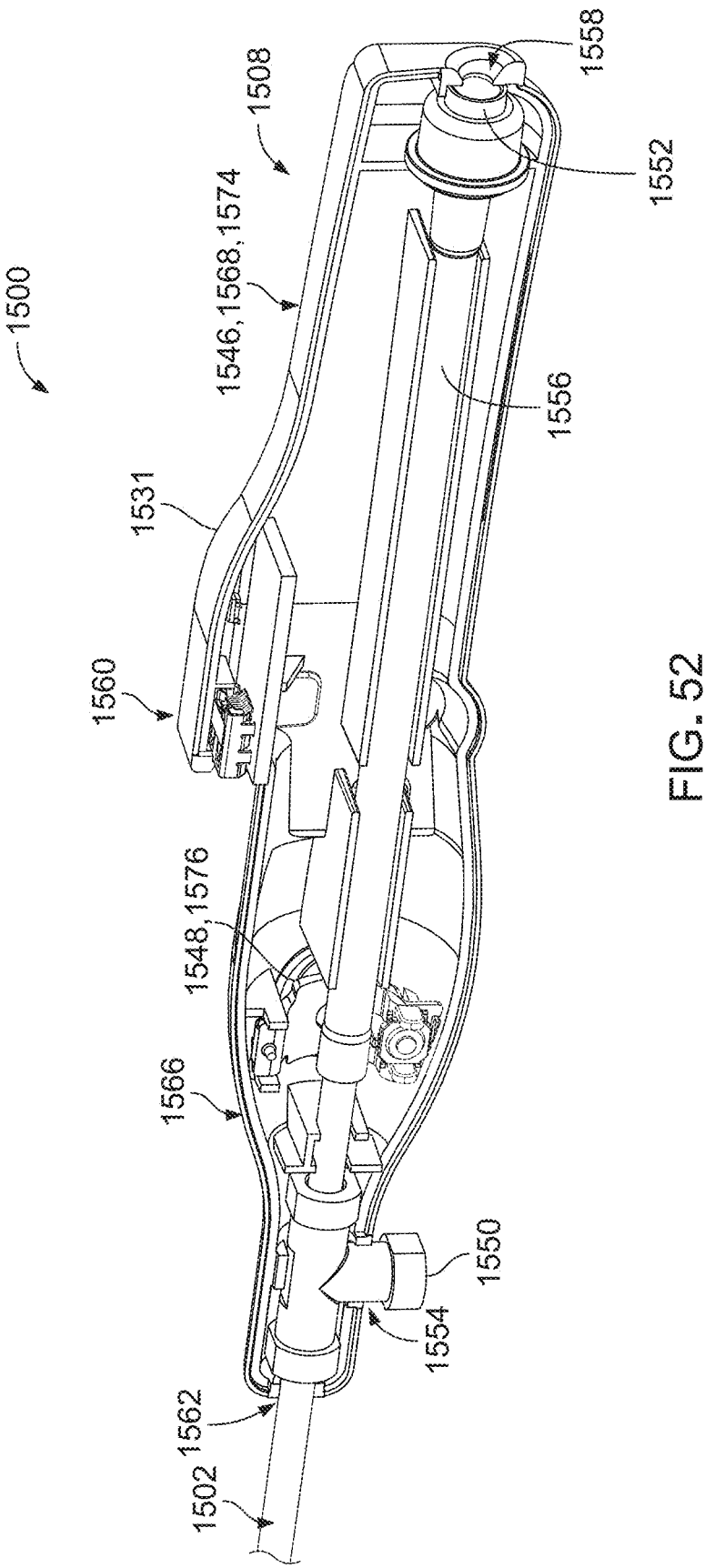
FIG. 52 is a perspective cross-sectional view of a connection hub and a handle of the endoscopic device of FIG. 49.

FIGS. 49-51 illustrate another endoscopic device 1500 that includes a display 1512 and a pivotable handle 1514 that are supported by a connection hub 1508. The endoscopic device 1500 is similar in construction and function in several aspects to the above-discussed endoscopic devices and accordingly further includes a cannula 1502 and an imaging system 1504. The cannula 1502, the imaging system 1504, the connection hub 1508, and the handle 1514 together form a single-use portion 1516 of the endoscopic device 1500, while the display 1512 provides a reusable portion 1518 of the endoscopic device 1500.

Referring particularly to FIG. 51, the cannula 1502 is substantially similar in structure and function to the cannula 102, except that the cannula 1502 further includes ruled markings 1541 that indicate distances from a distal end 1543 of the cannula 1502. That is, the cannula 1502 includes all of the components of the cannula 102 that have been described and illustrated above, as well as the ruled markings 1541 disposed along the cannula 1502. The ruled markings 1541 can be viewed by a user during a laparoscopic procedure to determine a depth to which the 1502 has been inserted into the patient. The ruled markings 1541 may be provided in metric units or English units or provided as a dimensionless scale.

Referring to FIGS. 52-55, the connection hub 1508 surrounds the proximal end region 110 of the cannula 1502 and serves as a mounting piece for the reusable display 1512. The connection hub 1508 also provides several features for fluid and electrical communication between the proximal end region 110 of the cannula 1502 and the distal tip 106 of the cannula 1502. For example, the connection hub 1508 includes a housing 1546, a camera actuator 1548 (e.g., providing two opposite push buttons 1576), a fluid port 1550 located adjacent the proximal end region 110 of the cannula 1502, an entry port 1552 disposed at a proximal opening 1558 of the housing 1546, and a straight operative conduit 1556 that extends from the proximal end region 110 of the cannula 1502 to the entry port 1552.

The housing 1546 is generally axially aligned with the primary axis 122 of the cannula 1502 and has a generally curved profile that is laterally symmetric. The housing 1546 defines a distal opening 1562 through which the cannula 1502 passes, an opening 1554 (e.g., aligned with the side-wall opening 144 of the shaft 120) to which the fluid port is secured, the proximal opening 1558, and a horizontally oriented upper connection port 1560 (e.g., a micro HDMI port or another type of port) to which the display 1512 or a display cable can be connected. In this regard, the connection hub 1508 also includes electrical components that communicate the camera actuator 1548 with the connection port 1560. The connection port 1560 defines opposite, elongate flanges 1531 that can be engaged with the display 1512 to secure the display 1512 to the connection hub 1508. The housing 1546 further defines additional internal wall features (e.g., flanges, openings, brackets, tabs, channels etc.) that properly position the fluid port 1550, the camera actuator 1548, the connection port 1560, and the entry port 1552.

A distal portion 1566 of the housing 1546 provides fluid communication between the distal tip 106 of the cannula 1502 (e.g., at the luminal opening 132) and the fluid port 1550 and provides fluid communication between the distal tip 106 and the operative conduit 1556 (e.g., for further fluid communication to the entry port 1552). The distal portion 1566 of the housing 1546 further provides electrical communication between the distal tip 106 of the cannula 102 (e.g., at the camera 142) and the camera actuator 1548, and between the distal tip 106 (e.g., at the camera 142) and the display 1512 (e.g., via the connection port 1560).

Figure 54:
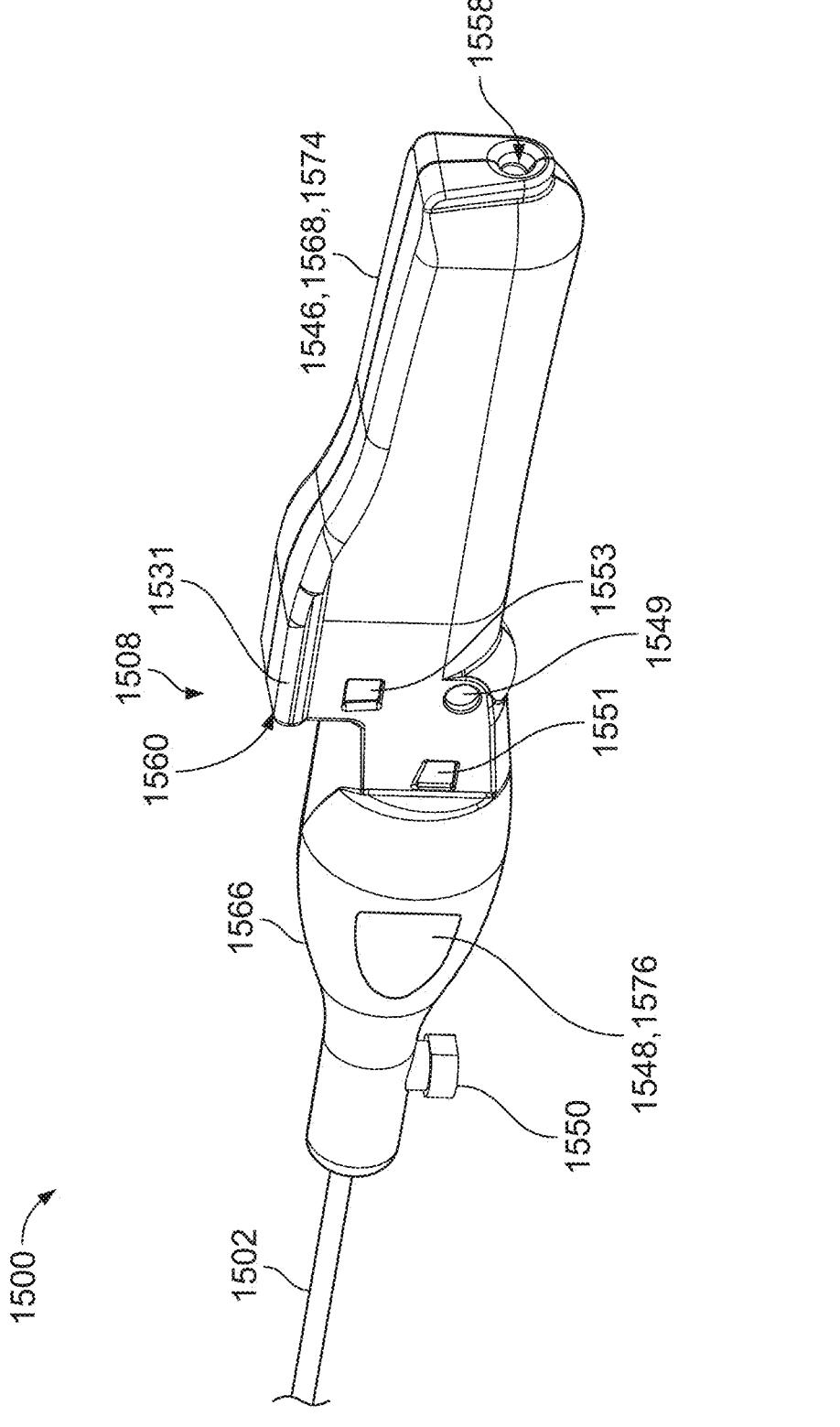
FIG. 54 is a perspective view of the connection hub of FIG. 52, with the handle omitted.
Figure 55:
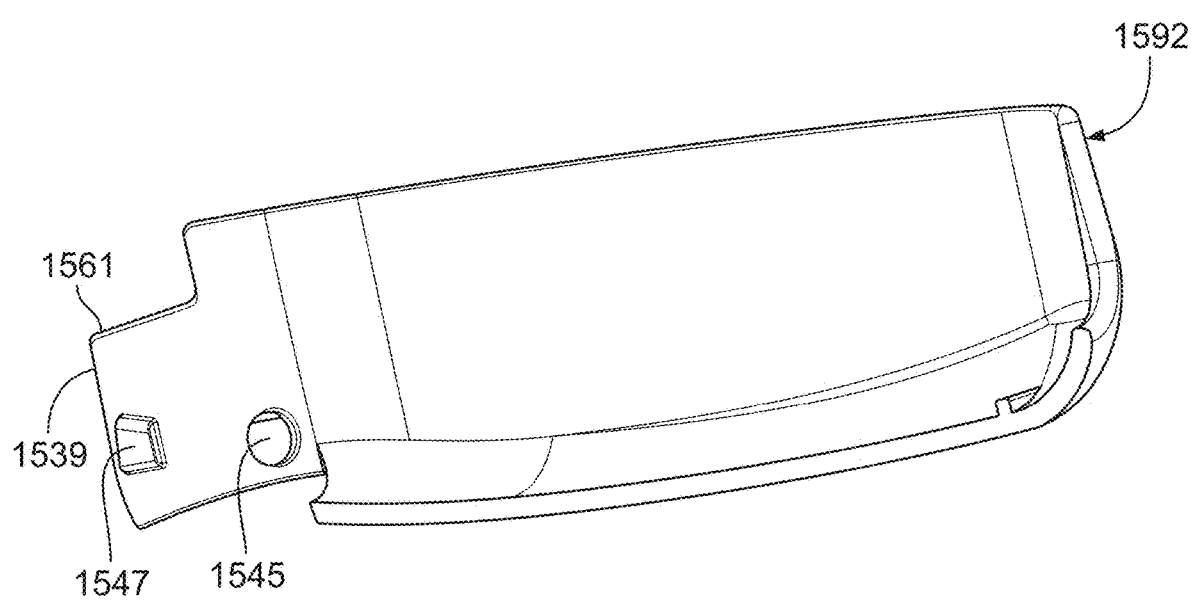
FIG. 55 is a perspective cross-sectional view of the handle of FIG. 52.

A proximal portion 1568 of the housing 1546 provides a grip 1574 that can be used to manipulate the endoscopic device 1500, and the handle 1514 is pivotable with respect to the proximal portion 1568. Referring particularly to FIG. 55, the handle 1514 defines a circular protrusion 1545 by which the handle 1514 can rotate with respect to the proximal portion 1568 and a polygonal protrusion 1547 by which a position of the handle 1514 can be locked with respect to the proximal portion 1568. Referring particularly to FIG. 54, the proximal portion 1568 of the housing 1546 defines a circular recess 1549 that is sized to receive the circular protrusion 1545 to allow the handle 1514 to pivot with respect to the proximal portion 1568. The proximal portion 1568 further defines a polygonal recess 1551 by which the handle 1514 can be locked in an in-line configuration (e.g., a "pencil-grip" configuration) and a polygonal recess 1553 by which the handle 1514 can be locked in an off-axis configuration (e.g., a "pistol grip" configuration in which the handle 1514 is oriented antiparallel to the connection hub 1508), as illustrated in FIGS. 49 and 50, and as will be discussed in more detail below.

The housing 1546 of the connection hub 1508 typically has a length (e.g., as measured along the primary axis 122 of the cannula 1502) of about 10 cm to about 20 cm (e.g., about 15 cm) and a maximum width of about 20 cm to about 30 cm (e.g., about 25 cm). The proximal portion 1568 of the housing 1546 (e.g., excluding the grip 1574) typically has a width of about 1.4 cm to about 1.8 cm (e.g., about 1.6 cm). The housing 1546 is typically made of one or more materials, such as ABS, polycarbonate, and copolyester, and is typically manufactured via injection molding. The fluid port 1550, the operative conduit 1556, and the entry port 1552 are substantially similar in construction and function to the fluid port 150, the operative conduit 156, and the entry port 152 described above with respect to the endoscopic device 100, except that the entry port 1552 is straight instead of curved.

The imaging system 1504 is also similar in construction and function to the imaging system 104. For example, the imaging system 1504 includes the camera 142, the LEDs 138 located on opposite sides of the camera 142 to evenly illuminate surrounding tissues for image acquisition, the camera actuator 1548, one or more electrical cables (e.g., one or more video and control cables, not shown) that extend from the camera 142 and the LEDs 138 to the camera actuator 1548 and to the connection port 1560, and other electrical components that provide electrical communication amongst the various components of the imaging system 1504 and the connection port 1560.

In some embodiments, the one or more electrical cables extend through the lumen 128 of the cannula 1502. In some embodiments, the one or more electrical cables extend within channels in a sidewall of the cannula 1502. In some embodiments, the imaging system 1504 includes a flex circuit member to carry the electrical communications instead of one or more electrical cables. The push buttons 1576 are flexible components that may be formed from an overmolded elastomer such that when either or both of the push buttons 1576 are depressed, the push buttons 1576 temporarily move internal components of the camera actuator 1548 to initiate image capture, as described above with respect to the push buttons 176 and the camera actuator 148.

Figure 56:
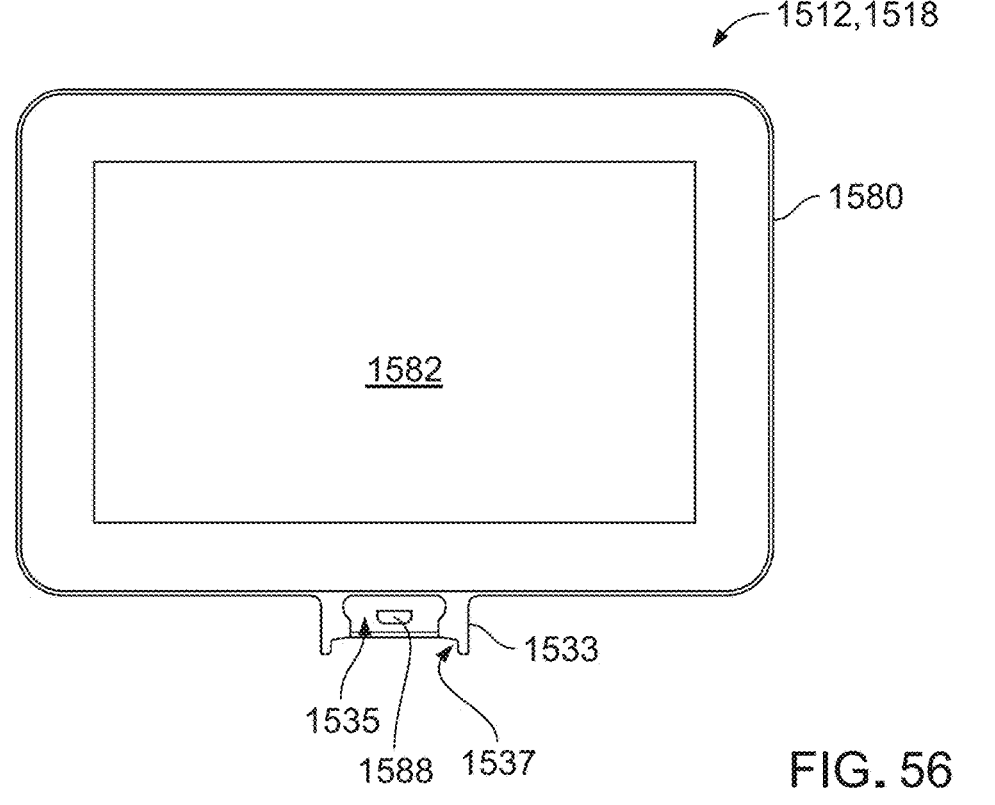
FIG. 56 is a front view of a display of the endoscopic device of FIG. 49.
Figure 57:
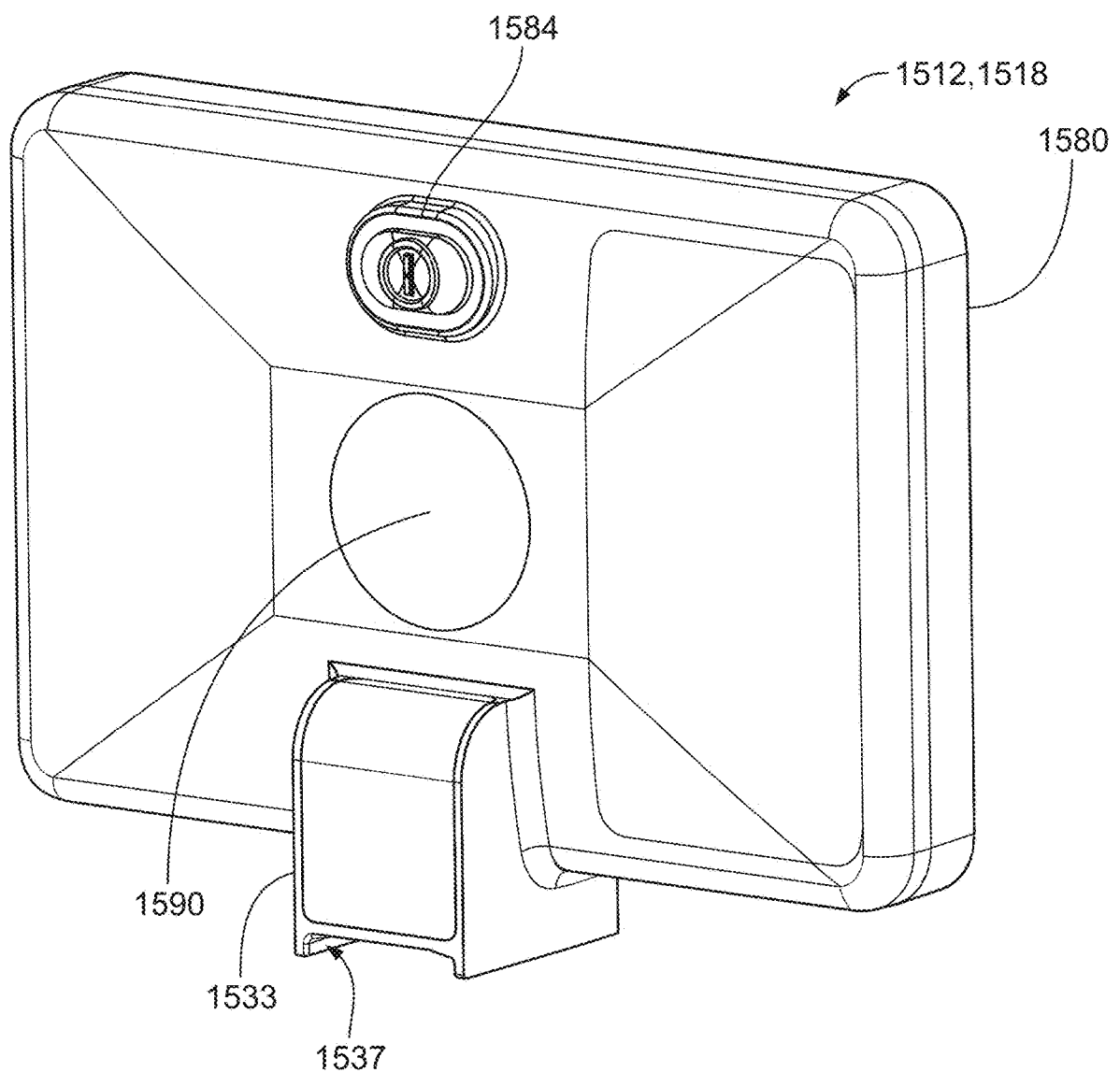
FIG. 57 is a rear perspective view of the display of FIG. 56.
Figure 58:
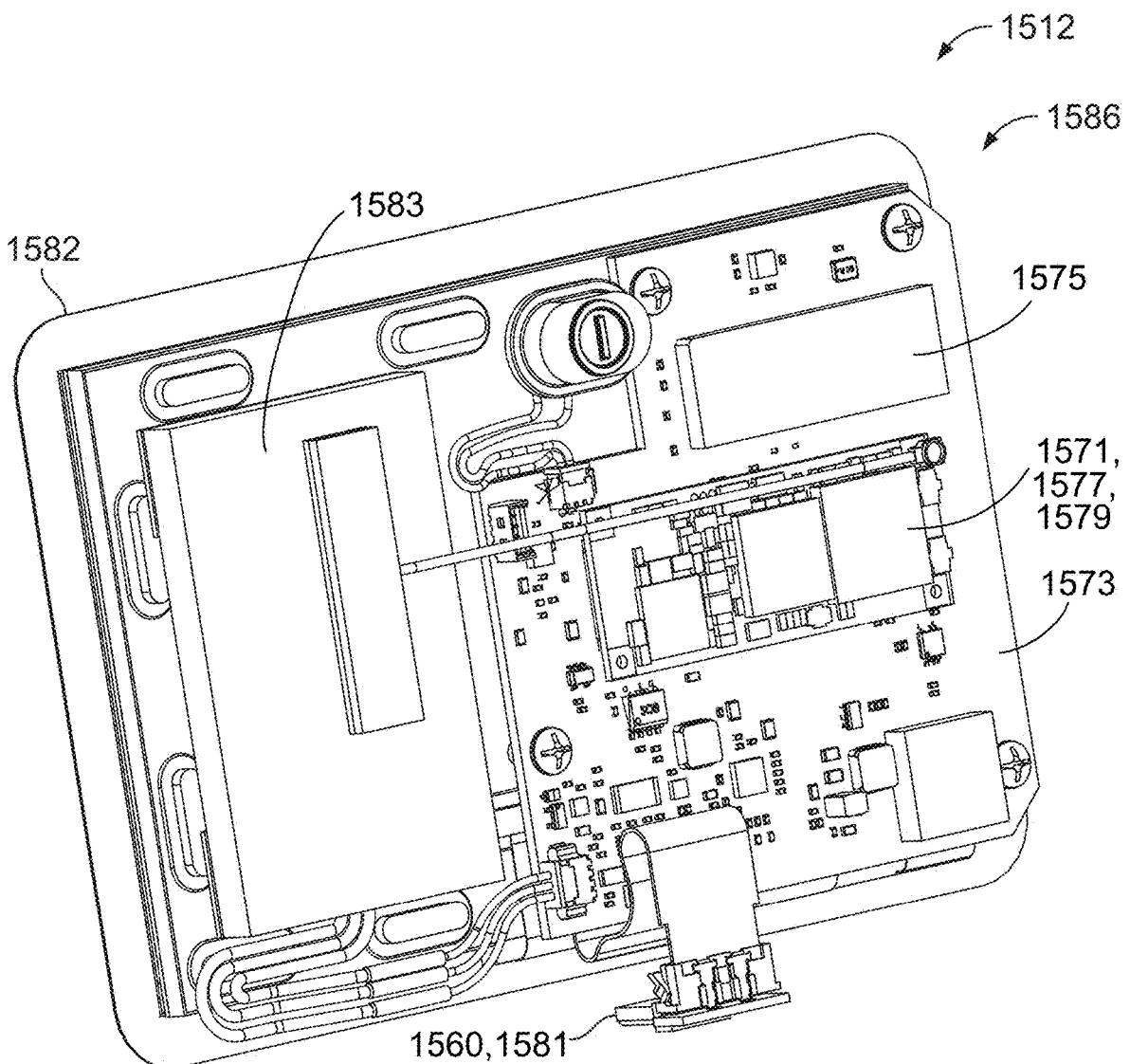
FIG. 58 is a rear perspective view of electronics within the display of FIG. 56.

Referring to FIGS. 56-58, the display 1512 is similar in construction and function to the displays of the endoscopic devices discussed above. Accordingly, the display 1512 includes a housing 1580, a screen 1582, a power button 1584 located along an upper rear surface of the display 1512, internal electronics 1586, an electrical connector 1588 (e.g., a micro HDMI connector or another type of connector) that mates with the connection port 1560 of the connection hub 1508 to relay signals between the imaging system 1504 and the internal electronics 1586, and a round metal plate 1590. The metal plate 1590 is designed to be supported by or otherwise interface with a magnet and/or a flexible accessory arm when the display 1512 is decoupled from the single-use portion 1516 of the endoscopic device 1500.

The display 1512 further includes an attachment piece 1533 that defines a slot 1535 at which the display 1512 can be slid proximally to be attached to the connection hub 1508 along the flanges 1531 of the connection port 1560 and at which the display 1512 can be slid distally from the flanges 1531 to disassemble the display 1512 from the connection hub 1508. The slot 1535 typically has a maximum width of about 10 cm to about 30 cm (e.g., about 20 cm) for proper frictional mating with the flanges 1531 of the connection port 1560. The attachment piece 1533 further defines opposite channels 1537 that are complementary to and that contact edges 1539 of the handle 1514 when the display 1512 is secured to the connection hub 1508.

The housing 1580 of the display 1512 typically has a length of about 11 cm to about 15 cm (e.g., about 13 cm), a width of about 7 cm to about 9 cm (e.g., about 8 cm), and a height of about 2 cm to about 4 cm (e.g., about 3 cm). Referring particularly to FIG. 50, the display 1512 is typically oriented at an angle of about 80° to about 100° (e.g., about 90°) with respect to the connection hub 1508, as measured between the primary axis 122 of the cannula 1502 and a central axis 1598 of the display 1512. The housing 1480 of the display 1412 is typically manufactured via injection molding. The display 1512 typically has a weight of about 0.2 kg to about 0.3 kg.

As discussed above with respect to the internal electronics 186, the internal electronics 1586 are programmed or otherwise configured to process or manipulate data acquired by the camera 142, to generate GUIs displayed on the screen 1582, to transmit data via a wired connection between the display 1512 and the imaging system 1504, to transmit data wirelessly between the display 1512 and other devices (e.g., a computer, a smart phone, or a tablet) that are not mechanically connected to the endoscopic device 1500, to power the endoscopic device on and off, and to implement various user-selected settings of the endoscopic device 1500. The internal electronics 1586 include a microprocessor 1571, a PCB 1573, an ISP 1575, a WiFi module 1577, a battery management circuit, a current monitor circuit, an on board memory 1579 (e.g., non-volatile storage memory), a USB interface 1581, and a rechargeable battery 1583 with a charging capacity of about 1400 mAh needed to carry out the functionality of the imaging system 1504 and other features of the endoscopic device 1500.

The electrical connecter 1588 serves multiple purposes, including video-out to an external display, connector to an AC adapter for charging the rechargeable battery, and/or as a port to a host PC for downloading and uploading images, video and/or settings, as well as for charging the rechargeable battery. The on board memory is used to accept flash memory cards used to store images, video and/or settings for the endoscopic device 100.

Figure 53:
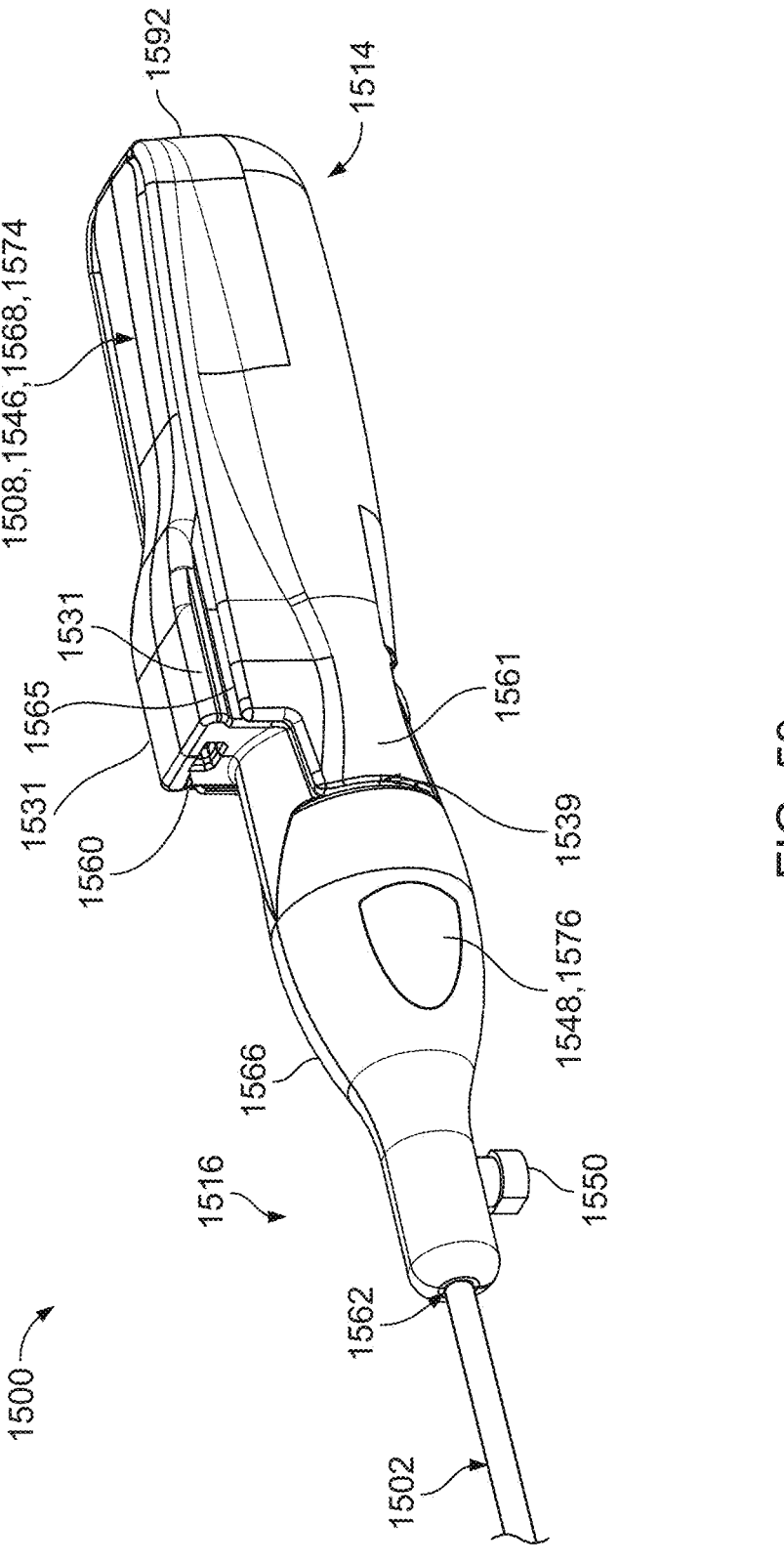
FIG. 53 is a perspective view of the connection hub and the handle of FIG. 52.

Referring to FIGS. 49 and 53, the handle 1514 defines a gripping portion 1592 by which the handle 1514 can be grasped to be pivoted towards the connection hub 1508 to an in-line configuration (shown in FIG. 53) in which the handle 1514 is oriented and stowed in-line with the connection hub 1508. The gripping portion 1592 defines a channel 1596 that surrounds the proximal portion 1568 of the connection hub 1508 when the handle 1514 is oriented in the in-line configuration. In addition to the gripping portion 1592, the handle 1514 also defines two opposite tabs 1561 that define the protrusions 1547 that snap into the recesses 1551 disposed along the proximal portion 1568 of the connection hub 1508 to maintain the handle 1514 in the in-line configuration. The tabs 1561 include respective protrusions 1565 that prevent the display 1512 from being slid along the connection port 1560 to be attached to the connection hub 1508 when the handle 1514 is oriented in the in-line configuration (e.g., the protrusions 1565 provide an obstruction to movement of the display 1512). Accordingly, the tabs 1561 prevent the display 1512 from being attached to the single-use portion 1516 of the endoscopic device 1500 in a configuration in which the display 1512 may not be stably balanced on the connection hub 1508 and in which a user's hand (e.g., grasping the handle 1514) would obstruct a view of the display screen 1582.

The handle 1514 can also be pivoted from the in-line configuration (shown in FIG. 53) to an off-axis configuration in which the handle 1514 is oriented an angle of about 90° to about 100° (e.g., about 95°) with respect to the connection hub 1508 (shown in FIG. 49) to provide a pistol-type grip. When the handle 1514 is in the off-axis configuration, the display 1512 can be slid along the connection port 1560 to be attached to the connection hub 1508. The channels 1537 of the attachment piece 1533 are in contact with the edges 1539 along the tabs 1561 of the handle 1514 when the display 1512 is attached to the connection hub 1508.

To adjust the handle 1514 between the in-line configuration and the off-axis configuration, the force applied to the gripping portion 1592 of the handle 1514 must be high enough to push the protrusions 1547 of the tabs 1561 out of the recesses 1551 or the recesses 1553 along the connection hub 1508. The handle 1514 is accordingly made of one or more materials (e.g., including polycarbonate, copolyester, and ABS]) that allow the tabs 1561 to flex with respect to the recesses 1551, 1553, as well as that can chemically withstand various sterilization solutions and procedures. The handle 1514 has a length of about 7 cm to about 12 cm (e.g., about 9 cm) and a width of about 1 cm to about 3 cm (e.g., about 2 cm). The single-use portion 1516 of the endoscopic device 1500 (e.g., including the cannula 1502, the imaging system 1504, the connection hub 1508, and the handle 1514) typically has a weight of about 0.2 kg to about 0.4 kg.

The display 1512 can be attached to the connection hub 1508 prior to inserting the cannula 1502 into the patient, the display 1512 can be unattached to (e.g., and in wireless communication with) the connection hub 1508 while the cannula 1502 is inserted into the patient (e.g., with the handle 1514 in the in-line configuration), or the display 1512 can be connected to the connection hub 1508 at the connection port 1560 by a display cable prior to inserting the cannula 1502 into the patient (e.g., with the handle 1514 in the in-line configuration). Referring again to FIG. 49, to attach the display 1512 to the connection hub 1508, the display 1512 is placed near the proximal portion 1568 and moved proximally to slide the slot 1535 onto the flanges 1531 of the connection hub 1508 until the electrical connector 1588 mates with the connection port 1560. The display 1512 is held in place on the flanges 1531 by a frictional fit. To disconnect the display 1512 from the connection hub 1508, the display 1512 is pulled distally relative to the connection port 1560 to move the slot 1535 off of the flanges 1531.

Figure 59:
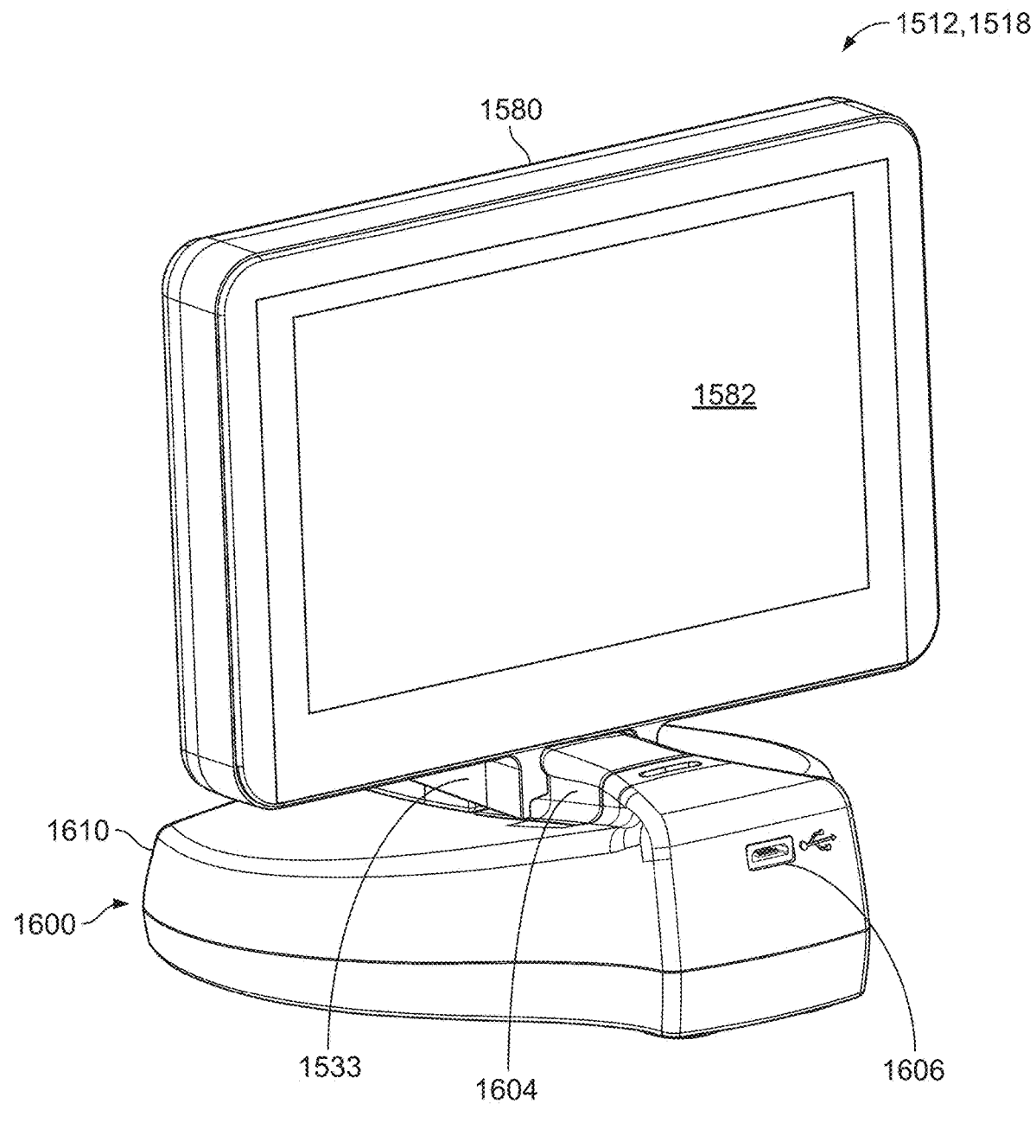
FIG. 59 is a perspective view of the display of FIG. 56, mated with a docking station.
Figure 60:
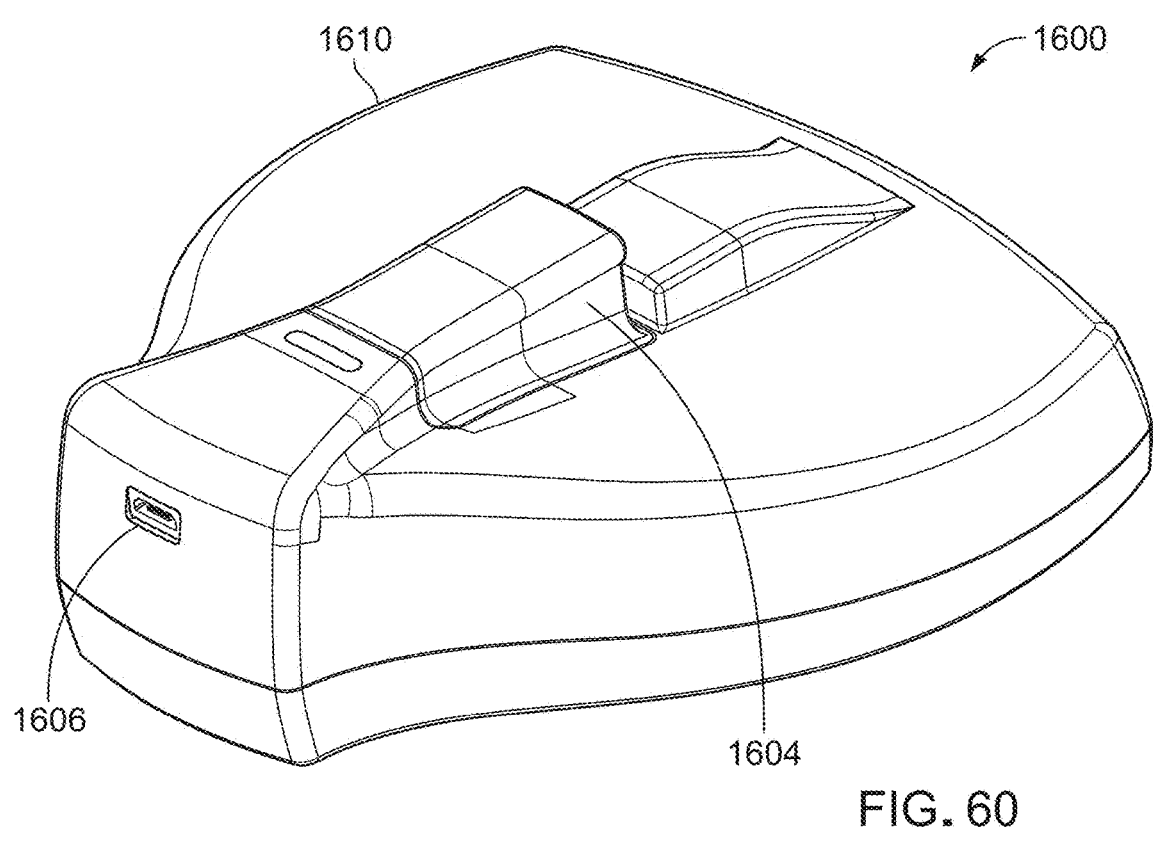
FIG. 60 is a front perspective view of the docking station of FIG. 59.
Figure 61:
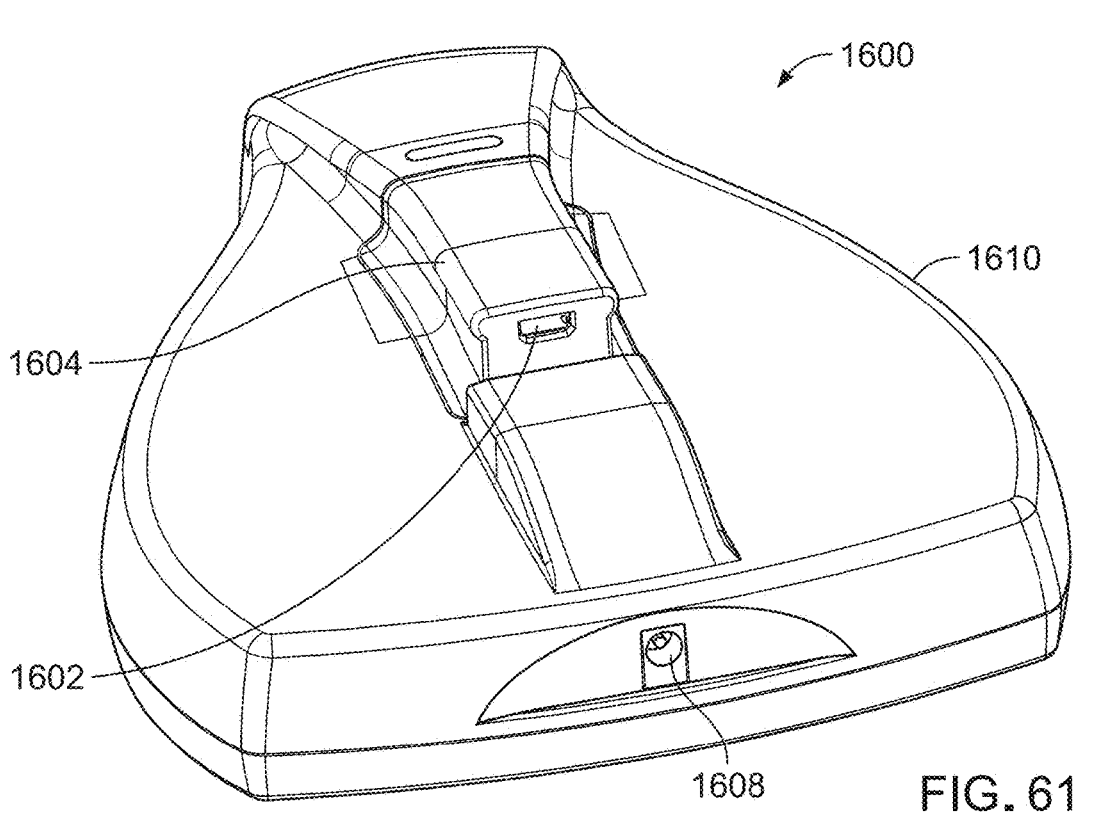
FIG. 61 is a rear perspective view of the docking station of FIG. 59.

FIGS. 59-61 illustrate a docking station 1600 to which the display 1512 of the endoscopic device 1500 can be mounted for charging and data transfer. The docking station 1600 includes a connection port 1602 (e.g., a micro HDMI port) that can be connected to the electrical connector 1588 of the display 1512, a mount 1604 that guides proper positioning of the display 1512 on the docking station 1600 (e.g., the attachment piece 1533 of the display 1512 can be slid along the mount 1604 towards the connection port 1602), a connection port 1606 to which a cable can be connected to transfer data from the display 1512 to another electronic or computing device, a power connector 1608 to which a power cable can be connected to the docking station 1600, and a housing 1610 that encloses internal electronics. The docking station 1600 typically has a length of about 9 cm to about 13 cm (e.g., about 11 cm), a width of about 9 cm to about 13 cm (e.g., about 11 cm), and a total height of about 3 cm to about 5 cm (e.g., about 4 cm). Example materials from which the housing 1610 may be made include ABS, polycarbonate, and copolyester. The docking station 1600 typically has a weight in a range of about 0.15 kg to about 0.25 kg.

As discussed above, the display 1512 may supported by or otherwise interfaced at the metal plate 1590 with an accessory component when the display 1512 is decoupled from the single-use portion 1516 of the endoscopic device 1500. Example accessory components include a rigid or flexible arm designed to attach to the display 1512 and a cable permitting the display 1512 to be positioned separately from the single-use portion 1516 of the endoscopic device 1500 while remaining functionally connected to the single-use portion 1516.

What is claimed is:

1. An endoscopic device comprising:
    a cannula configured for insertion through a cervix into a uterus of a patient;
    a camera secured to a distal end region of the cannula for acquiring images of the uterus;
    a connection hub secured to and surrounding a proximal end region of the cannula and comprising a first profile;
    a display configured to present the images acquired by the camera, the display being securable to a middle portion of the connection hub located distally of a proximal end of the connection hub, and the display being supportable by the connection hub; and
    a handle secured to and supported by the connection hub such that the connection hub couples the cannula to the handle, the handle defining a gripping portion by which the handle is configured to be grasped by a user during a surgery for positioning the endoscopic device with respect to the patient during the surgery, the gripping portion comprising a channel having a second profile that is formed complimentary to the first profile of the connection hub for surrounding at least a lower outer surface area and opposing lateral surface areas of the connection hub for stowing the handle along a length of the connection hub,
    wherein the gripping portion is pivotable toward the proximal end of the connection hub to stow the handle along the length of the connection hub.

2. The endoscopic device of claim 1, wherein, in a stowed position along the connection hub, the handle is arranged to prevent the display from attaching to the connection hub.

3. The endoscopic device of claim 2, wherein, when the handle is in the stowed position, the endoscopic device is operable for performing the surgery without the display being attached to the connection hub.

4. The endoscopic device of claim 1, wherein the handle is pivotable away from the connection hub to a position that permits attachment of the display to the connection hub.

5. The endoscopic device of claim 4, wherein the connection hub comprises a housing by which the endoscopic device can be grasped when the handle is in the position to manipulate the cannula.

6. The endoscopic device of claim 1, wherein the second profile comprises an interior profile of the handle, and wherein the first profile comprises an exterior profile of the connection hub.

7. The endoscopic device of claim 1, wherein the connection hub comprises a first recess and a second recess, and wherein the handle comprises a protrusion that is configured to mate with one of the first and second recesses at a time to respectively lock the handle in a stowed position along the connection hub or a gripping position in which the handle has pivoted away from the connection hub.

8. The endoscopic device of claim 1, further comprising internal electronics configured to implement wireless communication.

9. The endoscopic device of claim 1, further comprising internal electronics that are programmed to initiate presentation of one or more graphical user interfaces (GUIs) on the display.

10. The endoscopic device of claim 1, wherein the display is a first display, and wherein the endoscopic device is configured to transmit data wirelessly to a second display that is separate from the first display.

11. The endoscopic device of claim 1, wherein the handle is a single-use handle.

12. The endoscopic device of claim 1, wherein the handle is pivotably secured to the connection hub.

13. The endoscopic device of claim 1, wherein the connection hub, secured to the proximal end region of the cannula, comprises a grip by which the endoscopic device is manipulable when the handle has been pivoted away from the connection hub.

14. The endoscopic device of claim 1, wherein a portion of the connection hub remains exposed along an axial length of the connection hub when the second profile surrounds the first profile of the connection hub in a stowed position of the handle along the connection hub.

15. The endoscopic device of claim 1, wherein the display is securable directly to the connection hub and removable from the connection hub.

16. The endoscopic device of claim 1, wherein the middle portion of the connection hub comprises opposing flanges, and wherein the display comprises an attachment piece that is configured to slide along the opposing flanges to form a secure connection between the display and the connection hub.

17. An endoscopic system comprising:
    an endoscopic device, comprising:
        a cannula configured for insertion through a cervix into a uterus of a patient,
        a camera secured to a distal end region of the cannula for acquiring images of the uterus,
        a connection hub secured to and surrounding a proximal end region of the cannula and comprising a first profile,
        a display configured to present the images acquired by the camera, the display being securable to a middle portion of the connection hub located distally of a proximal end of the connection hub, and the display being supportable by the connection hub, and
        a handle secured to and supported by the connection hub such that the connection hub couples the cannula to the handle, the handle defining a gripping portion by which the handle is configured to be grasped by a user during a surgery for manipulating positioning the endoscopic device with respect to the patient during the surgery, the gripping portion comprising a channel having a second profile that is formed complimentary to the first profile of the connection hub for surrounding at least a lower outer surface area and opposing lateral surface areas of the connection hub for stowing the handle along a length of the connection hub;
        wherein the gripping portion is pivotable toward the proximal end of the connection hub to stow the handle along the length of the connection hub; and
    a docking station configured to mate with the display of the endoscopic device.

18. A method of examining a uterus, the method comprising:
    adjusting a position of a handle of an endoscopic device with respect to a connection hub of the endoscopic device to stow the handle along the connection hub or to remove the handle from a stowed position along the connection hub, the endoscopic device comprising a display that is securable to a middle portion of the connection hub located distally of a proximal end of the connection hub, the handle defining a gripping portion by which the handle is configured to be grasped by a user during a surgery for positioning the endoscopic device with respect to a patient during the surgery, and the gripping portion comprising a channel having a first profile that is formed complimentary to a second profile of the connection hub for surrounding at least a lower outer surface area and opposing lateral surface areas of the connection hub for stowing the handle along a length of the connection hub, wherein the gripping portion is pivotable toward the proximal end of the connection hub to stow the handle along the length of the connection hub;

inserting a cannula of the endoscopic device through a cervix into the uterus, a proximal end region of the cannula being secured to and surrounded by the connection hub such that the cannula extends from a distal end region of the connection hub, and the handle being secured to and supported by the connection hub such that the connection hub couples the cannula to the handle; and acquiring images of the uterus with a camera of the endoscopic device that is secured to a distal end region of the cannula.

19. The method of claim 18, further comprising presenting the images on the display.

20. The method of claim 18, further comprising, while the cannula is disposed within the uterus, examining the uterus using the images without the display being attached to the connection hub.

21. The method of claim 18, further comprising transmitting data wirelessly from the endoscopic device to a display that is separate from the endoscopic device.

22. The method of claim 21, wherein the display comprises a tablet.

23. The method of claim 18, further comprising pivoting the handle away from the connection hub to a position that permits attachment of the display to the connection hub.

24. The method of claim 23, further comprising grasping a housing of the connection hub to manipulate the cannula.

25. The method of claim 18, further comprising surrounding the connection hub with the handle.

* * * * *